United States Patent
Davidson et al.

(10) Patent No.: US 11,612,641 B2
(45) Date of Patent: Mar. 28, 2023

(54) METHOD FOR TREATING HUNTINGTONS'S DISEASE

(71) Applicant: UNIVERSITY OF IOWA RESEARCH FOUNDATION, Iowa City, IA (US)

(72) Inventors: Beverly L. Davidson, Iowa City, IA (US); John H. Lee, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 168 days.

(21) Appl. No.: 15/540,746

(22) PCT Filed: Dec. 30, 2015

(86) PCT No.: PCT/US2015/068034
§ 371 (c)(1),
(2) Date: Jun. 29, 2017

(87) PCT Pub. No.: WO2016/109649
PCT Pub. Date: Jul. 7, 2016

(65) Prior Publication Data
US 2018/0000907 A1    Jan. 4, 2018

Related U.S. Application Data

(60) Provisional application No. 62/098,085, filed on Dec. 30, 2014.

(51) Int. Cl.
*A61K 38/46*    (2006.01)
*A61K 48/00*    (2006.01)
*A61P 25/28*    (2006.01)
*A61K 9/00*    (2006.01)
*C12N 7/00*    (2006.01)

(52) U.S. Cl.
CPC ............ *A61K 38/46* (2013.01); *A61K 9/0085* (2013.01); *A61K 48/005* (2013.01); *A61P 25/28* (2018.01); *C12N 7/00* (2013.01); *C12Y 306/05002* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2005/0009112 A1 | 1/2005 | Edgar et al. |
| 2005/0255086 A1 | 11/2005 | Davidson et al. |
| 2012/0237625 A1* | 9/2012 | Park ..................... A61K 36/481 424/757 |
| 2014/0256795 A1 | 9/2014 | He et al. |
| 2014/0336166 A1 | 11/2014 | Briard et al. |
| 2014/0377285 A1 | 12/2014 | Liu et al. |

FOREIGN PATENT DOCUMENTS

| | | |
|---|---|---|
| WO | 2006116716 A2 | 11/2006 |
| WO | 2013116691 A1 | 8/2013 |
| WO | 2016068619 A1 | 5/2016 |
| WO | 2016109649 A1 | 7/2016 |

OTHER PUBLICATIONS

Morton et al (Journal of Huntington's Disease, 2: 3-19, 2013) (Year: 2013).*
Ross et al, (Lancet Neurol 10: 83-98, 2011) (Year: 2011).*
Baiamont et al (PLoS ONE 8(1): e53606-e53606, 2013) (Year: 2013).*
Maeler eta l, (J Neurosci. 33(9): 4206-4210), 2013 (Year: 2013).*
Fox et al (Molecular Neurodegeneration, 5(26): 1-12, 2010) (Year: 2010).*
Ramaswamy (Neurobiology of Disease 48 (2012) 243-254). (Year: 2012).*
Tsunemi (Progress in Neurobiology 97 (2012) 142-151). (Year: 2012).*
Ravikumar (Nature Genetics, 36(6): 585-586, 2004, (Year: 2004).*
Nam (Mol Neurobiol, 51: 487-499, 2015, (Year: 2015).*
Zuccato (Progress in Neurobiology, 81: 294-330, 2007). (Year: 2007).*
Bhattacharya, et al., "Genetic Removal of p70 S6 Kinase 1 Corrects Molecular, Synaptic, and Behavioral Phenotypes in Fragile X Syndrome Mice", Neuron 76, 325-337 (2012).
Bibb, et al., "Severe deficiencies in dopamine signaling in presymptomatic Huntington's disease mice", Proc Natl Acad Sci U S A 97, 6809-6814 (2000).
Cearley, et al., "A Single Injection of an Adeno-Associated Virus Vector into Nuclei with Divergent Connections Results in Widespread Vector Distribution in the Brain and Global Correction of a Neurogenetic Disease", Journal of Neuroscience 27(37), 9928-9940 (2007).
Cheng, et al., "Structural MRI detects progressive regional brain atrophy and neuroprotective effects in N171-82Q Huntington's disease mouse model", Neuroimage 56, 1027-1034 (2011).
Child, et al., "Cardiac mTORC1 Dysregulation Impacts Stress Adaptation and Survival in Huntington's Disease", Cell Reports 23, 1020-1033 (2018).

(Continued)

*Primary Examiner* — Anoop K Singh
*Assistant Examiner* — Magdalene K Sgagias
(74) *Attorney, Agent, or Firm* — Viksnins Harris Padys Malen LLP

(57) ABSTRACT

The present disclosure provides methods for treating or preventing Huntington's disease (HD) in a subject in need thereof, comprising administering a therapeutic agent that activates mTORC 1 function and/or increases Ras Homolog Enriched in Striatum (Rhes) level in the subject's brain as compared to the function or level in the subject prior to treatment, and methods for modulating mHTT-associated metabolic phenotypes and/or reversal of striatal atrophy by administering a therapeutic agent that activates mTORC1 function and/or increases Ras Homolog Enriched in Striatum (Rhes) level in the subject's brain as compared to the function or level in the subject prior to treatment.

6 Claims, 20 Drawing Sheets

Specification includes a Sequence Listing.

(56) References Cited

OTHER PUBLICATIONS

Choi, et al., "PKA modulates iron trafficking in the striatum via small GTPase, Rhes", Neuroscience 253, 214-220 (2013).
Cui, et al., "Transcriptional repression of PGC-1alpha by mutant huntingtin leads to mitochondrial dysfunction and neurodegeneration", Cell 127, 59-69 (2006).
Cunningham, et al., "mTOR controls mitochondrial oxidative function through a YY1-PGC-1 alpha transcriptional complex", Nature 450, 736-740 (2007).
Harper, et al., "RNA interference improves motor and neuropathological abnormalities in a Huntington's disease mouse model", Proc Natl Acad Sci U S A. 102(16), 5820-5825 (2005).
Hodges, et al., "Regional and cellular gene expression changes in human Huntington's disease brain", Hum Mol Genet 15, 965-977 (2006).
Humbert, et al., "The IGF-1/Akt pathway is neuroprotective in Huntington's disease and involves Huntingtin phosphorylation by Akt", Dev Cell 2(6), 831-837 (2002).
Jeong, et al., "Acetylation targets mutant huntingtin to autophagosomes for degradation", Cell 137(1), 60-72 (2009).
Jia, et al., "Selective histone deacetylase (HDAC) inhibition imparts beneficial effects in Huntington's disease mice implications for the ubiquitin-proteasomal and autophagy systems", Hum Mol Genet 21, 5280-5293 (2012).
Jiang, et al., "Small-molecule TrKB receptor agonists improve motor function and extend survival in a mouse model of huntington's disease", Hum Mol Genet 22, 2462-2470 (2013).
Johnson, et al., "Dopamine release is severely compromised in the R6/2 mouse model of Huntington's disease", J Neurochem 97, 737-746 (2006).
Karasinska, et al., "Cholesterol metabolism in Huntington disease", Nat Rev Neurol 7, 561-572 (2011).
Kim, et al., "AAV Transduction of Dopamine Neurons With Constitutively Active Rheb Protects From Neurodegeneration and Mediates Axon Regrowth", Mol Ther 20, 275-286 (2012).
Kreiner, et al., "A neuroprotective phase precedes striatal degeneration upon nucleolar stress", Cell Death Differ 20, 1455-1464 (2013).
Laplante, et al., "mTOR signaling in growth control and disease", Cell 149(2), 274-293 (2012).
Lee, "Altered MTOR Signaling in Huntington's Disease", PhD Thesis, Iowa Research Online 1-117 (2015).
Lee, et al., "Reinstating aberrant mTORC1 activity in Huntington's disease mice improves disease phenotypes", Neuron 85 (2), 303-315 (2015).
Lee, et al., "Rhes modulation reveals a critical role for mTOR activity in Huntington's Disease", Neuroscience, 43rd Annual Meeting of the Society-For-Neuroscience, Presentation Abstract, Poster 306.05, 2 pages (Nov. 13, 2013).
Lee, et al., "Rhes suppression enhances disease phenotypes in Huntington's disease mice", J Huntingtons Dis 3(1), 65-71 (2014).
Li, et al., "Huntingtin aggregate-associated axonal degeneration is an early pathological event in Huntington's disease mice", J Neurosci 21, 8473-8481 (2001).
Lu, et al., "A novel human embryonic stem cell-derived Huntington's disease neuronal model exhibits mutant huntingtin (mHTT) aggregates and soluble mHTT-dependent neurodegeneration", FASEB J 27, 1820-1829 (2013).
Macdonald, et al., "A novel gene containing a trinucleotide repeat that is expanded and unstable on Huntington's disease chromosomes", Cell 72(6), 971-983 (1993).
Mason, et al., "Glutathione peroxidase activity is neuroprotective in models of Huntington's disease", Nat Genet 45, 1249-1254 (2013).
Mcbride, et al., "Artificial miRNAs mitigate shRNA-mediated toxicity in the brain: Implications for the therapeutic development of RNAi", Proc Natl Acad Sci U S A 105, 5868-5873 (2008).
Mealer, et al., "Rhes, a Striatal-selective Protein Implicated in Huntington Disease, Binds Beclin-1 and Activates Autophagy", J Biol Chem 289, 3547-3554 (2014).
Michel, et al., "Application of the Cavalieri principle and vertical sections method to lung: estimation of volume and pleural surface area", J Microsc 150, 117-136 (1998).
Mielcarek, et al., "HDAC4 Reduction: A Novel Therapeutic Strategy to Target Cytoplasmic Huntingtin and Ameliorate Neurodegeneration", PLoS Biol 11, e1001717 (2013).
Milnerwood, et al., "Early synaptic pathophysiology in neurodegeneration: insights from Huntington's disease", Trends Neurosci 33, 513-523 (2010).
Narita, et al., "Spatial coupling of mTOR and autophagy augments secretory phenotypes", Science 332, 966-970 (2011).
O'Rourke, et al., "SUMO-2 and PIAS1 Modulate Insoluble Mutant Huntingtin Protein Accumulation", Cell Rep 4, 362-375 (2013).
Park, et al., "Promoting Axon Regeneration in the Adult CNS by Modulation of the PTEN/mTOR Pathway", Science 322, 963-966 (2008).
Patent Cooperation Treaty, International Searching Authority, Search Report and Written Opinion for PCT/US2015/068034, 9 pages, dated Mar. 31, 2016.
Peterson, et al., "mTOR complex 1 regulates lipin 1 localization to control the SREBP pathway", Cell 146, 408-420 (2011).
Porstmann, et al., "SREBP activity is regulated by mTORC1 and contributes to Akt-dependent cell growth", Cell Metab 8, 224-236 (2008).
Pryor, et al., "Huntingtin promotes mTORC1 signaling in the pathogenesis of Huntington's disease", Sci Signal 7 (349) ra103 (2014).
Ravikumar, et al., "Inhibition of mTOR induces autophagy and reduces toxicity of polyglutamine expansions in fly and mouse models of Huntington disease", Nat Genet 36(6), 585-595 (2004).
Roscic, et al., "Induction of autophagy with catalytic mTOR inhibitors reduces huntingtin aggregates in a neuronal cell model", J Neurochem 119, 398-407 (2011).
Saxena, et al., "Neuroprotection through excitability and mTOR required in ALS motoneurons to delay disease and extend survival", Neuron 80, 80-96 (2013).
Schilling, et al., "Intranuclear inclusions and neuritic aggregates in transgenic mice expressing a mutant N-terminal fragment of huntingtin", Hum Mol Genet. 8(3):397-407 (1999).
Schulte, et al., "High-Content Chemical and RNAi Screens for Suppressors of Neurotoxicity in a Huntington's Disease Model", PLoS One 6, e23841 (2011).
Seredenina, et al., "Decreased Striatal RGS2 Expression Is Neuroprotective in Huntington's Disease (HD) and Exemplifies a Compensatory Aspect of HD-Induced Gene Regulation", PLoS One 6, e22231 (2011).
Shaw, et al., "The LKB1 tumor suppressor negatively regulates mTOR signaling", Cancer Cell 6, 91-99 (2004).
She, et al., "Molecular characterization of skeletal muscle atrophy in the R6/2 mouse model of Huntington's disease", Am J Physiol Endocrinol Metab 301(1), E49-61.
Shoji-Kawata, et al., "Identification of a candidate therapeutic autophagy-inducing peptide", Nature 494(7436), 201-206 (2013).
Simmons, et al., "A Small Molecule TrkB Ligand Reduces Motor Impairment and Neuropathology in R6/2 and BACHD Mouse Models of Huntington's Disease", J Neurosci 33, 18712-18727 (2013).
Spano, et al., "Rhes Is Involved in Striatal Function", Mol Cell Biol 24, 5788-5796 (2004).
Steffan, et al., "SUMO modification of Huntingtin and Huntington's disease pathology", Science 304(5667), 100-104 (2004).
St-Pierre, et al., "Suppression of reactive oxygen species and neurodegeneration by the PGC-1 transcriptional coactivators". Cell 127(2), 397-408 (2006).
Subramaniam, et al., "Rhes, a Striatal Specific Protein, Mediates Mutant-Huntingtin Cytotoxicity", Science 324, 1327-1330 (2009).
Subramaniam, et al., "Rhes, a striatal-enriched small G-protein, mediates mTOR signaling and L-DOPA-induced dyskinesia", Nat Neurosci 15, 191-193 (2012).
Sun, et al., "Sustained axon regeneration induced by co-deletion of PTEN and SOCS3", Nature 480, 372-375 (2011).
Tabrizi, et al., "Predictors of phenotypic progression and disease onset in premanifest and early-stage Huntington's disease in the

(56) References Cited

OTHER PUBLICATIONS

TRACK-HD study: analysis of 36-month observational data", Lancet Neurol 12(7), 637-649 (2013).

Thompson, et al., "IKK phosphorylates Huntingtin and targets it for degradation by the proteasome and lysosome", J Cell Biol 187, 1083-1099 (2009).

Thoreen, et al., "An ATP-competitive mammalian target of rapamycin inhibitor reveals rapamycin-resistant functions of mTORC1", J Biol Chem 284, 8023-8032 (2009).

Trettel, et al., "Dominant phenotypes produced by the HD mutation in STHdh(Q111) striatal cells", Hum Mol Genet 9, 2799-2809 (2000).

Froca-Marín, et al., "An Increase in Basal BDNF Provokes Hyperactivation of the Akt-Mammalian Target of Rapamycin Pathway and Deregulation of Local Dendritic Translation in a Mouse Model of Down's Syndrome", J Neurosci 31(26), 9445-9455 (2011).

Tsai, et al., "Autistic-like behaviour and cerebellar dysfunction in Purkinje cell Tsc1 mutant mice", Nature 488(7413), 647-651 (2012).

Tsunemi, et al., "PGC-1α at the intersection of bioenergetics regulation and neuron function: from Huntington's disease to Parkinson's disease and beyond", Prog Neurobiol 97(2), 142-151 (2011).

Tsunemi, et al., "PGC-1α rescues Huntington's disease proteotoxicity by preventing oxidative stress and promoting TFEB function", Sci Transl Med 4 (142), 142ra97, 28 pages (2012).

Valenza, et al., "Dysfunction of the Cholesterol Biosynthetic Pathway in Huntington's Disease", J Neurosci 25(43), 9932-9939 (2005).

Valenza, et al., "Emerging roles for cholesterol in Huntington's disease", Trends Neurosci 34(9), 474-486 (2011).

Wong, et al., "Autophagy gone awry in neurodegenerative diseases", Nat Neurosci 13(7), 805-811 (2010).

Xie, et al., "BDNF Overexpression in the Forebrain Rescues Huntington's Disease Phenotypes in YAC128 Mice", J Neurosci 30, 14708-14718 (2010).

Yamamoto, et al., "Autophagy-mediated clearance of huntingtin aggregates triggered by the insulin-signaling pathway", J Cell Biol 172, 719-731 (2006).

Yamamoto, et al., "Reversal of neuropathology and motor dysfunction in a conditional model of Huntington's disease", Cell 101(1), 57-66 (2000).

Yan, et al., "Hyperactivation of Mammalian Target of Rapamycin (mTOR) Signaling by a Gain-of-Function Mutant of the Rheb GTPase", Journal of Biological Chemistry 281(29), 19793-19797 (2006).

Yu, et al., "Termination of autophagy and reformation of lysosomes regulated by mTOR", Nature 465(7300), 942-946 (2010).

Zhou, et al., "Intracellular calcium and calmodulin link brain-derived neurotrophic factor to p70S6 kinase phosphorylation and dendritic protein synthesis", J Neurosci Res 88(7), 1420-1432 (2010).

Zou, et al., "Rheb1 is required for mTORCI and myelination in postnatal brain development", Dev Cell 20, 97-108 (2011).

Zuccato, et al., "Loss of huntingtin-mediated BDNF gene transcription in Huntington's disease", Science 293 (5529), 493-498 (2001).

\* cited by examiner

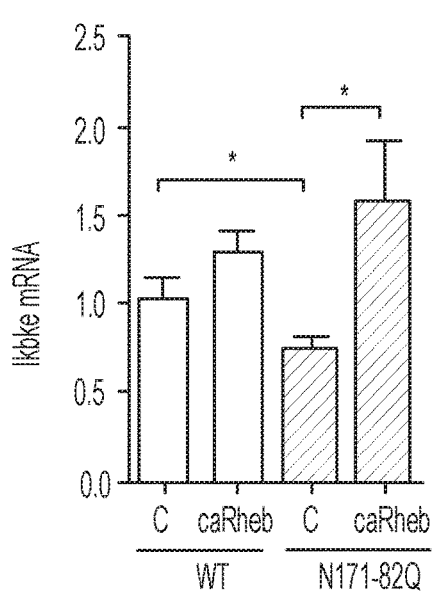
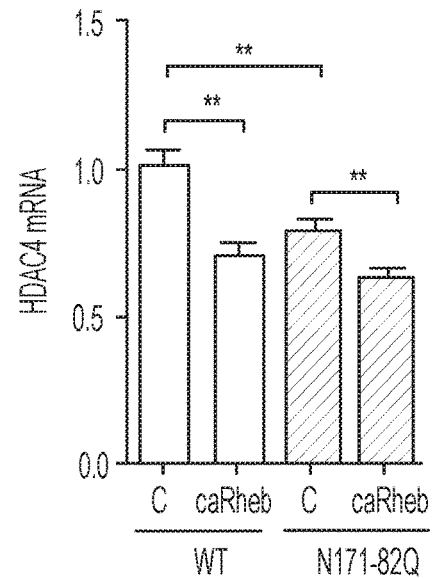
FIG. 5E    FIG. 5F
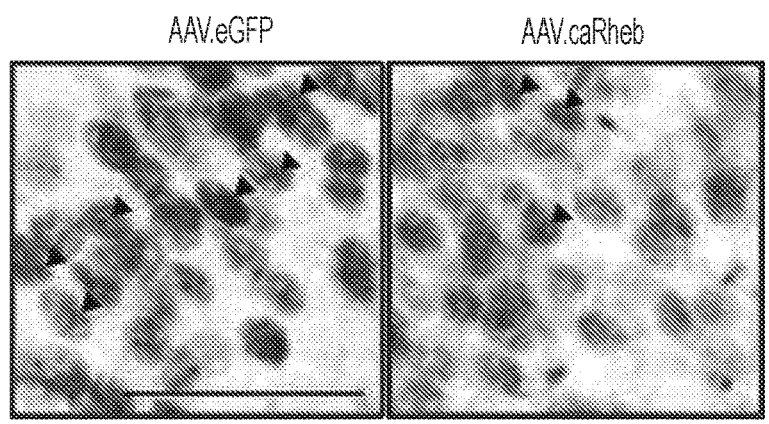
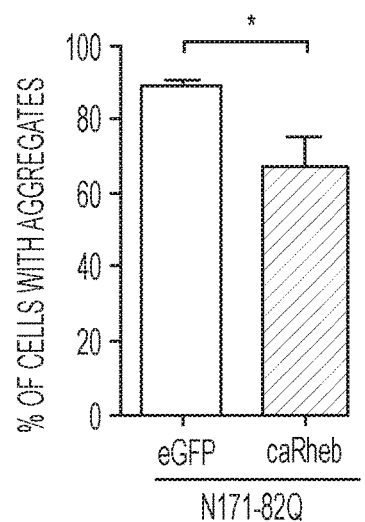
FIG. 5G

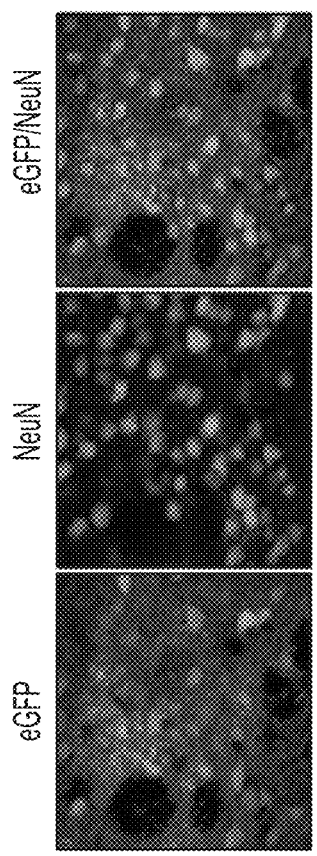
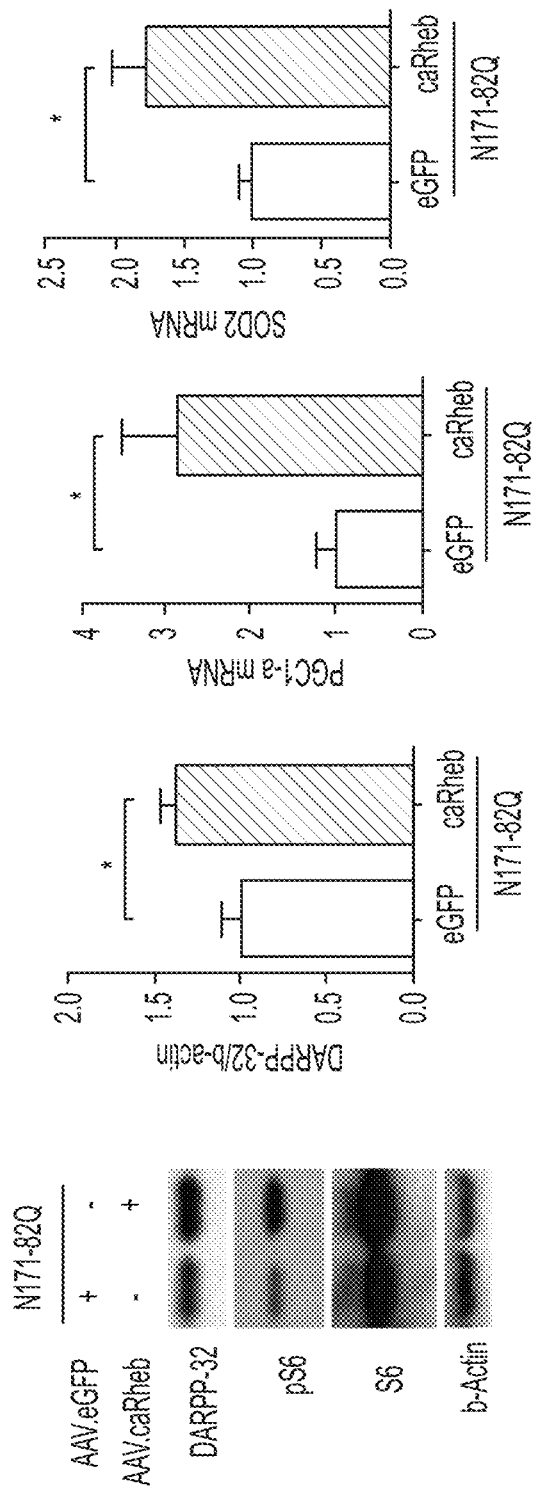
FIG. 10A
FIG. 10B
FIG. 10C
FIG. 10D

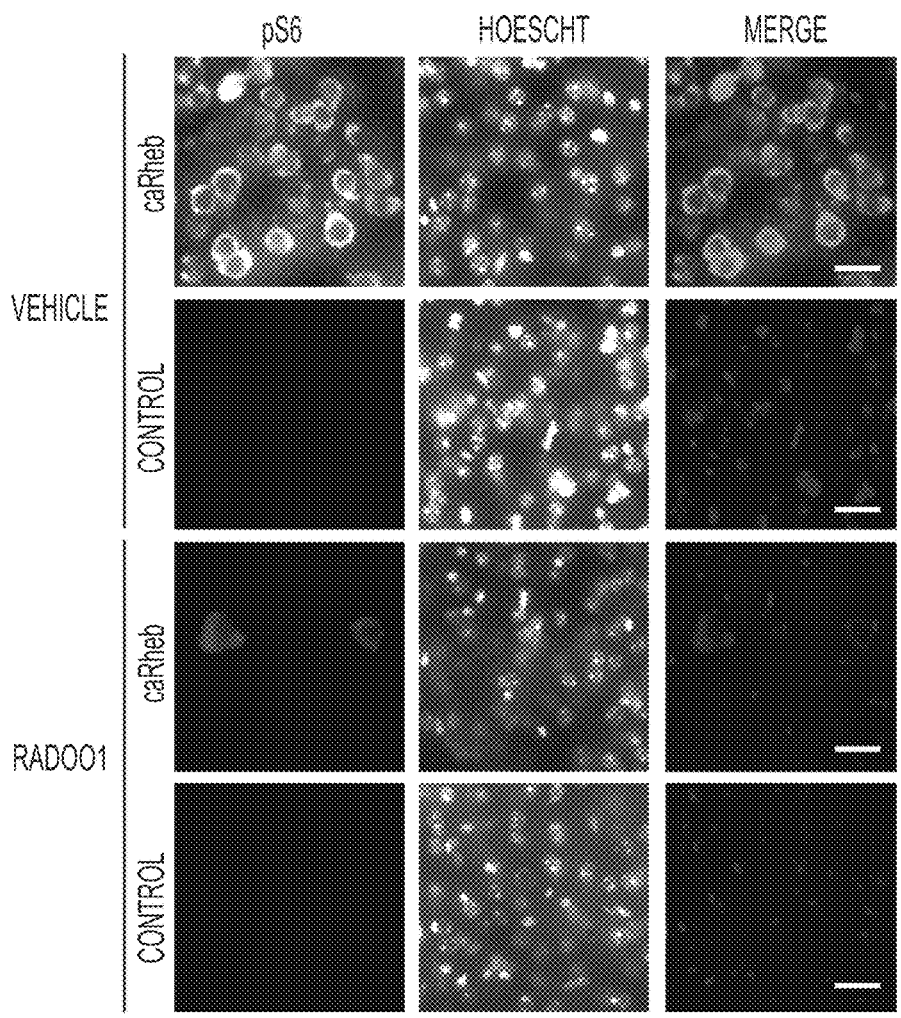
FIG. 14B
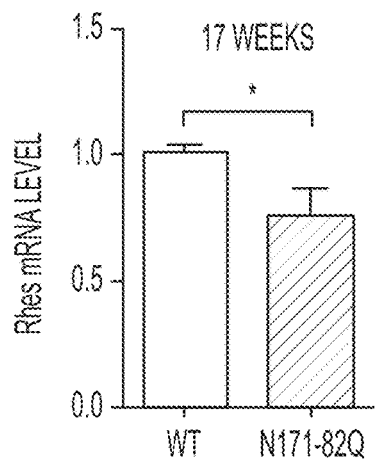 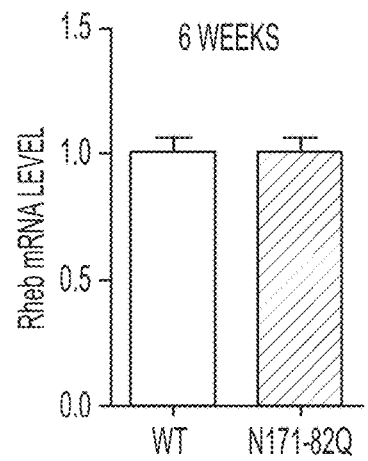
FIG. 15A  FIG. 15B

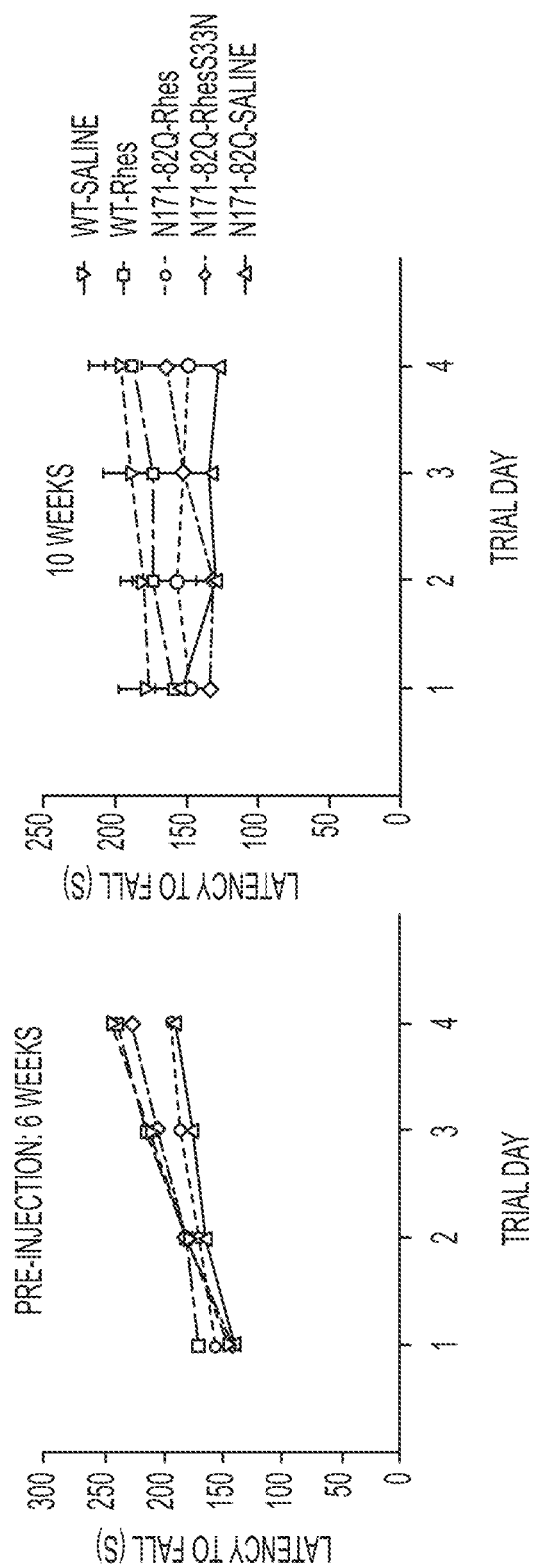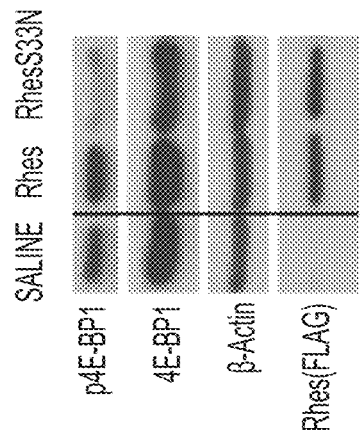
FIG. 15C
FIG. 16

METHOD FOR TREATING HUNTINGTONS'S DISEASE

RELATED APPLICATIONS

This application claims the benefit of priority of U.S. Provisional Application Ser. No. 62/098,085 filed on Dec. 30, 2014, which application is herein incorporated by reference.

STATEMENT REGARDING FEDERALLY SPONSORED RESEARCH

This invention was made with government support under NS50210 and NS052789 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 28, 2016, is named 17023164W01_SL.txt and is 11,107 bytes in size.

BACKGROUND

Huntington's Disease (HD) is a fatal autosomal-dominant neurodegenerative disease caused by CAG repeat expansion in exon 1 of huntingtin, which encodes the protein huntingtin (HTT)(1993). Despite HTT expression in all tissues and brain regions, the striatum demonstrates the most profound and early degeneration. Mutant HTT (mHTT) negatively affects multiple cellular pathways, including mitochondria biogenesis (Cui et al., 2006; Tsunemi et al., 2012), cholesterol homeostasis (Karasinska and Hayden, 2011; Valenza and Cattaneo, 2011; Valenza et al., 2005), axonal growth (Li et al., 2001), and synaptogenesis (Milnerwood and Raymond, 2010), all of which may contribute to neuronal dysfunction and loss. These varied phenotypes may result from disruption of a core component regulating a range of fundamental biological processes. Identifying such a primary pathogenic event would facilitate therapeutic development.

Gene transfer is now widely recognized as a powerful tool for analysis of biological events and disease processes at both the cellular and molecular level. More recently, the application of gene therapy for the treatment of human diseases, either inherited (e.g., ADA deficiency) or acquired (e.g., cancer or infectious disease), has received considerable attention. With the advent of improved gene transfer techniques and the identification of an ever expanding library of defective gene-related diseases, gene therapy has rapidly evolved from a treatment theory to a practical reality.

Traditionally, gene therapy has been defined as a procedure in which an exogenous gene is introduced into the cells of a patient in order to correct an inborn genetic error. Although more than 4500 human diseases are currently classified as genetic, specific mutations in the human genome have been identified for relatively few of these diseases. Until recently, these rare genetic diseases represented the exclusive targets of gene therapy efforts. Accordingly, most of the NIH approved gene therapy protocols to date have been directed toward the introduction of a functional copy of a defective gene into the somatic cells of an individual having a known inborn genetic error. Only recently, have researchers and clinicians begun to appreciate that most human cancers, certain forms of cardiovascular disease, and many degenerative diseases also have important genetic components, and for the purposes of designing novel gene therapies, should be considered "genetic disorders." Therefore, gene therapy has more recently been broadly defined as the correction of a disease phenotype through the introduction of new genetic information into the affected organism.

In in vivo gene therapy, a transferred gene is introduced into cells of the recipient organism in situ that is, within the recipient. In vivo gene therapy has been examined in several animal models. Several recent publications have reported the feasibility of direct gene transfer in situ into organs and tissues such as muscle, hematopoietic stem cells, the arterial wall, the nervous system, and lung. Direct injection of DNA into skeletal muscle, heart muscle and injection of DNA-lipid complexes into the vasculature also has been reported to yield a detectable expression level of the inserted gene product(s) in vivo.

Treatment of diseases of the central nervous system remains an intractable problem. An example of such a disease is Huntington's disease. Proteins deficient in this disorder, when delivered intravenously, do not cross the blood-brain barrier, or, when delivered directly to the brain, are not widely distributed. Earlier data indicated that inhibiting the mTOR pathway may be beneficial. However, our work reveals that this is detrimental and also show that therapies that stimulate this pathway is what is beneficial.

SUMMARY

The present invention provides in certain embodiments, methods for treating or preventing Huntington's disease (HD) in a subject in need thereof (e.g., in a subject that has inherited the disease gene), comprising administering a therapeutic agent that activates mTORC1 function and/or increases Ras Homolog Enriched in Striatum (Rhes) levels in the subject's brain as compared to the function or level in the subject prior to treatment. In certain embodiments, the subject may have mitochondrial dysfunction, aberrant cholesterol homeostasis, striatal atrophy, impaired dopamine signaling and/or decreased autophagy.

The present invention provides in certain embodiments, methods of modulating mHTT-associated metabolic phenotypes and/or reversal of striatal atrophy by administering a therapeutic agent that activates mTORC1 function and/or increases Ras Homolog Enriched in Striatum (Rhes) levels in the subject's brain as compared to the function or level in the subject prior to treatment.

The present invention provides a method of delivering a therapeutic agent to a brain cell of a mammal comprising administering to the brain cell an AAV particle containing a vector comprising the nucleic acid inserted between a pair of AAV inverted terminal repeats, thereby delivering the nucleic acid to the brain cell. In certain embodiments, the AAV is AAV2/1. In certain embodiments, the AAV is AAV2/5. As used herein, the term AAV2/1 is used to mean an AAV2 ITR and AAV1 capsid, the term AAV2/2 is an AAV2 ITR and AAV2 capsid, the term AAV2/4 is an AAV2 ITR and AAV4 capsid, etc. In certain embodiments, the AAV is AAV1, AAV2, AAV5, AAV6 and/or AAV9. In certain embodiments, the AAV is AAV1. In certain embodiments, the AAV is AAV2. In certain embodiments, the AAV is AAV5. In certain embodiments, the AAV is an AAV6. In certain embodiments, the AAV is an AAV8. In certain embodiments, the AAV is an AAV9. In certain embodiments, the AAV is an AAVrh10.

In certain embodiments, the AAV capsid has at least 80% homology to any reference AAV serotype capsid protein VP1, VP2, and/or VP3, e.g., to a AAV1 capsid protein VP1, VP2, and/or VP3, or e.g., to a AAV2 capsid protein VP1, VP2, and/or VP3, or e.g., a AAV3 capsid protein VP1, VP2, and/or VP3, or e.g., a AAV4 capsid protein VP1, VP2, and/or VP3, or e.g., a AAV5 capsid protein VP1, VP2, and/or VP3, or e.g., a AAV6 capsid protein VP1, VP2, and/or VP3, or e.g., a AAV7 capsid protein VP1, VP2, and/or VP3, or e.g., a AAV8 capsid protein VP1, VP2, and/or VP3, or e.g., a AAV9 capsid protein VP1, VP2, and/or VP3, or e.g., a AAVrh10 capsid protein VP1, VP2, and/or VP3, or e.g., a AAVrh74 capsid protein VP1, VP2, and/or VP3.

In certain embodiments, the AAV capsid has 100% homology to any reference AAV serotype capsid protein VP1, VP2, and/or VP3, e.g., to a AAV1 capsid protein VP1, VP2, and/or VP3, or e.g., to a AAV2 capsid protein VP1, VP2, and/or VP3, or e.g., a AAV3 capsid protein VP1, VP2, and/or VP3, or e.g., a AAV4 capsid protein VP1, VP2, and/or VP3, or e.g., a AAV5 capsid protein VP1, VP2, and/or VP3, or e.g., a AAV6 capsid protein VP1, VP2, and/or VP3, or e.g., a AAV7 capsid protein VP1, VP2, and/or VP3, or e.g., a AAV8 capsid protein VP1, VP2, and/or VP3, or e.g., a AAV9 capsid protein VP1, VP2, and/or VP3, or e.g., a AAVrh10 capsid protein VP1, VP2, and/or VP3, or e.g., a AAVrh74 capsid protein VP1, VP2, and/or VP3.

In certain embodiments, the subject is a human.

In certain embodiments, the therapeutic agent is a therapeutic nucleic acid. In certain embodiments, the therapeutic agent is a protein.

In certain embodiments, the agent is administered to the brain of the subject. In certain embodiments, the agent is injected at 1-5 locations in the brain, such as at one, two, or three locations in the brain. In certain embodiments, the agent is administered to the mammal's striatum, cortex or ventricular space.

BRIEF DESCRIPTION OF THE FIGURES

FIGS. 5A-5G. mTORC1 regulates genes involved in mHTT aggregate clearance. (A-F) RT-qPCR analysis of genes from striatal homogenates of 10-week-old N171-82Q and WT mice after unilateral injection of AAV.caRheb at 7 weeks of age. The uninjected contralateral side served as an internal control (N=8 per group). (A and B) Expression of genes implicated in the SUMO modification of mHTT. (C-E) Expression of IKK related genes (Ikbkb, Ikbkap, and Ikbke). (F) Expression of HDAC4. All genes were normalized to endogenous β-actin. Data represent mean+SEM. C=Control. *P<0.05, P<0.01, *P<0.001, Student's t-test. (G) Left panels, immunohistochemical staining of N171-82Q mouse striatum with EM48 2 weeks after a single unilateral injection of AAV.caRheb and AAV.eGFP into the hippocampus of 10-week N171-82Q mice (N=4 per treatment group; Scale bar: 50 µm). Right panel, AAV.caRheb reduced EM48 positive aggregates. Arrows: Em48 positive aggregates. Data represent mean+SEM. *P<0.05. Student's t test.

FIGS. 10A-10H. AAV1 efficiently transduces striatal neurons in mice. A representative immunohistochemistry picture of a HD mouse striatum showed robust transduction of neurons (NeuN) in a 18-week-old mouse after AAV1.eGFP injection at 6 weeks of age. See also McBride et al, PNAS: 105(15):5868-73, 2008. (B-H) AAV.caRheb improves metabolism-related deficits in N171-82Q mouse striatum. B) Western blot shows increased pS6 and DARPP-32 levels of striatal lysates in N171-82Q mice treated with unilateral injection of AAV.caRheb, compared to AAV.eGFP treated animals. Mice were injected at 10 weeks of age, and tissues were harvested at 13 weeks of age. Right, densitometry quantification of DARPP-32 immunoreactivity (N=4 mice per group; *P<0.05, Student's t-test). (C-H) RT-qPCR analysis of metabolism related genes and the N171-82Q transgene from striatal homogenates of 13 weeks old N171-82Q mice after unilateral injection of AAV.caRheb and contralateral injection of AAV.eGFP at 10 weeks of age (N=4 per group). All genes were normalized to β-actin. Data represent mean+ SEM. *P<0.05, **P<0.01, Student's t-test.

FIGS. 14A-14B. RAD001 inhibits mTORC1 activity in the striatum of N171-82Q mice. (A) Biochemical assessment of mTORC1 activity (pS6) in striatal lysates from N171-82Q mice that received vehicle (2% DMSO) or mTORC1 inhibitor RAD001 (N=3 mice per group). Mice were treated for 2 weeks and striata harvested 24 hours after the last dose. Densitometry analysis of immunoblots of samples from mice. β-actin was used as a loading control. Data represent mean+SEM. ***P<0.001, Student's t-test. (B) Representative photomicrographs of immunohistochemical staining for pS6 (green) and Hoescht staining (blue), 2 weeks after a single unilateral injection of AAV.caRheb into the striatum of 11-week-old N171-82Q mice. Mice were given vehicle (N=3) or RAD001 (N=4) for 2 weeks. Scale bars: 25 µm.

FIGS. 15A-15C. Rhes expression levels are reduced in HD transgenic mice striata. (A) Endogenous striatal Rhes levels in 17-week-old N171-82Q (N=4) and WT mice (N=6). Rhes mRNA abundance was normalized to endogenous β-actin. Data represent mean+SEM.*P<0.05; Student's t-test. (B) Rheb levels are unchanged in N171-82Q mice striata from 6-week-old N171-82Q (N=5) and WT mice (N=4), and 17-week-old N171-82Q (N=4) and WT mice (N=6). Student's t-test. (C) N171-82Q mice perform indistinguishably from normal at 5 and 10 weeks of age (N=10-14 mice per group). Rotarod data from four consecutive days are shown as latency to fall. Data represent mean+SEM. One-way ANOVA with Tukey post-hoc test.

FIG. 16. Transduction of N171-82Q mouse striatum with Rhes and GTPase deficient Rhes S33N. Representative western blot of mTORC1 activity (p-4E-BP1) and Rhes transgenes (Flag) in N171-82Q mice transduced with AAV.Rhes, AAV.RhesS33N, or saline in the striatum. Mice were injected at 7 weeks of age, and striatal tissues were harvested 3 weeks post-injection. β-actin was used as a loading control.

DETAILED DESCRIPTION

Therapeutic Agents

Figure 1A:
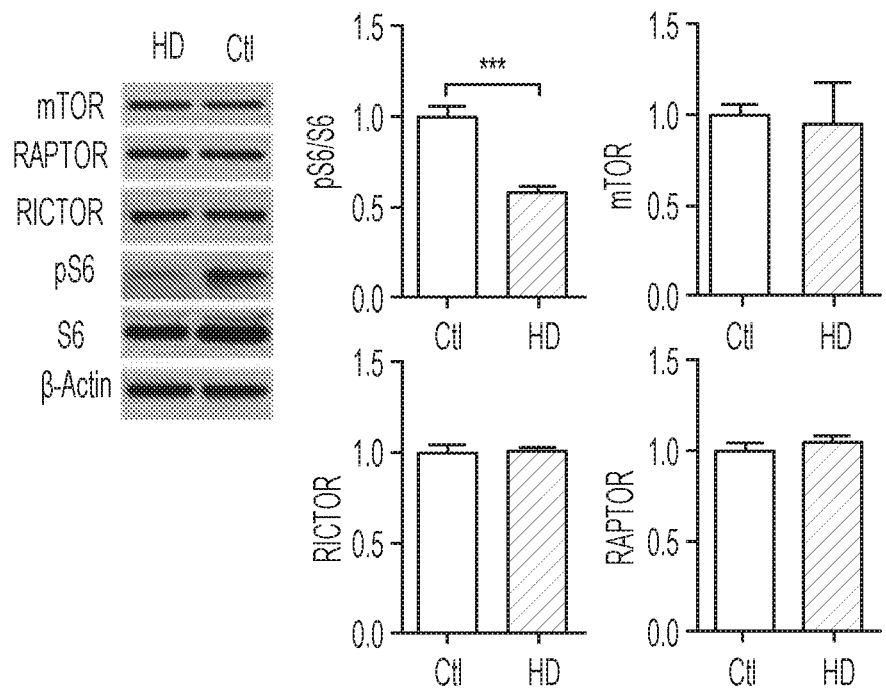
FIGS. 1A-1B. mTORC1 activity is reduced in HD human and mouse striatum. (A) Immunoblotting of mTOR, Rictor, Raptor, and mTORC1 activity (pS6) showed reduced mTORC1 activity in the striatum of patients with HD (N=10; see FIG. 9A for expanded series) compared to unaffected individuals (N=6). β-actin was used as a loading control. Data represent mean+SEM. ***P<0.001, Student's t-test. (B) Immunoblotting of mTOR, Rictor, Raptor, and pS6 from 6-week-old N171-82Q and WT mouse striatal lysates. β-actin was used as a loading control. Densitometry analyses for panels A and B revealed reduced pS6 levels in HD patient (N=10) vs. controls (N=6), and 6-week-old N171-82Q mice (N=4) compared to age- and sex-matched WT littermates (N=4). Data represent mean+SEM.*P<0.05; ***P<0.001, Student's t-test.

In certain embodiments, the present invention provides therapeutic agents to a subject in need thereof. In certain embodiments, the therapeutic agent comprises an mTORC1 regulator.

In certain embodiments, the mTORC1 regulator is Rheb (*Homo sapiens* Ras homolog enriched in brain (RHEB), mRNA NCBI Reference Sequence: NM_005614.3). Rheb sequence (coding sequence indicated in bold):

```
                                            (SEQ ID NO: 1)
GGCGTAATTAAAAAGCGGCGGAAGAAGGTGGGAGGGTCATGACGCAGCGA

GTTTCAGTCGTGACTTTTCTGGGGGCATCGCGGCGTCCCCTTTTTTTGCC

TTTAAAGTAAAACGTCGCCCCGACGCACCCCCCGCGTATTTCGGGGGCG

GAGGCGGCGGGCCACGGCGCGAAGAGGGGCGGTGCTGACGCCGGCCGGTC

ACGTGGGCGTGTTGTGGGGGGGAGGGGCGCCGCCGCGCGGTCGGTTCCGG

GCGGTTGGGAGCGCGCGAGCTAGCGAGCGAGAGGCAGCCGCGCCCGCCGC

CGCCCCTGCTCTGTATGCCGCTCTCTCCCGGCGCGGCCGCCGCCGATCAC

AGCAGCAGGAGCCACCGCCGCCGCGGTTGATGTGGTTGGGCCGGGGCTGA

GGAGGCCGCCAAGATGCCGCAGTCCAAGTCCCGGAAGATCGCGATCCTGG

GCTACCGGTCTGTGGGGAAATCCTCATTGACGATTCAATTTGTTGAAGGC

CAATTTGTGGACTCCTACGATCCAACCATAGAAAACACTTTTACAAAGTT

GATCACAGTAAATGGACAAGAATATCATCTTCAACTTGTAGACACAGCCG

GGCAAGATGAATATTCTATCTTTCCTCAGACATACTCCATAGATATTAAT

GGCTATATTCTTGTGTATTCTGTTACATCAATCAAAAGTTTTGAAGTGAT

TAAAGTTATCCATGGCAAATTGTTGGATATGGTGGGGAAAGTACAAATAC

CTATTATGTTGGTTGGGAATAAGAAAGACCTGCATATGGAAAGGGTGATC

AGTTATGAAGAAGGGAAAGCTTTGGCAGAATCTTGGAATGCAGCTTTTTT

GGAATCTTCTGCTAAAGAAAATCAGACTGCTGTGGATGTTTTTCGAAGGA

TAATTTTGGAGGCAGAAAAAATGGACGGGGCAGCTTCACAAGGCAAGTCT

TCATGCTCGGTGATGTGATTCTGCTGCAAAGCCTGAGGACACTGGGAATA

TATTCTACCTGAAGAAGCAAACTGCCCGTTCTCCTTGAAGATAAACTATG

CTTCTTTTTTCTTCTGTTAACCTGAAAGATATCATTTGGGTCAGAGCTCC

CCTCCCTTCAGATTATGTTAACTCTGAGTCTGTCCAAATGAGTTCACTTC

CATTTTCAAATTTTAAGCAATCATATTTTCAATTTATATATTGTATTTCT

TAATATTATGACCAAGAATTTTATCGGCATTAATTTTTCAGTGTAGTTTG

TTGTTTAAAATAATGTAATCATCAAAATGATGCATATTGTTACACTACTA

TTAACTAGGCTTCAGTATATCAGTGTTTATTTCATTGTGTTAAATGTATA

CTTGTAAATAAAATAGCTGCAAACCTCAGTCCTTTGTGCTACTTGATGTG

GCTTTCAAAGAAGAGAAGCCTTGTCCTGAGTTTCTCACTTGGCTTCAGGA

AGGCCCCAGGTTGGATTCCAGAAACCAGTGAAGATGTGGCCACAGGAGGA

GGTGTGCTGAGGTGGCTGCTGACCGTGGACTCCCTGCGCAGTGGCCTGCA

GATGTTGGGGCTGGGTTACAGCTGATTGAAGCTGAGTGGCCCTGGGGGGT

CTGTGAGGGGAGTTCCTCCCCAGTGATGAAATTCTCTCCTTCCACCCCTCA

AATCCCTAGACCTTGACTGAAATGCTCCGTGGTCGGGAGCCTGGTCAAGG

AGGAGGAGCTGCTGAGAGGCATTGTTCGCCCTTGCTCATAGCTTAGCTCG

ATGTCCGTGTCAGACAGGAGATGATTGAGAACAGCCTTGCCTGTCACTGT

CCTAGAACACCCTGGAGTTTAGTGTTCTGTGTCAGAGTCTTGGGAGCCTC

CTTCAGACCCAGATGACGGGCCTCCCTCTGTCCAAGGAGCAGCTGTAAAG

GAGAAGAGGGATTTCATTTGTTTGGTGGCTGTTACCTTGTCTGTAAGTCA

AACTTGGAGTTGAGCAGTGCTTTTTAAACGATTCCCTTTTGCAGCTAAAA

TTTCACAGGGCTATTTCTAATACGTAAGCAAATGTTACCATTGACTTTAT

TAATAAAATATAGTTTTGCTTTGCAAAAAAAAAAAAAAAAA.
```

In certain embodiments, the Rheb is at least 90% identical to the protein encoded by SEQ ID NO:1 (e.g., 90%, 91%, 92%, 93%, 94%, 95%, 96%, 97%, 98%, 99% or 100% identical to the protein encoded by SEQ ID NO:1). In certain embodiments, the Rheb is at least 90% identical to the protein encoded by the Rheb coding sequence, SEQ ID NO:2 (e.g., 90%, 91%, 92%, 93%, 94%, 95%, 96%, 97%, 98%, 99% or 100% identical to the protein encoded by SEQ ID NO:2), indicated in bold above. In certain embodiments, the Rheb is constitutively active Rheb mutant (caRheb; S16H). In certain embodiments, the nucleic acid encoding Rheb is a fragment or variant of SEQ ID NO: 1 or 2, or has substantial identity to SEQ ID NO: 1 or 2. In certain embodiments, the mTORC1 regulator is Rhes (*Homo sapiens* RASD family, member 2 (RASD2), mRNA NCBI Reference Sequence: NM_014310.3). Rhes sequence (coding sequence indicated in bold):

(SEQ ID NO: 3)
CCCTTGCGCCTCCTTGCCCGGCCGCGCCCAGCCCGGCGTCCCGAGCAGCG

CAGGGGAGGATCCCCGCGCAGTGACCCGGGAGCCACCACAGACTCTGGGA

GGCTCGGCGGCTGGAGCAGCAGGCAGCTCCCCGCAGCTCCCGGCGCTTCC

AGGCAGCTCTCTGAGCCGTGCCAGAGGCCCGGCCCGCCATTCCCAGCCCC

GAGCCATGATGAAGACTTTGTCCAGCGGGAACTGCACGCTCAGTGTGCCC

GCCAAAAACTCATACCGCATGGTGGTGCTGGGTGCCTCTCGGGTGGGCAA

GAGCTCCATCGTGTCTCGCTTCCTCAATGGCCGCTTTGAGGACCAGTACA

CACCCACCATCGAGGACTTCCACCGTAAGGTATACAACATCCGCGGCGAC

ATGTACCAGCTCGACATCCTGGATACCTCTGGCAACCACCCCTTCCCCGC

CATGCGCAGGCTGTCCATCCTCACAGGGGATGTCTTCATCCTGGTGTTCA

GCCTGGATAACCGGGAGTCCTTCGATGAGGTCAAGCGCCTTCAGAAGCAG

ATCCTGGAGGTCAAGTCCTGCCTGAAGAACAAGACCAAGGAGGCGGCGGA

GCTGCCCATGGTCATCTGTGGCAACAAGAACGACCACGGCGAGCTGTGCC

GCCAGGTGCCCACCACCGAGGCCGAGCTGCTGGTGTCGGGCGACGAGAAC

TGCGCCTACTTCGAGGTGTCGGCCAAGAAGAACACCAACGTGGACGAGAT

GTTCTACGTGCTCTTCAGCATGGCCAAGCTGCCACACGAGATGAGCCCCG

CCCTGCATCGCAAGATCTCCGTGCAGTACGGTGACGCCTTCCACCCCAGG

CCCTTCTGCATGCGCCGCGTCAAGGAGATGGACGCCTATGGCATGGTCTC

GCCCTTCGCCCGCCGCCCCAGCGTCAACAGTGACCTCAAGTACATCAAGG

CCAAGGTCCTTCGGGAAGGCCAGGCCCGTGAGAGGGACAAGTGCACCATC

CAGTGAGCGAGGGATGCTGGGGCGGGGCTTGGCCAGTGCCTTCAGGGAGG

TGGCCCCAGATGCCCACTGTGCGCATCTCCCCACCGAGGCCCCGGCAGCA

GTCTTGTTCACAGACCTTAGGCACCAGACTGGAGGCCCCGGGCGCTGGC

CTCCGCACATTCGTCTGCCTTCTCACAGCTTTCCTGAGTCCGCTTGTCCA

CAGCTCCTTGGTGGTTTCATCTCCTCTGTGGGAGGACACATCTCTGCAGC

CTCAAGAGTTAGGCAGAGACTCAAGTTACACCTTCCTCTCCTGGGGTTGG

AAGAAATGTTGATGCCAGAGGGGTGAGGATTGCTGCGTCATATGGAGCCT

CCTGGGACAAGCCTCAGGATGAAAAGGACACAGAAGGCCAGATGAGAAAG

GTCTCCTCTCTCCTGGCATAACACCCAGCTTGGTTTGGGTGGCAGCTGGG

AGAACTTCTCTCCCAGCCCTGCAACTCTTACGCTCTGGTTCAGCTGCCTC

TGCACCCCTCCCACCCCCAGCACACACACAAGTTGGCCCCCAGCTGCGC

CTGACATTGAGCCAGTGGACTCTGTGTCTGAAGGGGCGTGGCCACACCT

CCTAGACCACGCCCACCACTTAGACCACGCCCACCTCCTGACCGCGTTCC

TCAGCCTCCTCTCCTAGGTCCCTCCGCCCGACAGTTGTGCTTTGTTGTGG

TTGCAGCTGTTTTCGTGTCATGTATAGTAGTAGAAATGGAAATCATTGTA

CTGTAAAAGCCTAGTGACTCCCTCCTTGGCCAGGCCCTCACCCAGTTCAG

ATCCACGGCCTCCACCCGGGACGCCTTCCTCCTCTGCTCCCAAACAGGGT

TTCCGTGGCCTGTTTGCAGCTAGACATTGACCTCCGCCATTGAGCTCCAC

GGTTTACAGACAATTGCACAAGCGTGGGGTGGGCAGGCCAGGACTGCTTT

TTTTTAATGCTCCCATTTCACAGAGGATACCACCGAGACTCGGAGGGGAC

ACGATGAGCACCAGGCCCCACCTTTGTCCCCTAGCAAATTCAGGGTACAG

CTCCACCTAGAACCAGGCTGCCCTCTACTGTGCTCGTTCCTCAAGCATTT

ATTAAGCACCTACTGGGTGCTGGGTTCACTGTGTCCTAGGAAACCAAGAG

GGTCCCCAGTCCTGGCCTCTGCCCGCCCCTGCTGCCCCACCACCTTCTGC

ACACACAGCGGTGGGGAGGCGGGGAGGAGCAGCTGGGACCCAGAACTGAG

CCTGGGAGGGATCCGACAGAAAAGCTCAGGGCGGGTCTTCTCCTTGTGCC

CGGGATTGGGCTATGCTGGGTACCACCATGTACTCAGGCATGGTGGGTTT

TGAACCCATAAACCAAAGGCCCTTGTCATCAGCTCTTAACAAGTATATTT

TGTATTTTAATCTCTCTAAACATATTGAAGTTTTAGGGCCCTAAGGAACC

TTAGTGATCTTCTATTGGGTCTTTCTGAGGTTCAGAGAGGGTAAGTAACT

TCCTCCAGGTCACACAGCAAGTCTGTGGGTGGCAGAAGCAAGCTAGCGCT

GGGCATTCAGTACATACCACGATGTGCTCCCTCTCTTGATGCTTGGCCCC

TGGGGCCTTCAGGGCTTTGGGACATCTTGTCCTCAACCCTCTCCCTAGAT

CAGTCTGTGAGGGTCCCTGTAGATATTGTGTACACCATGCCCATGTATAT

ACAAGTACACACAGATGTACACACAGATGTACACATGCTCCAGCCCCAGC

TCTGCATACCTGCACCTGCACCCCAGCCTTGGCCCCTGCCTGCGTCTGTG

CTCAAAGCAGCAGCTCCAACCCTGCCTCTGTCCCCTTCCCCACCCACTGC

CTGAGCCTTCTGAGCAGACCAGGTACCTTGGCTGCACCGGTGTGTGGCCC

GCTCTCACCCAGGCACAGCCCCGCCACCATGGATCTCCGTGTACACTATC

AATAAAGTGGGTTTGTTACAAAAAAAAAAAAAAAAAAAAAAAAAAAAAAA

AAAAAAAAAAAAAAAAAAAAAAAAAAAAAAAAAAAAAAAAAAAAAAAAA.

In certain embodiments, the Rhes is at least 90% identical to the protein encoded by SEQ ID NO:3 (e.g., 90%, 91%, 92%, 93%, 94%, 95%, 96%, 97%, 98%, 99% or 100% identical to the protein encoded by SEQ ID NO:3). In certain embodiments, the Rhes is at least 90% identical to the protein encoded by the Rhes coding sequence, SEQ ID NO:4 (e.g., 90%, 91%, 92%, 93%, 94%, 95%, 96%, 97%, 98%, 99% or 100% identical to the protein encoded by SEQ ID NO:4), indicated in bold above. In certain embodiments, the nucleic acid encoding Rheb is a fragment or variant of SEQ ID NO: 3 or 4, or has substantial identity to SEQ ID NO: 3 or 4.

In certain embodiments, the therapeutic agent is contained in a viral vector. In certain embodiments, the viral vector is an adeno-associated viral (AAV) vector.

Expression Cassettes and Vectors

The present invention also provides an expression cassette comprising a sequence encoding Rhes or Rheb.

In certain embodiments, the expression cassette further contains a promoter. In certain embodiments, the promoter is a regulatable promoter. In certain embodiments, the promoter is a constitutive promoter. In certain embodiments, the promoter is a PGK, CMV or RSV promoter.

The present invention provides a vector containing the expression cassette described above. In certain embodiments, the vector is a viral vector. In certain embodiments, the viral vector is an adenoviral, lentiviral, adeno-associated viral (AAV), poliovirus, HSV, or murine Maloney-based viral vector.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

Adeno Associated Virus (AAV)

Adeno associated virus (AAV) is a small nonpathogenic virus of the parvoviridae family. AAV is distinct from the other members of this family by its dependence upon a helper virus for replication. In the absence of a helper virus, AAV may integrate in a locus specific manner into the q arm of chromosome 19. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To date, numerous serologically distinct AAVs have been identified, and more than a dozen have been isolated from humans or primates. The genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Furthermore, two of the Rep proteins have been associated with the preferential integration of AAV genomes into a region of the q arm of human chromosome 19. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV virion is a non-enveloped, icosohedral particle approximately 25 nm in diameter, consisting of three related proteins referred to as VP1, VP2 and VP3. The right ORF encodes the capsid proteins VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles. Mutations within the VP3 coding region result in the failure to produce any single-stranded progeny DNA or infectious particles. An AAV particle is a viral particle comprising an AAV capsid protein. An AAV capsid polypeptide can encode the entire VP1, VP2 and VP3 polypeptide. The particle can be a particle comprising AAV2 and other AAV capsid proteins (i.e., a chimeric protein, such as AAV1 and AAV2). Variations in the amino acid sequence of the AAV2 capsid protein are contemplated herein, as long as the resulting viral particle comprises the AAV2 capsid remains antigenically or immunologically distinct from AAV1, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinct from AAV1.

An AAV2 particle is a viral particle comprising an AAV2 capsid protein. An AAV2 capsid polypeptide encoding the entire VP1, VP2, and VP3 polypeptide can overall have at least about 63% homology (or identity) to the polypeptide having the amino acid sequence encoded by nucleotides set forth in NC_001401 (nucleotide sequence encoding AAV2 capsid protein). The capsid protein can have about 70% homology, about 75% homology, 80% homology, 85% homology, 90% homology, 95% homology, 98% homology, 99% homology, or even 100% homology to the protein encoded by the nucleotide sequence set forth in NC_001401. The capsid protein can have about 70% identity, about 75% identity, 80% identity, 85% identity, 90% identity, 95% identity, 98% identity, 99% identity, or even 100% identity to the protein encoded by the nucleotide sequence set forth in NC_001401. The particle can be a particle comprising another AAV and AAV2 capsid protein, i.e., a chimeric protein. Variations in the amino acid sequence of the AAV2 capsid protein are contemplated herein, as long as the resulting viral particle comprising the AAV2 capsid remains antigenically or immunologically distinct from AAV4, as can be routinely determined by standard methods. Specifically, for example, ELISA and Western blots can be used to determine whether a viral particle is antigenically or immunologically distinct from AAV1. Furthermore, the AAV2 viral particle preferably retains tissue tropism distinction from AAV1, such as that exemplified in the examples herein, though an AAV2 chimeric particle comprising at least one AAV2 coat protein may have a different tissue tropism from that of an AAV2 particle consisting only of AAV2 coat proteins.

In certain embodiments, the invention further provides an AAV2 particle containing, i.e., encapsidating, a vector comprising a pair of AAV2 inverted terminal repeats. The nucleotide sequence of AAV2 ITRs is known in the art. Furthermore, the particle can be a particle comprising both AAV1 and AAV2 capsid protein, i.e., a chimeric protein. Moreover, the particle can be a particle encapsidating a vector comprising a pair of AAV inverted terminal repeats from other AAVs (e.g., AAV1-AAV9 and AAVrh10). The vector encapsidated in the particle can further comprise an exogenous nucleic acid inserted between the inverted terminal repeats.

The following features of AAV have made it an attractive vector for gene transfer. AAV vectors have been shown in vitro to stably integrate into the cellular genome; possess a broad host range; transduce both dividing and non-dividing cells in vitro and in vivo and maintain high levels of expression of the transduced genes. Viral particles are heat stable, resistant to solvents, detergents, changes in pH, temperature, and can be concentrated on CsCl gradients or by other means. The present invention provides methods of administering AAV particles, recombinant AAV vectors, and recombinant AAV virions. For example, an AAV2 particle is a viral particle comprising an AAV2 capsid protein, or an AAV1 particle is a viral particle comprising an AAV1 capsid protein. A recombinant AAV2 vector is a nucleic acid construct that comprises at least one unique nucleic acid of AAV2. A recombinant AAV2 virion is a particle containing a recombinant AAV2 vector. To be considered within the term "AAV2 ITRs" the nucleotide sequence must retain one or both features described herein that distinguish the AAV2 ITR from the AAV1 ITR: (1) three (rather than four as in AAV1) "GAGC" repeats and (2) in the AAV2 ITR Rep binding site the fourth nucleotide in the first two "GAGC" repeats is a C rather than a T.

The promoter to drive expression of the protein or the sequence encoding another agent to be delivered can be any desired promoter, selected by known considerations, such as the level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc. Additional examples include regulated promoters.

The AAV vector can further comprise an exogenous (heterologous) nucleic acid functionally linked to the promoter. By "heterologous nucleic acid" is meant that any heterologous or exogenous nucleic acid can be inserted into the vector for transfer into a cell, tissue or organism. The nucleic acid can encode a polypeptide or protein or an antisense RNA, for example. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences. The nucleic acid can encode more than one gene product, limited only by the size of nucleic acid that can be packaged.

In certain embodiments of the present invention, the heterologous nucleic acid can encode beneficial proteins that replace missing or defective proteins required by the subject into which the vector in transferred, such as Rheb or Rhes.

An AAV1 particle is a viral particle comprising an AAV1 capsid protein. Variations in the amino acid sequence of the AAV1 capsid protein are contemplated herein, as long as the resulting viral particle comprising the AAV1 capsid remains antigenically or immunologically distinct from other AAV capsids, as can be routinely determined by standard methods. Specifically, for example, ELISA and Western blots can be used to determine whether a viral particle is antigenically or immunologically distinct from other AAV serotypes.

The term "polypeptide" as used herein refers to a polymer of amino acids and includes full-length proteins and fragments thereof. Thus, "protein" and "polypeptide" are often used interchangeably herein. Substitutions can be selected by known parameters to be neutral. As will be appreciated by those skilled in the art, the invention also includes those polypeptides having slight variations in amino acid sequences or other properties. Such variations may arise naturally as allelic variations (e.g. due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. These modifications can result in changes in the amino acid sequence, provide silent mutations, modify a restriction site, or provide other specific mutations.

The present method provides a method of delivering a nucleic acid to a cell comprising administering to the cell an AAV particle containing a vector comprising the nucleic acid inserted between a pair of AAV inverted terminal repeats, thereby delivering the nucleic acid to the cell. Administration to the cell can be accomplished by any means, including simply contacting the particle, optionally contained in a desired liquid such as tissue culture medium, or a buffered saline solution, with the cells. The particle can be allowed to remain in contact with the cells for any desired length of time, and typically the particle is administered and allowed to remain indefinitely. For such in vitro methods, the virus can be administered to the cell by standard viral transduction methods, as known in the art and as exemplified herein. Titers of virus to administer can vary, particularly depending upon the cell type, but will be typical of that used for AAV transduction in general. Additionally the titers used to transduce the particular cells in the present examples can be utilized. The cells can include any desired cell in humans as well as other large (non-rodent) mammals, such as primates, horse, sheep, goat, pig, and dog.

More specifically, the present invention provides a method of delivering a nucleic acid to a cell in the brain, particularly medium spiny neurons, comprising the nucleic acid inserted between a pair of AAV inverted terminal repeats, thereby delivering the nucleic acid to the cell.

The present invention further provides a method of delivering a nucleic acid to a cell in a subject comprising administering to the subject an AAV particle comprising the nucleic acid inserted between a pair of AAV inverted terminal repeats, thereby delivering the nucleic acid to a cell in the subject.

Also provided is a method of delivering a nucleic acid to a brain cell, such as a neuron in the striatum or cortex in a subject comprising administering to the subject an AAV particle comprising the nucleic acid inserted between a pair of AAV inverted terminal repeats, thereby delivering the nucleic acid to the neuron or other cell in the subject.

Certain embodiments of the present disclosure provide a cell comprising a viral vector as described herein.

AAV Vectors

In one embodiment, a viral vector of the disclosure is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-9 and AAVrh10. For example, serotype AAV2 is used to refer to an AAV which contains capsid proteins encoded from the cap gene of AAV2 and a genome containing 5' and 3' ITR sequences from the same AAV2 serotype. As used herein, for example, rAAV1 may be used to refer an AAV having both capsid proteins and 5'-3' ITRs from the same serotype or it may refer to an AAV having capsid proteins from one serotype and 5'-3' ITRs from a different AAV serotype, e.g., capsid from AAV serotype 2 and ITRs from AAV serotype 5. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from AAV2. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Such promoter sequences are commercially available from, e.g., Stratagene (San Diego, Calif.).

In one embodiment, both heterologous promoters and other control elements, such as CNS-specific and inducible promoters, enhancers and the like, will be of particular use. Examples of heterologous promoters include the CMV promoter. Examples of CNS-specific promoters include those isolated from the genes from myelin basic protein (MBP), glial fibrillary acid protein (GFAP), and neuron specific enolase (NSE). Examples of inducible promoters include DNA responsive elements for ecdysone, tetracycline, hypoxia and aufin.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques welt known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM MgCl$_2$, 10 mM DTT, 33 µg/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs.

Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct micro-injection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome.

In one embodiment, AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products.

Methods of delivery of viral vectors include injecting the AAV into the subject. Generally, rAAV virions may be introduced into cells of the CNS using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with CNS cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

It should be understood that more than one transgene could be expressed by the delivered viral vector. Alternatively, separate vectors, each expressing one or more different transgenes, can also be delivered to the subject as described herein. Furthermore, it is also intended that the viral vectors delivered by the methods of the present disclosure be combined with other suitable compositions and therapies.

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

In certain embodiments, the rAAV is administered at a dose of about 0.3-2 ml of $1 \times 10^5$-$1 \times 10^{16}$ vg/ml. In certain embodiments, the rAAV is administered at a dose of about 1-3 ml of $1 \times 10^7$-$1 \times 10^{14}$ vg/ml. In certain embodiments, the rAAV is administered at a dose of about 1-2 ml of $1 \times 10^8$-$1 \times 10^{13}$ vg/ml.

Formulations containing the rAAV particles will contain an effective amount of the rAAV particles in a vehicle, the effective amount being readily determined by one skilled in the art. The rAAV particles may typically range from about 1% to about 95% (w/w) of the composition, or even higher or lower if appropriate. The quantity to be administered depends upon factors such as the age, weight and physical condition of the animal or the human subject considered for treatment. Effective dosages can be established by one of ordinary skill in the art through routine trials establishing dose response curves. The subject is treated by administration of the rAAV particles in one or more doses. Multiple doses may be administered as is required to maintain adequate enzyme activity.

Vehicles including water, aqueous saline, artificial CSF, or other known substances can be employed with the subject invention. To prepare a formulation, the purified composition can be isolated, lyophilized and stabilized. The composition may then be adjusted to an appropriate concentration, optionally combined with an anti-inflammatory agent, and packaged for use.

The present invention provides a method of increasing the level of a target protein in a cell by introducing a protein, or nucleic acid molecule encoding a protein described above into a cell in an amount sufficient to increase the level of the target protein in the cell. In certain embodiments, the accumulation of target protein is increased by at least 10%. The accumulation of target protein is increased by at least 10%, 20%, 30%, 40%, 50%, 60%, 70%, 80%, 90% 95%, or 99%.

Nucleic Acids Encoding Therapeutic Agents

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein. In certain embodiments, the fragment or portion is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of Rheb or Rhes).

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence. In certain embodiments, the variant is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity of the wildtype Rhes or Rheb).

"Conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

The term "substantial identity" in the context of a peptide indicates that a peptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

Methods for Introducing Genetic Material into Cells

The exogenous genetic material (e.g., a cDNA encoding one or more therapeutic proteins) is introduced into the cell in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-faciliated microparticle bombardment. Strontium phosphate DNA co-precipitation is another possible transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions, which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

Methods of Treatment

Certain embodiments of the present disclosure provide a method of treating a disease in a mammal comprising administering a protein or vector encoding a protein as described herein to the mammal.

In certain embodiments, the mammal is human.

Certain embodiments of the present disclosure provide a use of a protein or vector encoding a protein as described herein to prepare a medicament useful for treating Huntington's disease in a mammal.

The present disclosure also provides a mammalian cell containing a vector described herein. The cell may be human, and may be from brain.

Certain aspects of the disclosure relate to polynucleotides, polypeptides, vectors, and genetically engineered cells (modified in vivo), and the use of them. In particular, the disclosure relates to a method for gene or protein therapy that is capable of both systemic delivery of a therapeutically effective dose of the therapeutic agent.

According to one aspect, a cell expression system for expressing a therapeutic agent in a mammalian recipient is provided. The expression system (also referred to herein as a "genetically modified cell") comprises a cell and an expression vector for expressing the therapeutic agent. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector.

The expression vector further includes a promoter for controlling transcription of the heterologous gene. The promoter may be an inducible promoter (described below). The expression system is suitable for administration to the mammalian recipient. The expression system may comprise a plurality of non-immortalized genetically modified cells, each cell containing at least one recombinant gene encoding at least one therapeutic agent.

The cell expression system is formed in vivo. According to yet another aspect, a method for treating a mammalian recipient in vivo is provided. The method includes introducing an expression vector for expressing a heterologous gene product into a cell of the patient in situ, such as via intravenous administration. To form the expression system in vivo, an expression vector for expressing the therapeutic agent is introduced in vivo into the mammalian recipient i.v., where the vector migrates via the vasculature to the brain.

According to yet another aspect, a method for treating a mammalian recipient in vivo is provided. The method includes introducing the target protein into the patient in vivo.

The expression vector for expressing the heterologous gene may include an inducible promoter for controlling transcription of the heterologous gene product. Accordingly, delivery of the therapeutic agent in situ is controlled by exposing the cell in situ to conditions, which induce transcription of the heterologous gene.

A "variant" of one of the polypeptides (e.g., Rhes or Rheb) is a polypeptide that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which, retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 50%, at least about 80%, or even at least about 90% but less than 100%, contiguous amino acid sequence homology or identity to the amino acid sequence of a corresponding native protein.

The amino acid sequence of the variant polypeptide corresponds essentially to the native polypeptide's amino acid sequence. As used herein "correspond essentially to" refers to a polypeptide sequence that will elicit a biological response substantially the same as the response generated by the native protein. Such a response may be at least 60% of the level generated by the native protein, and may even be at least 80% of the level generated by native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The variant protein may be expressed from an isolated DNA sequence encoding the variant protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence.

The present disclosure provides methods of treating a disease in a mammal by administering an expression vector to a cell or patient. For the gene therapy methods, a person having ordinary skill in the art of molecular biology and gene therapy would be able to determine, without undue experimentation, the appropriate dosages and routes of administration of the expression vector used in the novel methods of the present disclosure.

According to one embodiment, the cells are transformed or otherwise genetically modified in vivo. The cells from the mammalian recipient are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into anti-sense RNA, as well as a "heterologous gene" (i.e., a gene encoding a protein which is not expressed or is expressed at biologically insignificant levels in a naturally-occurring cell of the same type).

In summary, the term "therapeutic agent" includes, but is not limited to, agents associated with the conditions listed above, as well as their functional equivalents. As used herein, the term "functional equivalent" refers to a molecule (e.g., a peptide or protein) that has the same or an improved beneficial effect on the mammalian recipient as the therapeutic agent of which is it deemed a functional equivalent.

The above-disclosed therapeutic agents and conditions amenable to gene replacement therapy are merely illustrative and are not intended to limit the scope of the instant disclosure. The selection of a suitable therapeutic agent for treating a known condition is deemed to be within the scope of one of ordinary skill of the art without undue experimentation.

Dosages, Formulations and Routes of Administration of the Agents of the Invention The agents of the invention are administered so as to result in a reduction in at least one symptom associated with Huntington's disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The present invention envisions treating Huntington's disease by the administration of an agent, e.g., Rhes or Rheb, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. For example, the therapeutic agent may be directly injected into the brain.

Alternatively the therapeutic agent may be introduced intrathecally for brain and spinal cord conditions. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 and water.

The invention will now be illustrated by the following non-limiting Example.

Example 1

Reinstating Aberrant mTORC1 Activity in Huntington's Disease Mice Improves Disease Phenotypes Mechanistic target of rapamycin (mTOR) is a serine-threonine kinase that integrates signals to regulate cell growth and metabolism (Laplante and Sabatini, 2012). mTOR forms 2 distinct complexes, mTORC1 and mTORC2. Under nutrient-rich conditions, mTORC1 is activated and promotes protein translation and cell growth. In contrast, nutrient withdrawal inactivates mTORC1 and initiates macroautophagy (hereafter referred to as autophagy) as a cell survival mechanism. mTORC1 positively controls mitochondrial biogenesis (Cunningham et al., 2007) and regulates lipid homeostasis by controlling cholesterol synthesis (Peterson et al., 2011; Porstmann et al., 2008). Moreover, in the brain, mTORC1 promotes myelination, axon growth, and regeneration (Kim et al., 2012; Park et al., 2008; Sun et al., 2011), and genetic deletion of the Ras homologue enriched in brain (Rheb), a key activator of mTORC1, causes decreased cortical thickness and defective myelination (Zou et al., 2011).

In the striatum Rhes (Ras homolog enriched in the striatum) serves as a key activator of mTORC1 (Subramaniam et al., 2012). Genetic knockout of Rhes reduces mTORC1 activity, and attenuates adverse responses to L-DOPA induced dyskinesia (Subramaniam et al., 2012). Additionally, Rhes facilitates SUMOylation (Subramaniam et al., 2009), a process implicated in HD pathogenesis (Steffan et al., 2004). In vitro, Rhes promotes SUMOylation of mHTT to induce cytotoxicity (Subramaniam et al., 2009), and reducing exogenously added Rhes with siRNAs increased survival of cells transfected with mHTT fragments (Lu and Palacino, 2013; Seredenina et al., 2011). In vivo, genetic ablation of Rhes protects against neurotoxin-induced 4 striatal lesions (Mealer et al., 2013), and transiently delays motor symptom onset in R6/1 HD mice (Baiamonte et al., 2013). Because Rhes is highly expressed in the striatum (Spano et al., 2004), it has been proposed that Rhes-mHTT interactions may underlie the prominent striatal degeneration in HD.

However, other data call to question a pathogenic role for Rhes in HD. Rhes levels are reduced in HD patient caudate nucleus (Hodges et al., 2006), and Rhes ablation in R6/1 HD models does not prevent brain degeneration (Baiamonte et al., 2013). Furthermore, Rhes KO mice develop brain atrophy and behavioral abnormalities resembling those found in HD mice (Baiamonte et al., 2013; Spano et al., 2004). In addition, Rhes promotes autophagy (Mealer et al., 2014), a well-established protective mechanism in HD. Therefore, given the critical function of Rhes in mediating striatal mTORC1 signaling, we hypothesized that a concomitant loss of Rhes and mTORC1 activity contributes to the early striatal pathology in HD, and that enhancing mTORC1 function, through up-regulation of Rheb or Rhes, would be neuroprotective.

To test this hypothesis we acutely modulated Rhes and mTORC1 activity in adult striata of HD transgenic mice. We found beneficial effects with mTORC1 activation, including improved mHTT-associated metabolic phenotypes and reversal of striatal atrophy. Consistently, restoring mTORC1 activity or Rhes levels in vivo was protective. Further, we showed that the neuroprotective property of Rhes is dependent on its GTPase activity, which is required for activating mTORC1 but independent of SUMOylation related activity. Collectively, these data suggest that impaired Rhes/mTORC1 activity is relevant to the notable striatal pathogenesis in HD and suggest that impaired mTORC1 function may represent a fundamental mechanism underlying the complex disease phenotypes in HD.

Results mTORC1 Activity is Reduced in the Striatum of HD

Figure 1B:
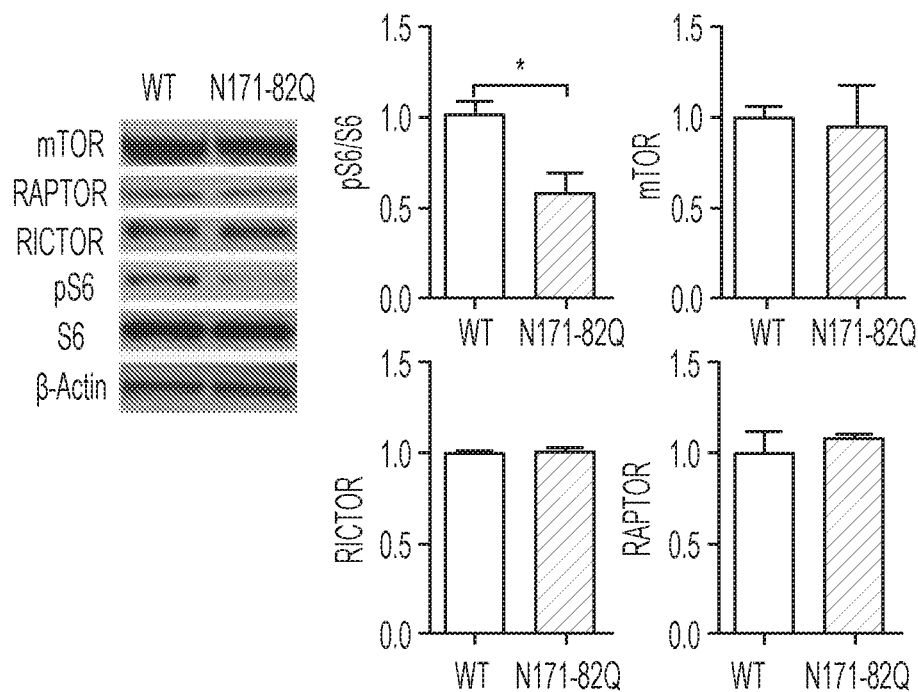
Figure 2A:
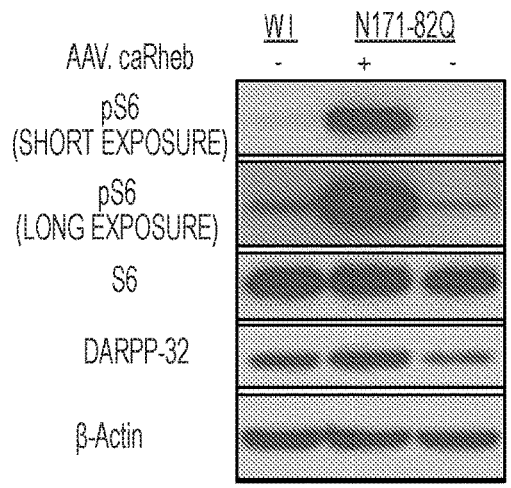
FIGS. 2A-2G. Activation of mTORC1 pathway corrects metabolism-related deficits in HD mice. (A) Western blot shows increased pS6 and DARPP-32 immunoreactivity in N171-82Q mice treated with unilateral injection of AAV.caRheb, compared to untreated. Mice were injected at 7 weeks of age and striatal lysates harvested at 10 weeks of age. Right, densitometry quantification of DARPP-32 immunoreactivity (N=4 mice per group; *P<0.05, One-way ANOVA with Tukey's post-hoc test). (B) RT-qPCR analysis of PGC1-α in striatal homogenates from 10-week-old N171-82Q mice treated with unilateral injection of AAV.caRheb at 7 weeks of age. Striatal lysates from uninjected contralateral hemispheres served as internal controls (N=8 per group). (C-G) RT-qPCR analysis of ROS detoxifying genes in striatal homogenates from 10-week-old N171-82Q and WT mice after unilateral injection of AAV.caRheb at 7 weeks of age. Lysates from uninjected contralateral hemispheres served as internal controls (N=8 per group). All genes were normalized to endogenous β-actin. Data represent mean+SEM. C=Control. *P<0.05, P<0.01, *P<0.001, Student's t-test.
Figure 2B:
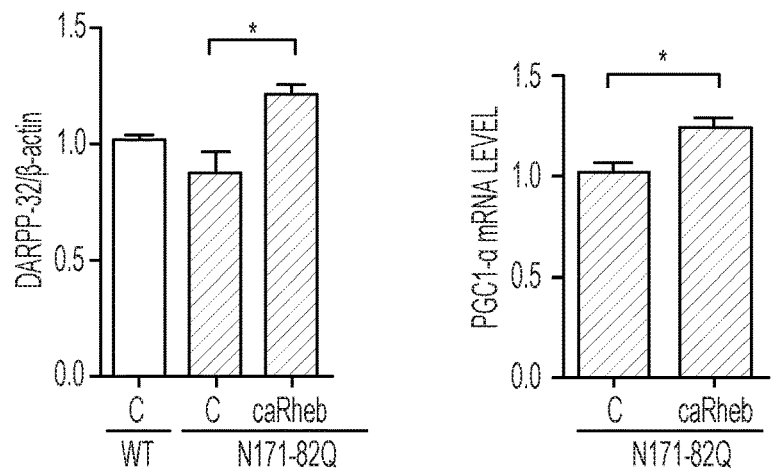
Figures 2C, 2D:
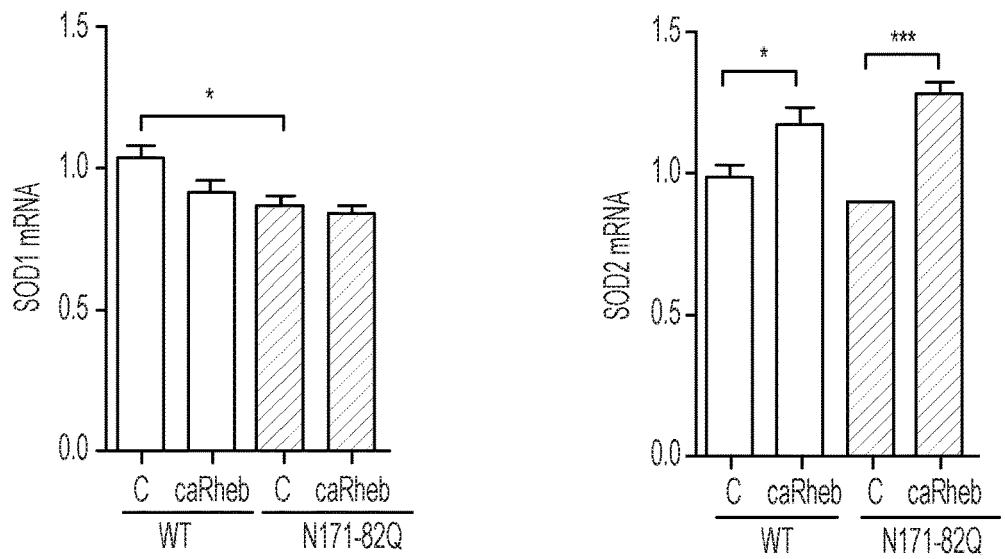
Figure 2E:
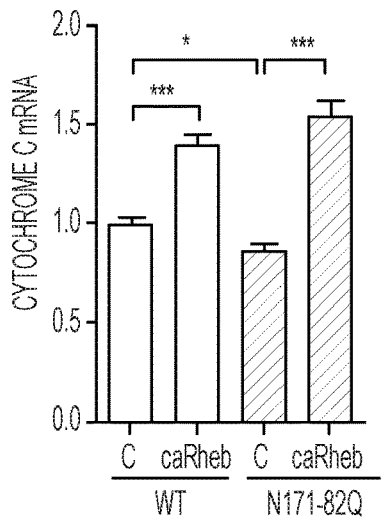
Figure 2F:
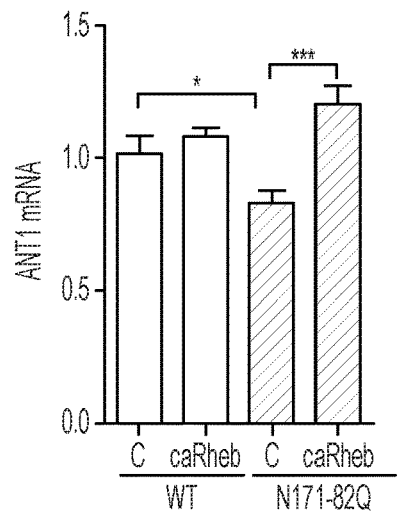
Figure 2G:
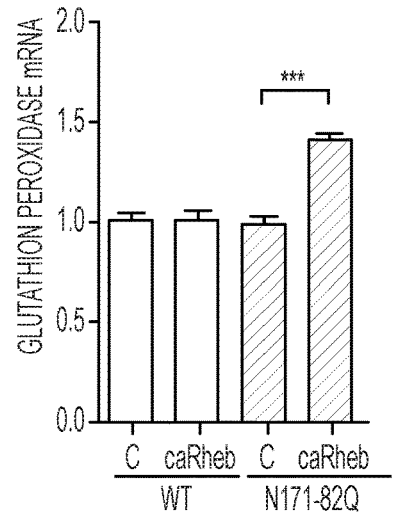
Figure 9A:
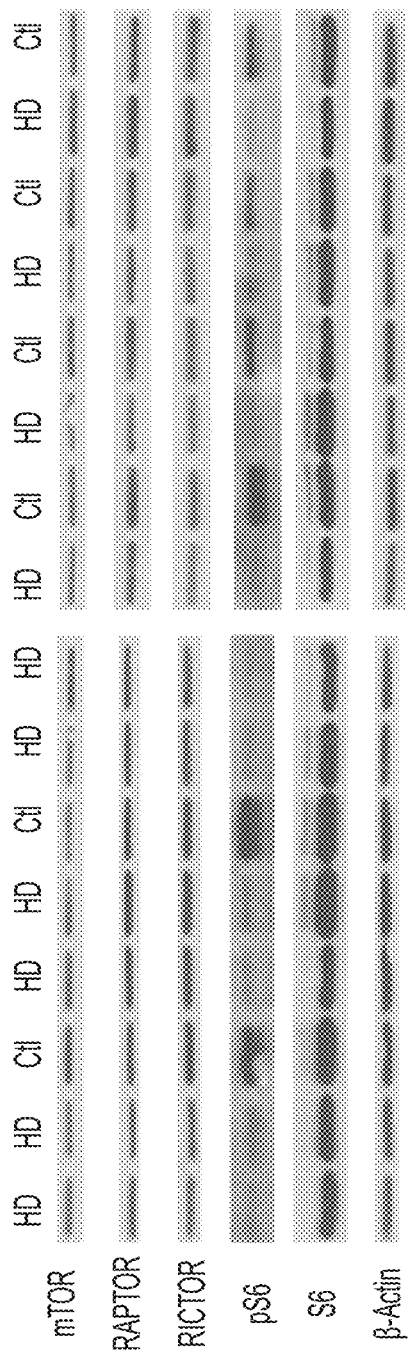
FIGS. 9A-9B. mTORC1 activity is reduced in HD human and mouse striatum. (A) Western blot demonstrates reduced mTORC1 activity (pS6) in the striatum of patients with HD (N=10) compared to unaffected individuals (N=6). β-actin was used as a loading control (related to FIG. 1A). (B) Biochemical analysis of endogenous mTORC1 activity (pS6) from 14-week-old N171-82Q and WT mouse striatal lysates. β-actin was used as a loading control. Densitometry analysis revealed reduced pS6 level in 14-week-old N171-82Q mice (N=5) compared to age- and sex-matched WT littermates (N=4). Data represent mean+SEM.*P<0.05, Student's t-test.
Figure 9B:
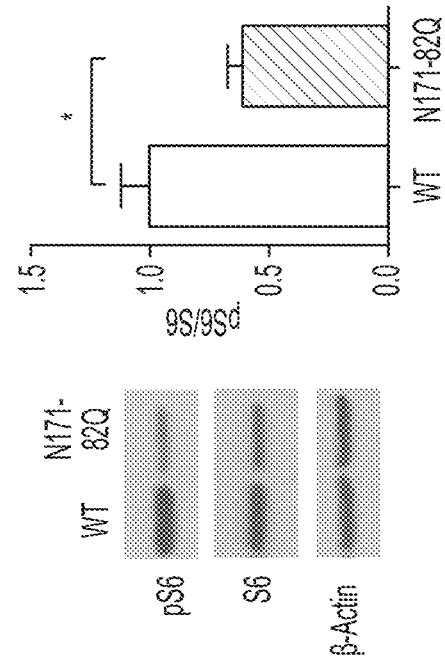
Figure 10H:
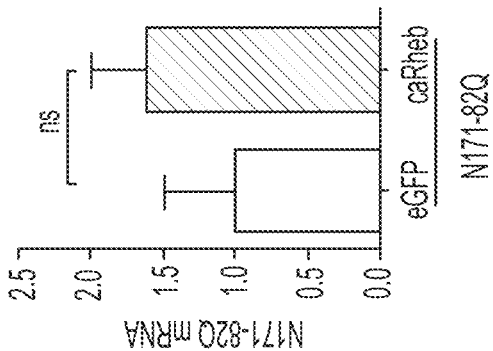
Figure 10G:
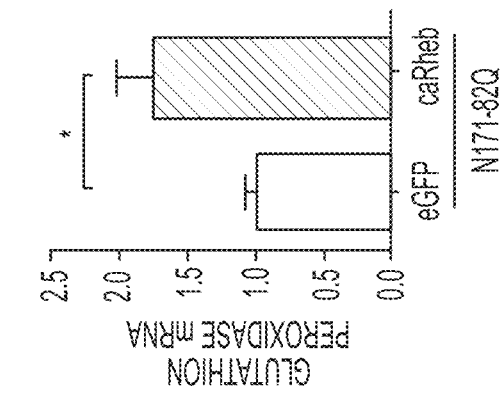
Figure 10F:
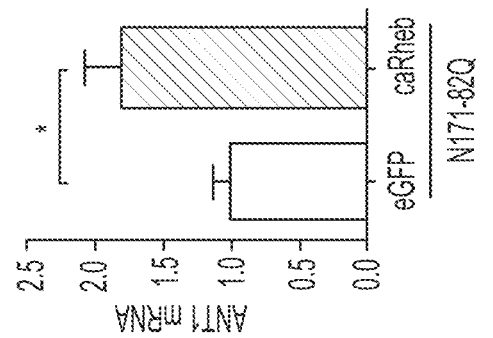
Figure 10E:
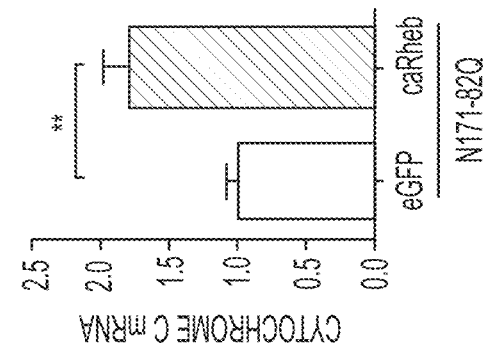
Figure 11A:
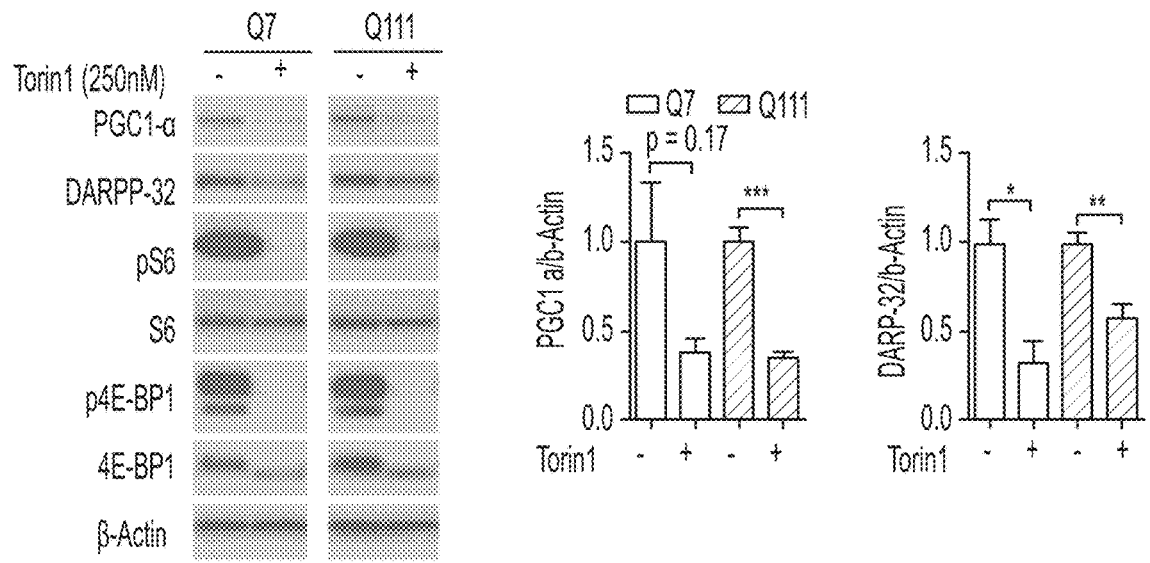
FIGS. 11A-11F. A,B. Torin1 inhibits metabolism gene expression genes in striatal cell model of HD. Q7 and Q111 striatal cells grown in normal serum condition were treated with Torin1 or DMSO (control). Total cell extracts were obtained 24 hrs later. (A) Biochemical assessment shows reduced mTORC1 activity (pS6 and p4E-BP1), PGC1-α, and DARPP-32 expression in Q7 and Q111 cells with Torin1 treatment. (B) A representative western blot for CREB and its coactivator, TORC1 24 hours after Torin1 treatment. Densitometry analyses show Torin1 suppressed TORC1 and CREB levels in Q7 and Q111 cells. Values are percentage of vehicle-treated controls+SEM of four independent experiments (N=4 per treatment groups). Endogenous β-actin was the loading control.*P<0.05; **P<0.01, Student's t-test. C-F. mTOR alters cholesterol biosynthesis gene expression in AAV.caRheb versus AAV.eGFP treated HD transgenic mouse striata. RT-qPCR analysis of lipogenic genes from striatal homogenates of 13-week-old N171-82Q and WT mice after unilateral injection of AAV.caRheb at 10 weeks of age. Lysates from AAV.eGFP injected contralateral hemispheres served as internal controls (N=4 per group). All genes were normalized to endogenous β-actin. Data represent mean+SEM. C=Control. *P<0.05, **P<0.01, Student's t-test.
Figure 11B:
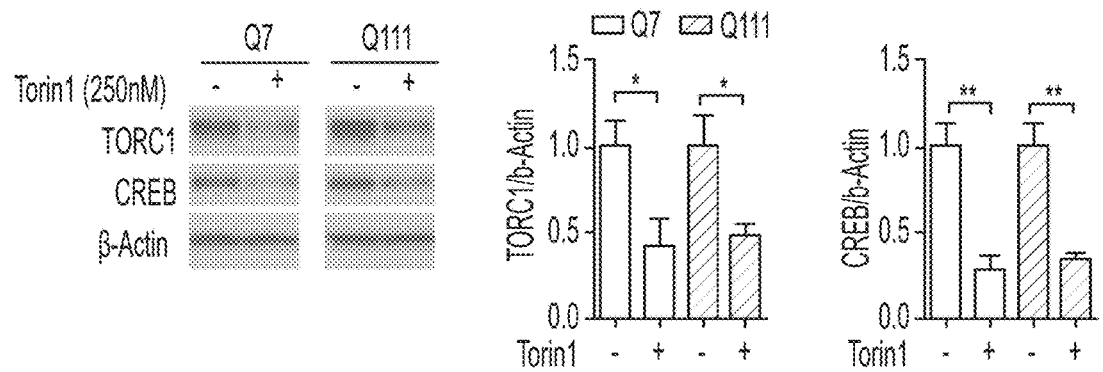
Figure 11C:
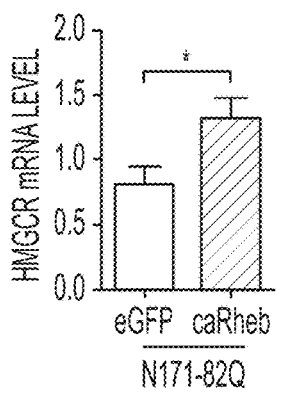
Figure 11D:
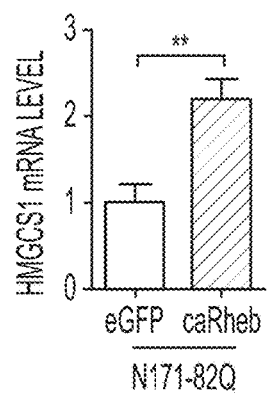
Figure 11E:
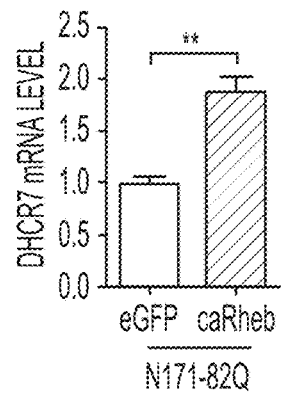
Figure 11F:
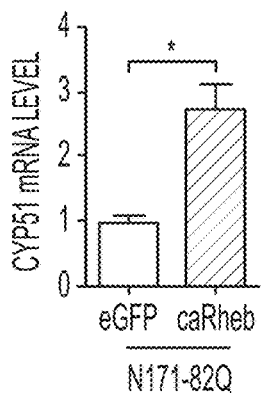

As a first test of our hypothesis, we examined mTORC1 activity in HD brain. We found that mTORC1 activity is reduced in striatal tissues from HD patients and N171-82Q mice as detected by reduced phosphorylation of ribosomal protein S6 (pS6), an established marker of mTORC1 activity (FIG. 1A; FIGS. 9A,B). In HD mice, mTORC1 activity is impaired at 6 weeks of age, prior to the onset of neurological symptoms (FIG. 1B). The reduced mTORC1 activity is not associated with reduced expression of mTOR, or components of the mTOR complex (e.g. Rictor and Raptor)(FIGS. 1A,B; FIG. 9A). We next engineered adeno-associated viruses (AAVs), which transduce striatal neurons (FIG. 10A) (McBride et al., 2008), to express Rheb, a well-established positive regulator of mTORC1 (Laplante and Sabatini, 2012). In this manner, we can acutely enhance mTORC1 activation in vivo. We used a constitutively active Rheb mutant (caRheb; S16H) previously shown to activate mTORC1 signaling in mouse brain (Kim et al., 2012; Zou et al., 2011). Unilateral injection of AAV.caRheb into N171-82Q mouse striata markedly induced mTORC1 activity as indicated by increased pS6 at 3 weeks post-injection (FIG. 2A). Selective reduction of DARPP-32 levels, a fundamental component of dopamine signaling in medium spiny neurons (MSN), is an indicator of pathological progression in HD mouse and human brains (Bibb et al., 2000; Hodges et al., 2006). AAV.caRheb transduction promoted a 33% increase of DARPP-32 levels in N171-82Q mouse striata compared to contralateral uninjected tissue (FIG. 2A). Moreover, AAV.caRheb upregulated expression of the mitochondrial-transcriptional regulator, PPARγ coactivator 1α (PGC1-α) (FIG. 2B), a master regulator of mitochondrial biogenesis that when increased improves mitochondrial function and motor deficits in HD models (Cui et al., 2006; Tsunemi et al., 2012). Consistent with increased mitochondria activity, the levels of reactive oxygen species detoxifying (ROS) genes, SOD2, cyt-c, and ANTI were also increased in AAV.caRheb treated brains (FIGS. 2C-F). Glutathione peroxidase, a recently identified neuroprotective antioxidant enzyme in HD model organisms (Mason et al., 2013), selectively increased in HD brains after caRheb transduction (FIG. 2G). The improved profile could not be explained by an indirect effect of virus injection or downregulation of the mHTT transgene; similar results were obtained when AAV.caRheb injected brains were compared to AAV.eGFP treated brains, and caRheb did not affect mHTT transgene expression (FIGS. 10B-H). We next performed in vitro studies and treated striatal cells that express expanded (Q111) and normal (Q7) Htt (Trettel et al., 2000) with an ATP-competitive inhibitor of mTOR, Torin1. Torin1 potently inhibits TORfunctions including those that are resistant to inhibition by rapamycin (Thoreen et al., 2009). Torin1 treatment reduced pS6 and p-4E-BP1 levels as well as DARPP-32 expression in Q7 and Q111 cells (FIG. 11A). Torin1 also repressed PGC1-α, the PGC1-α-regulated genes cAMP response element-binding protein (CREB), and transducer of regulated CREB 1 (TORC1) (FIGS. 11A, B). Together, our in vitro and in vivo results indicate that mTORC1 regulates PGC1-α and PGC1-α regulated metabolic genes in the setting of WT and mutant HTT alleles.

mTORC1 Controls Lipogenic Gene Expression in HD Brains

Figure 3A:
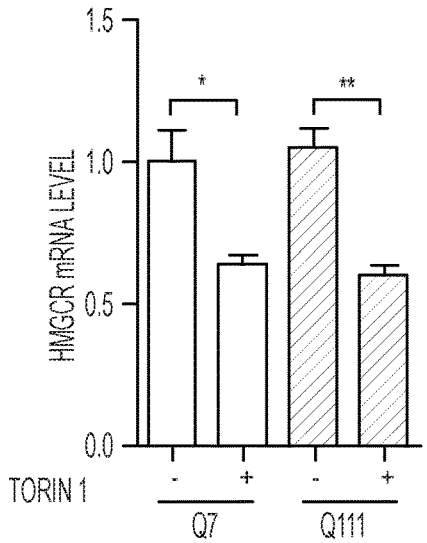
FIGS. 3A-3F. mTOR regulates cholesterol biosynthetic pathway genes in HD mice striata. (A and B) WT (Q7) and mutant (Q111) striatal cells grown in normal media were treated with 250 nM Torin1 or DMSO (control). Total cell extracts were obtained 24 hours after treatment. Gene expression levels of HMGCR and HMGCS1 were normalized to endogenous β-actin. (C-F) RT-qPCR analysis of lipogenic genes from striatal homogenates of 10-week-old N171-82Q and WT mice after unilateral injection of AAV.caRheb at 7 weeks of age. Lysates from uninjected contralateral hemispheres served as internal controls (N=8 per group). All genes were normalized to endogenous β-actin. Data represent mean+SEM. C=Control. *P<0.05, P<0.01, *P<0.001, Student's t-test.
Figure 3B:
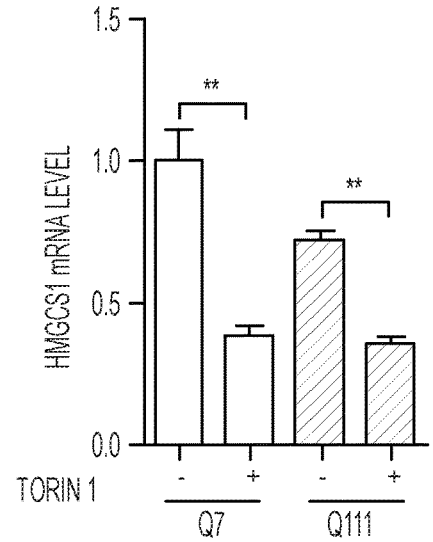
Figure 3C:
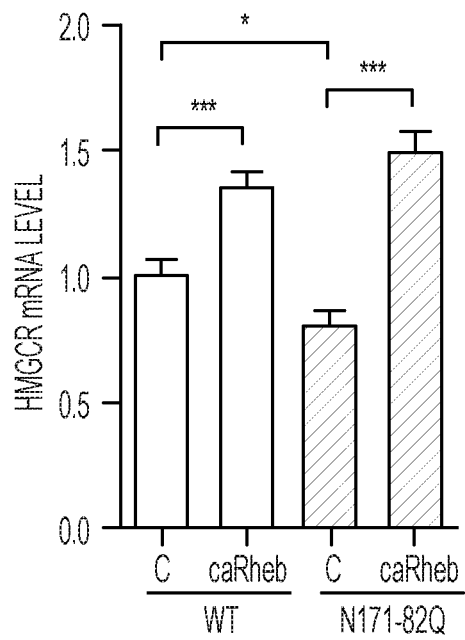
Figure 3D:
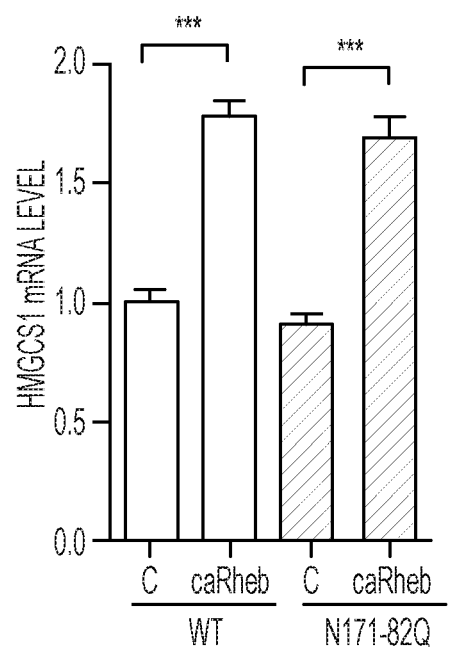
Figure 3E:
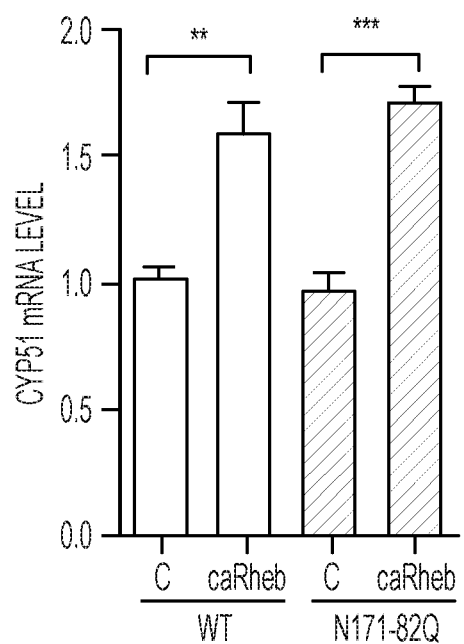
Figure 3F:
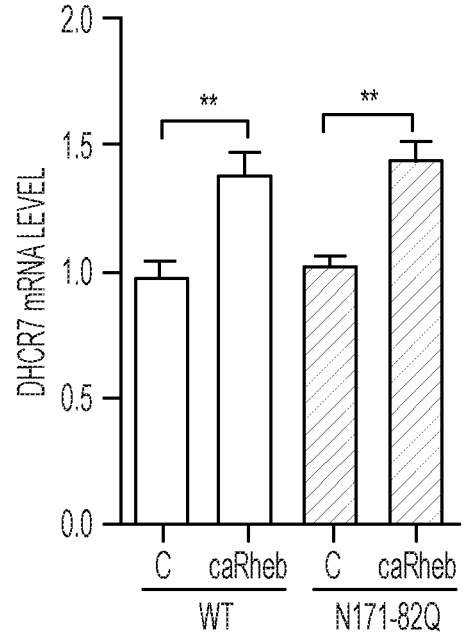

We next determined whether impaired mTORC1 activity underlies other HD-specific metabolic pathway alterations. Aberrant cholesterol biosynthesis has been observed in HD mouse and human brains (Karasinska and Hayden, 2011; Valenza and Cattaneo, 2011). The expression of genes required for lipid biosynthesis is controlled by nuclear transactivation of sterol regulatory element-binding proteins (SREBPs). mHTT has been reported to inhibit nuclear translocation of SREBP in cells and HD mice, which may contribute to dysfunctional cholesterol synthesis (Valenza et al., 2005). mTORC1 also regulates SREBP transactivation (Peterson et al., 2011; Porstmann et al., 2008). To determine if reducing mTORC1 activity alters cholesterol synthesis in the setting of HD, we applied Torin1 to cultured Q7 or Q111 striatal cells. Torin1 reduced expression of the SREBP target genes HMG-CoA reductase (HMGCR), the rate-limiting enzyme in cholesterol synthesis and HMGCS1 in both mutant and normal cell lines (FIGS. 3A, B).

Figure 4A:
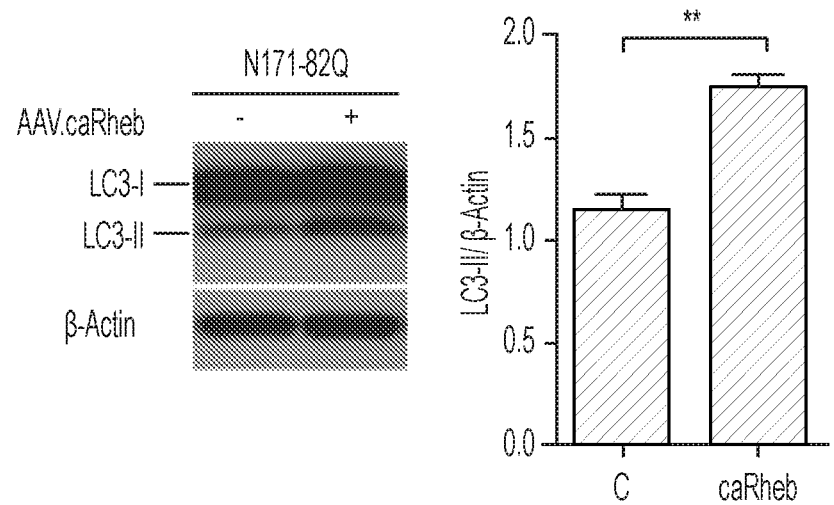
FIGS. 4A-4D. AAV.caRheb increases basal autophagy in N171-82Q mice. (A and B) Biochemical assessment of autophagy (LC3 and Beclin1) in striatal lysates from N171-82Q mice after unilateral injection of AAV.caRheb at 7 weeks of age. Striata were harvested 3 weeks post-injection. Uninjected contralateral striata serve as internal controls (N=6 mice per group). Representative western blots and densitometry analysis revealed increased LC3II and Beclin1 levels in AAV.caRheb-treated N171-82Q mice striata. β-actin was used as a loading control. Data are mean+SEM.**P<0.01; Student's t-test. (C) Left panels: representative photomicrographs of an autophagosome (arrow) and an autolysosome (double arrow). Scale bar is 0.5 μm. Right panel: frequency of autophagosomes and autolysosomes detected in striatal neurons from AAV.eGFP and AAV.caRheb treated N171-82Q mice (3 mice examined per group; 7-10 cells/hemisphere/animal). Ratio indicates number of autophagosome or autolysosome over total number of cells counted. (D) Ultrastructural TEM analysis of striatal sections from N171-82Q mice after AAV.eGFP or AAV.caRheb injections into opposite hemispheres (N=3 mice per group). Left panel: a representative photomicrograph of striatal neurons from control treated striata shows electron-lucent cytoplasm, devoid of endoplasm granular mass and organelles. Right panel: AAV.caRheb treated neurons show normal cytoplasm enriched with organelles and endoplasm granular mass. Scale bar is 5 μm.
Figure 4B:
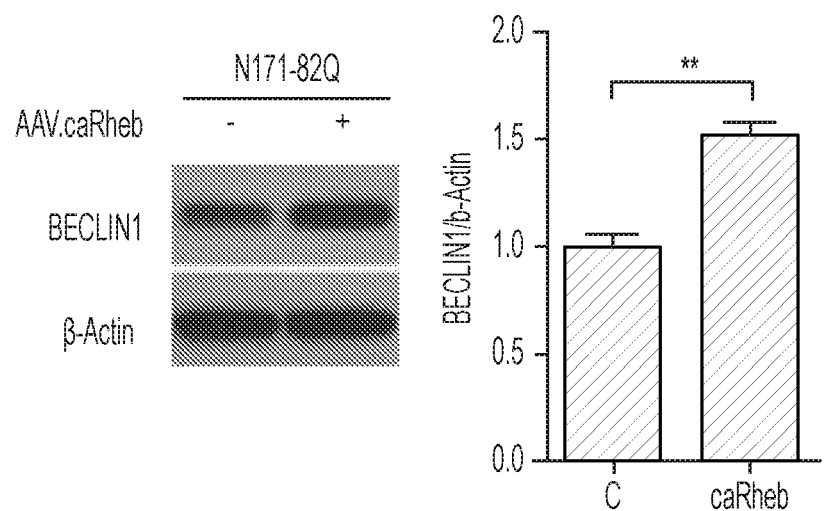
Figure 4C:
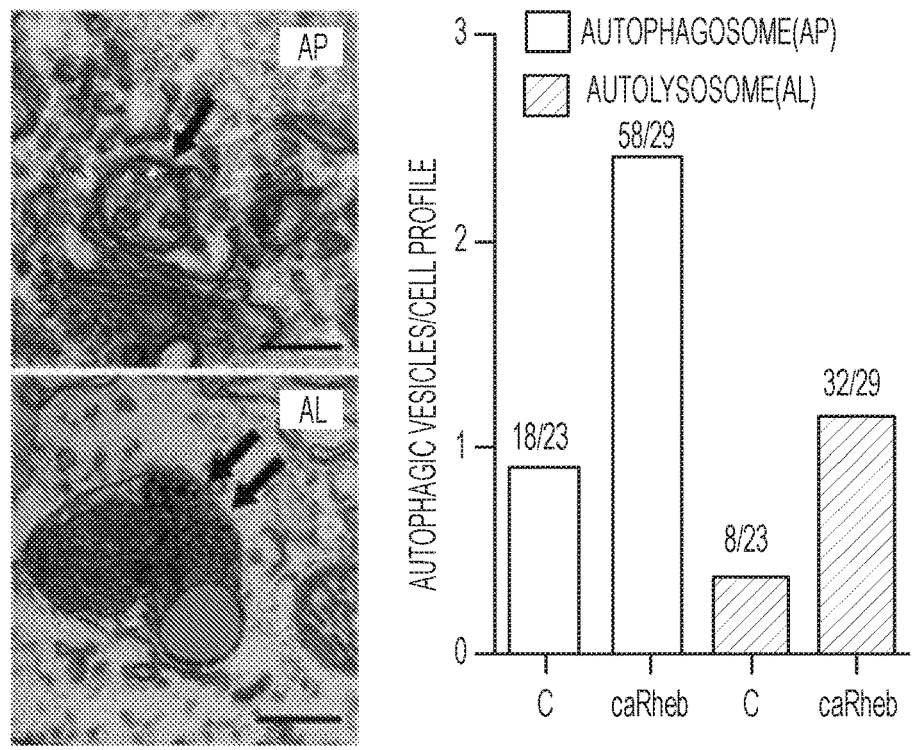
Figure 4D:
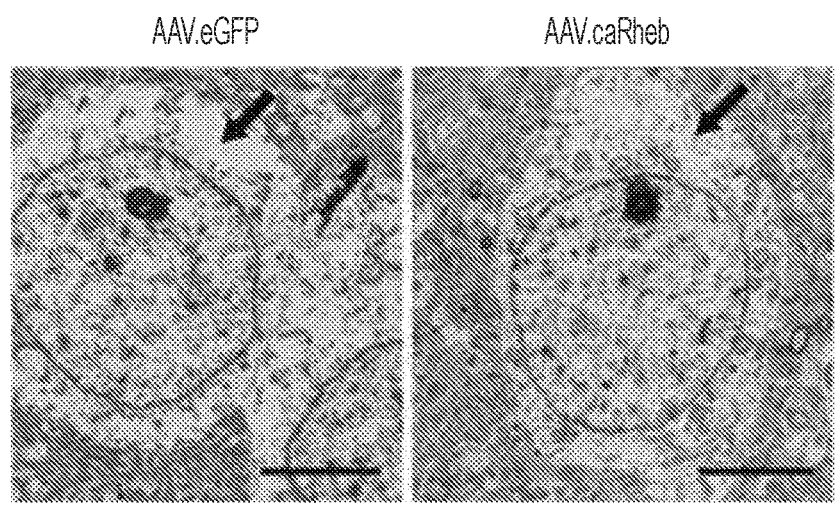
Figure 12:
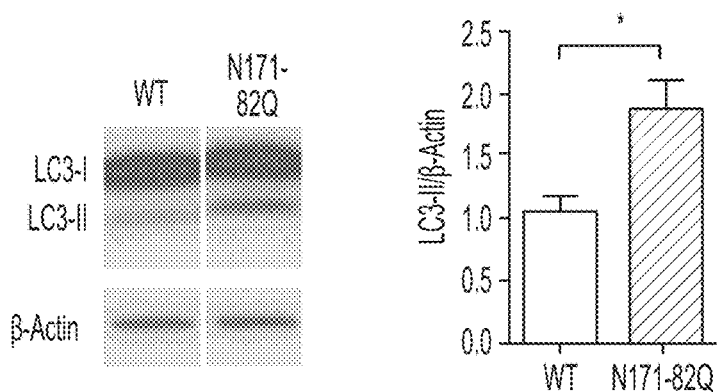
FIG. 12. Basal autophagy is enhanced in N171-82Q mice striata. Biochemical assessment of LC3II in striatal lysates from N171-82Q and WT mice after injection of AAV.eGFP at 10 weeks of age. Striata were harvested 3 weeks post-injection. Densitometry analysis revealed increased LC3II levels in the striatum of N171-82Q mice (N=9) compared to WT (N=5). β-actin was used as a loading control. Data are mean+SEM.*P<0.05, Student's t-test.

In N171-82Q mice, HMGCR is significantly reduced (FIG. 3C) compared to controls, similar to what has been found in HD patient brains (Hodges et al., 2006). AAV.caRheb normalized HMGCR levels, and also increased expression of enzymes required for sterol biosynthesis: HMG-CoA synthase 1 (HMGCS1), lanosterol 14α-demethylase (CYP51), and 7-dehydrocholesterol reductase (DHCR7) (FIGS. 3C-F; FIGS. S3 C-F). Similar to our in vitro findings, mTOR's regulation of striatal lipogenic gene expression is independent of the state of polyglutamine expansion in HTT, as AAV.caRheb also increased expression of these genes in WT striata as well (FIGS. 3C-3F). Although the reduction of HMGCR gene expression is mild in N171-82Q mice (transgene expressed from prion promoter) reduced expression of HMGCR, HMGCS1, DHCR7, and CYP51 are observed in HD human and other mouse models (Hodges et al., 2006; Valenza et al., 2005). Together, our results indicate that mTORC1 promotes lipogenic gene expression in the striatum, and suggest that impaired mTORC1 activity may contribute to reduced lipogenic gene expression in HD.

mTORC1 Enhances Pathways Implicated in mHTT Clearance mTORC1 activity is generally associated with antagonizing autophagy induction, although autophagy can occur through mTORC1 dependent and independent pathways. With relevance to HD, basal autophagic activity is critical for maintaining neuronal survival and promoting aggregate clearance (Jeong et al., 2009; Ravikumar et al., 2004; Yamamoto et al., 2006). As such, we next examined the effects of mTORC1 activation on autophagy in AAV.caRheb treated HD mouse striata. We found increased basal levels of the autophagosome-membrane-associated protein, LC3-II in N171-82Q mice compared to WT mice (FIG. 12). AAV.caRheb treatment increased levels of LC3-II (FIG. 4A) and Beclin-1, a protein necessary for autophagy induction (FIG. 4B). To distinguish between enhanced autophagy and impairment of autophagolysosomal maturation, electron microscopy (EM) was used to quantify the relative number of autophagosomes and autolysosomes in brains of mice treated with AAV.caRheb in one hemisphere or AAV.eGFP in the other hemisphere. While the autophagosomes/autolysosome ratio was similar between hemispheres, both autophagosomes and autolysosomes were increased with AAV.caRheb treatment compared to the control treated contralateral sides (FIG. 4C), suggesting that autophagy is activated in the setting of increased mTORC1 activity in vivo. We also noted that control treated (AAV.eGFP) N171-82Q mice brain was depleted of electron-dense endoplasm granular mass and cytoplasmic organelles (FIG. 4D), a phenotype similar to the striatal pathology induced by nucleolar stress (Kreiner et al., 2013). Conversely, cells in AAV.caRheb treated hemispheres showed enriched electron-dense cytoplasmic organelles.

Figure 5A:
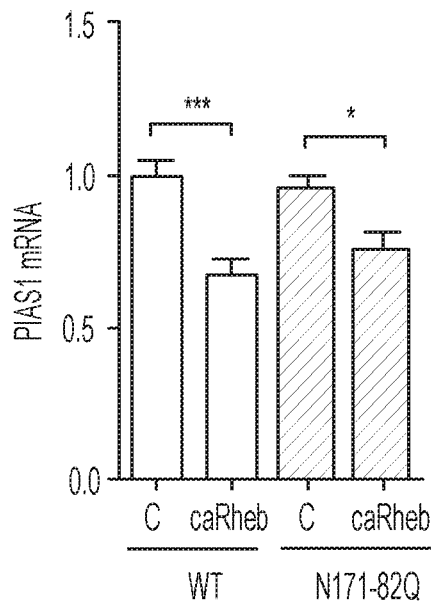
Figure 5B:
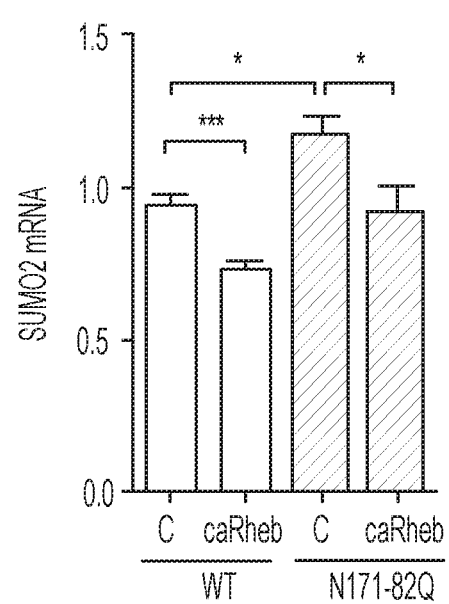
Figure 5C:
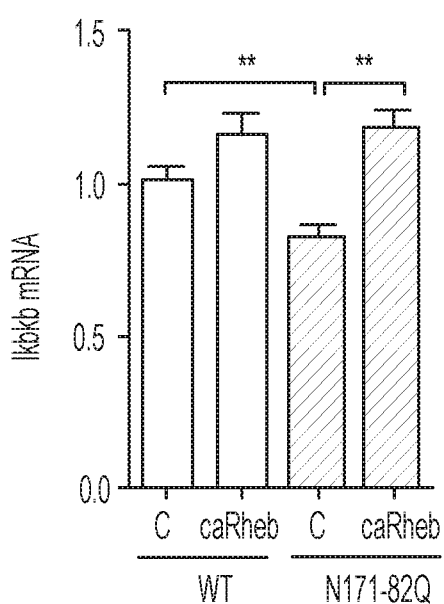
Figure 5D:
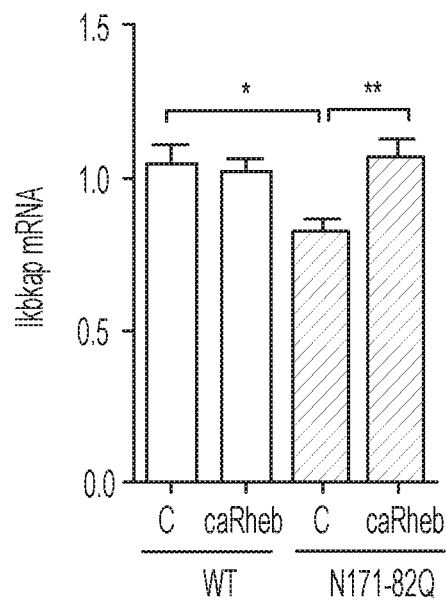
Figure 13:
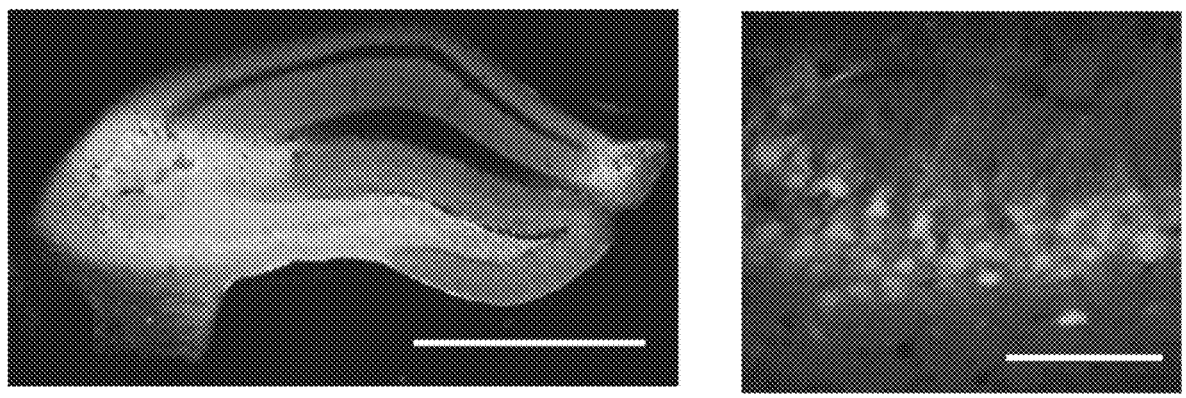
FIG. 13. AAV.eGFP transduction of hippocampus. eGFP expression in the hippocampus of N171-82Q mice 2 weeks after AAV1.eGFP injection into the dentate gyrus at 10 weeks of age. Scale bars: 1 mm (left), 100 µm (right).

Recent work suggests that autophagic/proteasomal degradation of mHTT occurs through post-translational modifications (PTM) (Jeong et al., 2009; Jia et al., 2012; O'Rourke et al., 2013; Thompson et al., 2009). For example, the SUMO E3 ligase PIAS1 increases mHTT aggregate formation by promoting SUMO2 conjugation to mHTT in cell models, and reducing the PIAS1 ortholog in Drosophila expressing the mHTT protein is protective (O'Rourke et al., 2013). We found that SUMO2 levels were elevated in 14-week-old N171-82Q mouse striatum and that AAV.caRheb repressed PIAS1 and SUMO2 expression in both N171-82Q mice and WT control littermates (FIGS. 5A, B). We also examined IκB kinase (IKK), a kinase that induces mHTT degradation and targets mHTT for clearance by the proteasome and lysosome (Thompson et al., 2009). Endogenous IKK related genes (Ikbkb, Ikbkap, and Ikbke) were reduced in N171-82Q mouse striata, and AAV.caRheb restored their expression (FIGS. 5C-E). Additionally, HDAC4 is an important regulator of mHTT aggregate formation and reduction of HDAC4 reduces cytoplasmic aggregates, improves neuronal function, and extends the life span of HD mice (Mielcarek et al., 2013). Here, we found that AAV.caRheb transduction reduced HDAC4 expression in N171-82Q mouse striata (FIG. 5F). HTT fragment-containing aggregates are few and inconsistent in striatum, but robust in hippocampus in N171-82Q mice. Therefore, we tested aggregate burden in the hippocampus. AAV efficiently transduces hippocampal neurons (FIG. 13), and AAV.caRheb injected animals showed significantly reduced mHTT aggregate load compared to AAV.eGFP injected mice (FIG. 5G), consistent with the observed effects of AAV.caRheb on genes involved in mHTT clearance.

Figure 6C:
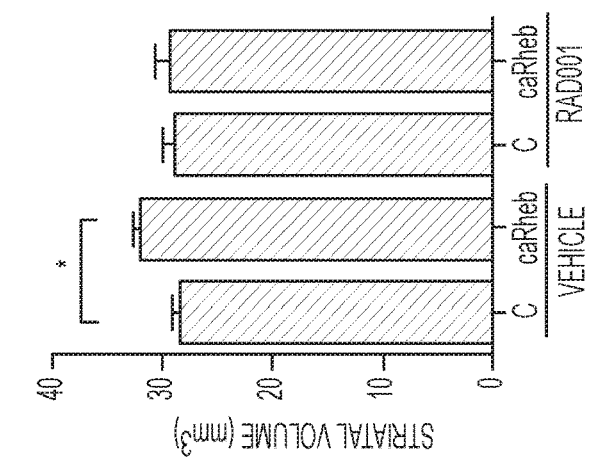
FIGS. 6A-6E. mTORC1 promotes MSN growth and counteracts mHTT-induced motor phenotypes. (A) Immunohistochemical staining of MSNs with anti-DARPP-32, 2 weeks after a single unilateral injection of AAV.caRheb into the striatum of 11-week-old N171-82Q mice. Mice were given vehicle or RAD001 for 2 weeks. (B and C) Quantification of MSN cell area and striatal volumes from tissues of animals treated as in (A) (N=4 per treatment group; mean+SEM). (D) WT mice injected unilaterally with AAV.mHTT/AAV.eGFP or AAV.mHTT/AAV.caRheb at 6 weeks of age. When tested 4 weeks post-injection, AAV.mHTT/AAV.eGFP induced ipsilateral rotational behavior in response to amphetamine. Co-injection of AAV.caRheb altered AAV.mHTT-induced ipsilateral rotation following amphetamine administration, with mice displaying contralateral rotation (N=4 per treatment group). *P<0.05, P<0.001, *P<0.001, Student's t-test. Scale bars: 100 µm (A-D). (E) Left panels, Immunohistochemical staining of MSNs with anti-DARPP-32 of sections from AAV.mHTT/AAV.eGFP or AAV.mHTT/AAV.caRheb injected mice from (D). The contralateral uninjected hemisphere is shown as control. Right panels, quantification of MSN area expressed as percentage of uninjected contralateral striata.*P<0.05, Student's t-test. Scale bars: 50 µm.
Figure 6B:
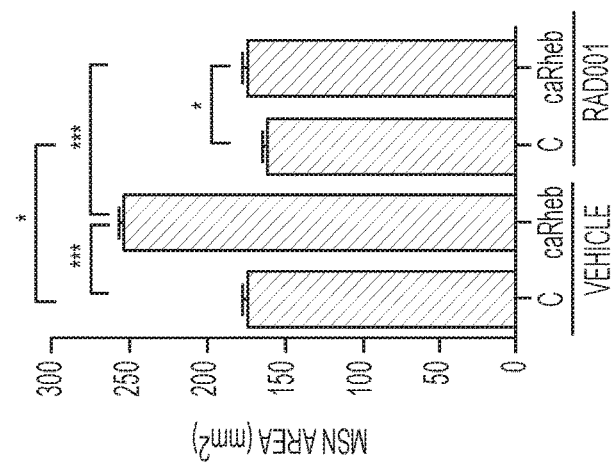
Figure 6A:
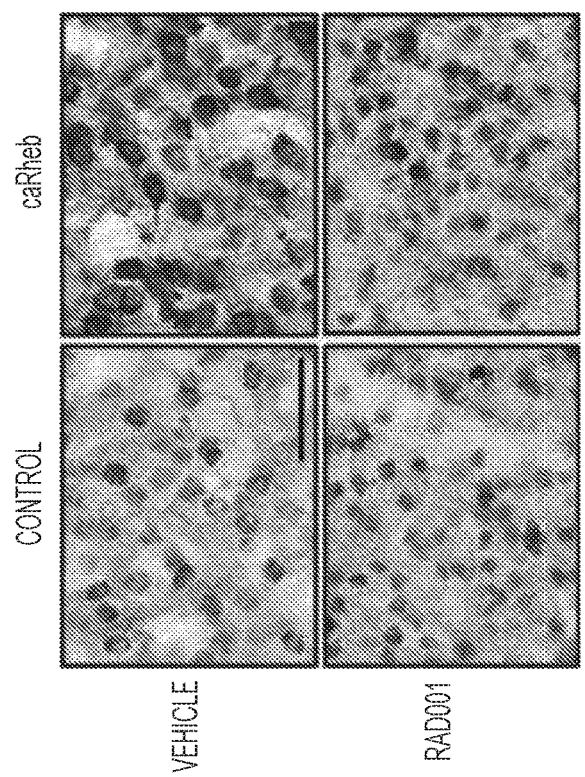
Figure 14A:
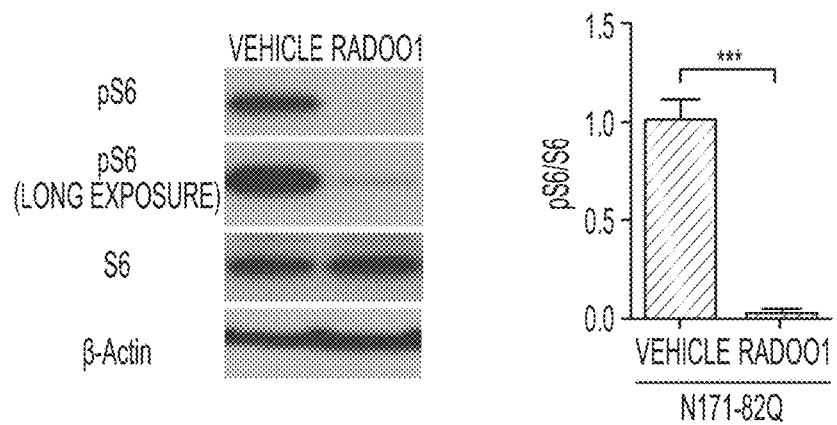

Enhanced mTORC1 Activity Rescues Striatal Atrophy and Improves Motor Phenotypes in HD Mice N171-82Q mice display pronounced striatal atrophy with preserved MSN numbers (Cheng et al., 2011; Schilling et al., 1999). To examine how mTORC1 activity impacts striatal volume in diseased brain, we performed unilateral AAV.caRheb injection into the striata of 11-week-old N171-82Q mice, an age by which there is measurable striatal atrophy (Cheng et al., 2011), and compared the treated hemisphere with the untreated side. AAV.caRheb positively impacted MSN cell size and striatal volume compared to untreated contralateral hemispheres (FIGS. 6A-C). To confirm that caRheb acts through mTORC1, we administered RAD001, a known mTORC1 inhibitor (Fox et al., 2010). RAD001 treatment reversed the morphological effects of caRheb and attenuated S6 phosphorylation (FIGS. 6A-6C; FIGS. 14A, B). Additionally, we found that 2 weeks of RAD001 treatment in the absence of caRheb caused a mild but significant exacerbation of MSN atrophy in N171-82Q mice (FIGS. 6A, B). These results suggest that AAV.caRheb promotes MSN growth or preserves MSN size through the mTORC1 pathway, and that impairing mTORC1 in vivo exacerbates this phenotype.

Figures 6D, 6E:
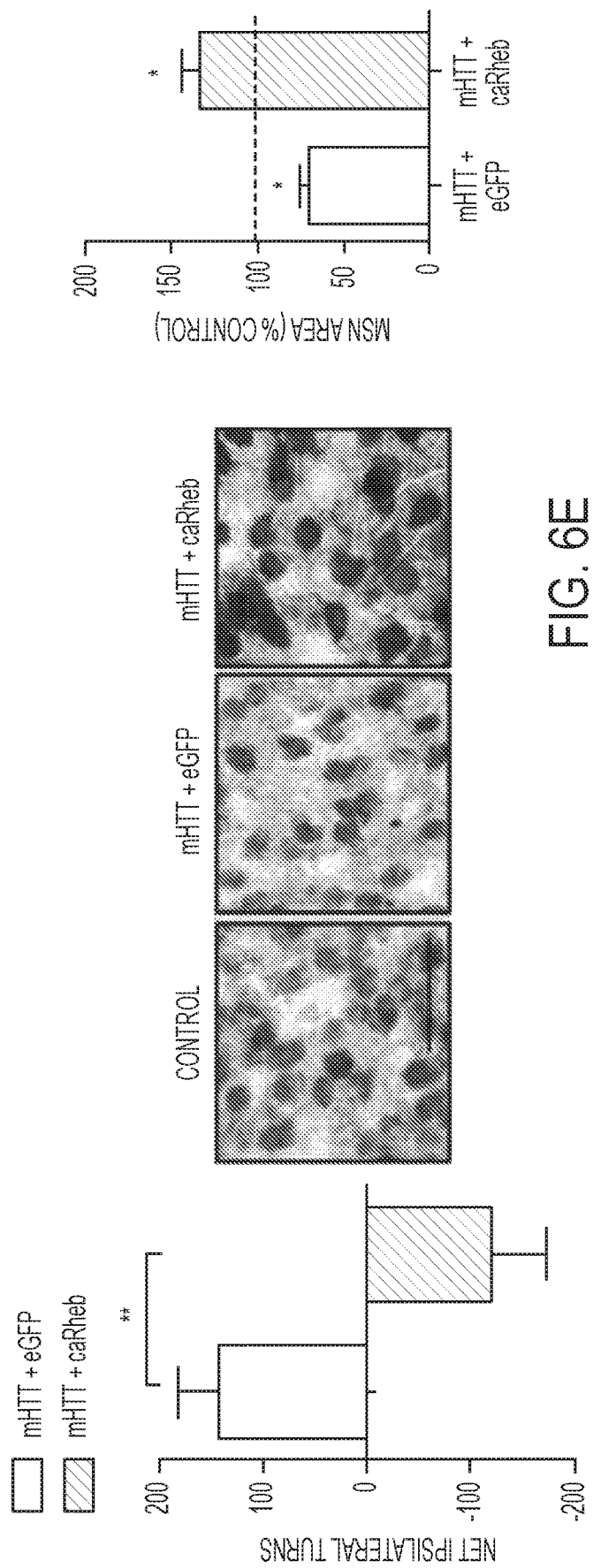

Impaired striatal dopamine circuitry is associated with motor symptoms in HD mice (Bibb et al., 2000; Johnson et al., 2006). Therefore, to determine the functional impact of AAV.caRheb on dopamine pathways we unilaterally injected N171-82Q mice and subjected them to amphetamine induced rotational tests. Amphetamine triggers dopamine release and induces rotational behavior in mice if there is imbalanced dopamine signaling in one hemisphere versus the other. For this, we co-injected AAV expressing mHTT (AAV.mHTT) into 6-week-old WT mice with either AAV.caRheb or control virus (AAV.eGFP). Unilateral injection of AAV.mHTT/AAV.eGFP caused ipsilateral rotation toward the injected side, an indication of mHTT toxicity (FIG. 6D). In contrast, co-injection of AAV.caRheb with AAV.mHTT did not induce ipsilateral rotation, instead mice displayed contralateral rotations (FIG. 6D). Consistent with the behavioral results, injection of AAV.mHTT/eGFP caused MSN atrophy compared to untreated contralateral striatum whereas co-injection of AAV.caRheb with AAV.mHTT prevented MSN atrophy (FIG. 6E). Thus, enhancing mTORC1 activity benefits mHTT-driven neuronal atrophy and dopamine pathway impairment.

Figure 7B:
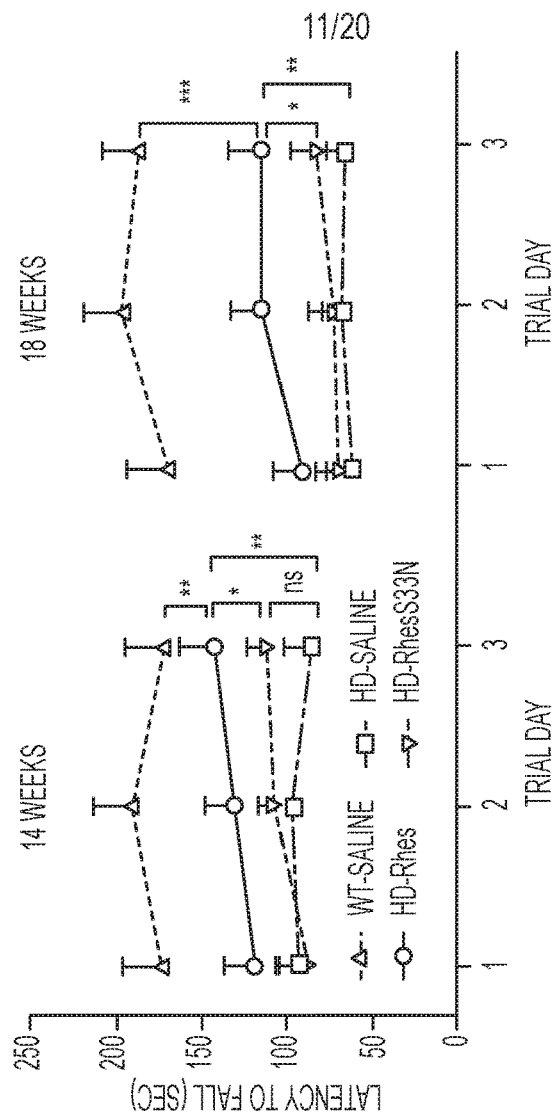
FIGS. 7A-7D. Intrastriatal Rhes overexpression improves disease phenotypes in N171-82Q mice. (A) RT-qPCR analysis of endogenous Rhes levels from striatal lysates of unaffected individuals (Ctl, N=4) and HD patients (N=10), and 6-week-old N171-82Q (N=5) and WT (N=4) littermates. Data represent mean+SEM. *P<0.05, ***P<0.001, Student's t-test. (B) Rotarod assessment of N171-82Q and WT mice after bilateral injection of AAV.Rhes, AAV.RhesS33N, or saline into the striatum at 7 weeks of age (N=10-14 mice per group at 14 weeks of age; N=6-13 mice per group at 18 weeks of age). Rotarod data from three consecutive days at 14 and 18 weeks of age are shown as latency to fall. Saline and AAV.RhesS33N-injected N171-82Q mice performed significantly worse compared to AAV.Rhes-injected N171-82Q mice on the rotarod at 14 and 18 weeks of age. NS=Not statistically significant. Data represent mean+SEM. *P<0.05; P<0.01; *P<0.001, One-way ANOVA with Tukey's post-hoc test. (C) DARPP-32 staining and quantification of MSN area of N171-82Q mice striatal tissue sections after unilateral injection of AAV.Rhes and contralateral injection of AAV.GFP at 7 weeks of age. Tissues were harvested at 19 weeks of age (N=3 mice/group; GFP=245 cells; Rhes=251 cells). Data represent mean+SEM. ***P<0.001, Student's t-test. Scale bars: 50 µm. (D) qPCR analysis of PGC-1α in striata from AAV.Rhes- or saline-treated N171-82Q and WT mice (n=6-9 per group) harvested at the end of the study (19 weeks of age). C=Control. *P<0.05, Student's t-test.
Figure 7A:
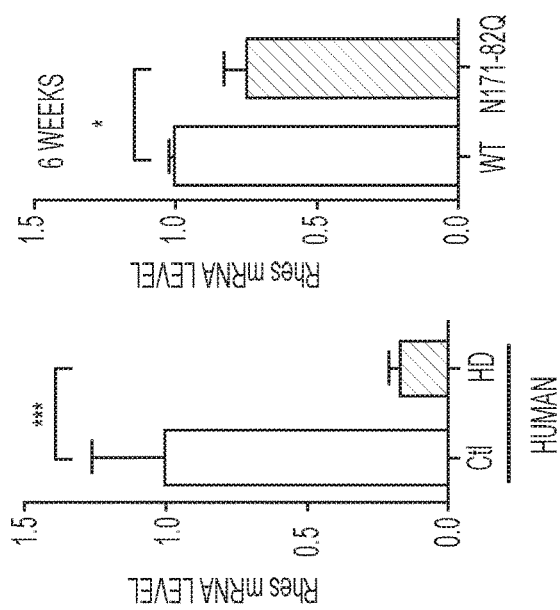
Figures 7C, 7D:
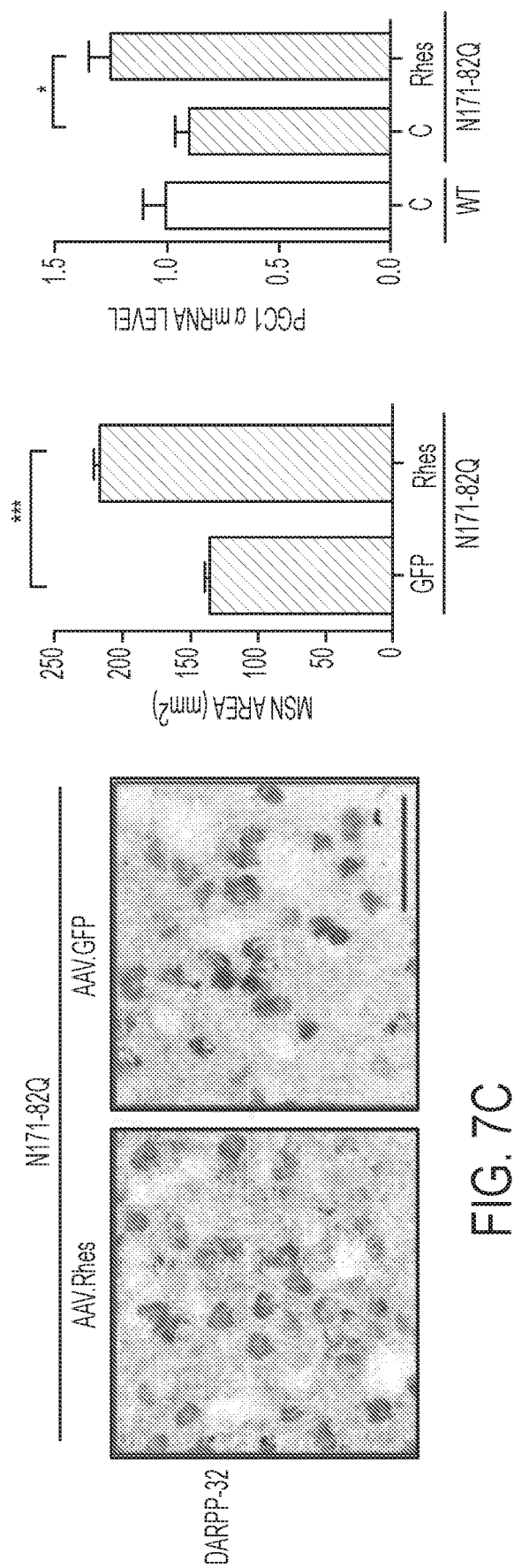

Exogenous Addition of Rhes, a Striatum-Enriched mTOR Activator, Rescues mHTT-Associated Disease Phenotypes in HD Transgenic Mice In the striatum, mTOR is predominantly regulated by a striatal-enriched GTPase protein, Rhes (Subramaniam et al., 2012). Prior in vitro studies imply a toxic role of Rhes in HD (Subramaniam et al., 2009), but its disease relevance in vivo is unclear. We found that Rhes levels were reduced in HD human and mouse striata (FIGS. 7A and 15A). Rheb levels are not reduced (FIG. 15B). Notably, Rhes is significantly reduced prior to the onset of neurological symptoms; 6-week-old N171-82Q mice have 73% of wild type Rhes levels even though clinical symptoms are not evident until 12-14 weeks of age (FIGS. 7A and 15C). We therefore investigated how enhancing Rhes levels impacts disease phenotypes. As the N-terminal fragment of mHTT was previously shown to interact with Rhes and confer cytotoxicity in vitro, the N171-82Q model is ideal for testing this question in vivo (Subramaniam et al., 2009). If Rhes is a critical mediator of HD toxicity, acute overexpression of Rhes in N171-82Q mouse striata would be expected to exacerbate disease phenotypes. AAVs expressing Rhes (AAV.Rhes) were injected into 7-week-old N171-82Q mice and WT littermates. In contrast to what was expected from earlier in vitro work, but consistent with our findings on mTORC1 activation by Rheb, Rhes overexpression improved motor function in N171-82Q mice compared to saline-treated, disease littermates as determined by rotarod testing at 14 and 18 weeks of age (FIG. 7B). In addition, after unilateral injection, AAV.Rhes significantly increased MSN cell size compared to control-treated contralateral hemispheres (FIG. 7C) Similar to Rheb, AAV.Rhes upregulated expression of the mitochondrial transcriptional regulator, PGC1-α (FIG. 7D).

In cell based assays, Rhes enhances mHTT toxicity by promoting SUMOylation of mHTT (Subramaniam et al., 2009). To ascertain if the observed disease modifying effects of Rhes in vivo are via the mTORC1 or SUMOylation pathways, we generated AAVs that express RhesS33N (AAV.RhesS33N), a Rhes mutant with abolished GTPase activity and reduced mTORC1 activation but intact SUMOylation modulatory activity (Subramaniam et al., 2012; Subramaniam et al., 2009). Following striatal injections, AAV.RhesS33N-treated N171-82Q mice showed reduced mTORC1 activity compared to N171-82Q mice injected with AAV.Rhes (FIG. 16). AAV.RhesS33N failed to modify motor deficits in N171-82Q mice, which performed similarly to control treated N171-82Q mice (FIG. 7B). Notably, Rhes S33N does not cause further behavioral exacerbation, as one would predict based on prior in vitro observation (Subramaniam et al., 2009). Collectively, these data suggest that Rhes rescues HD behavioral deficits in part via mTORC1 activation.

DISCUSSION

Figure 8:
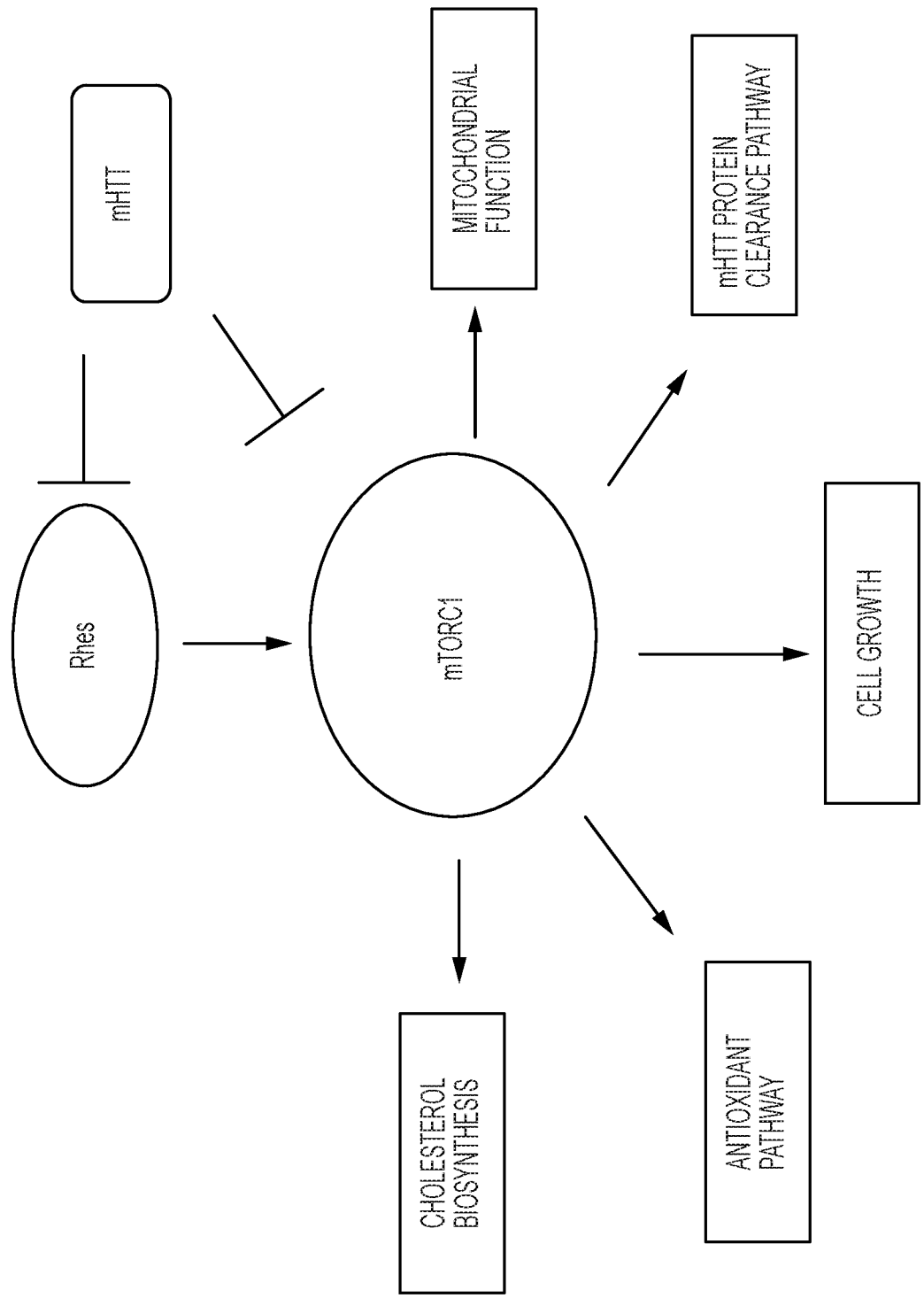
FIG. 8. Proposed mechanism through which impaired mTOR contributes to complex disease phenotypes in HD. Under normal physiological condition, mTOR regulates varied biological processes that are crucial for neuronal function and survival. In HD, mHTT disrupts mTORC1 function by direct interaction with mTOR, causing neuronal dysfunction by negatively impacting multiple pathways. In the striatum, mHTT further impairs mTORC1 activity by interfering with Rhes, a striatum enriched mTOR regulator. Thus, a concomitant loss of Rhes and mTORC1 activity may render striatal tissue vulnerable to early degeneration in HD.

Cumulatively, we show that impaired mTORC1 activity is upstream of various phenotypic changes associated with HD, and may underlie the metabolic and degenerative phenotypes. We find that mTORC1 activation promoted energy metabolism, autophagy, and striatal cell function in HD mice. Consistent with a neuroprotective role of mTORC1, we find that Rhes, a striatum-enriched mTOR activator, is reduced in HD brains prior to onset of neurological symptoms, and that exogenous Rhes addition alleviates motor deficits and brain pathology in HD mice. Notably, the ability to promote striatal cell growth and function in symptomatic HD mice supports the notion that there is plasticity in mHTT-laden neurons (Yamamoto et al., 2000), and highlights the possibility of reverting striatal atrophy after disease onset through mTORC1 activation. Because mHTT has an increased propensity to bind Rhes (Subramaniam et al., 2009) and mTOR (Ravikumar et al., 2004), it is possible that a concomitant loss of Rhes and mTOR function by mHTT may render the striatum more vulnerable to early degeneration in HD (FIG. 8). Given that striatal volume is a strong predictor of disease progression in HD patients (Tabrizi et al., 2013), therapies that restore striatal mTORC1 activity to normal levels may alleviate disease. A key disease mechanism by which mHTT interferes with energy production is repression of PGC-1α activity, whose expression is reduced in human caudate and HD transgenic mouse striata (Cui et al., 2006; Hodges et al., 2006; Tsunemi et al., 2012). Reduced PGC-1α levels may also sensitize HD brains to oxidative stress as dopaminergic neurons in PGC-1α KO mice are vulnerable to MPTP mediated oxidative damage (St-Pierre et al., 2006). Restoring brain PGC-1α expression ameliorates striatal atrophy in R6/2 HD mice (Cui et al., 2006), and improves motor phenotypes in the N171-82Q and R6/2 HD mouse models (Cui et al., 2006; Tsunemi and La Spada, 2011). Our finding that mTOR is a positive regulator of PGC-1α activity in HD mouse brains provides a therapeutic target for enhancing PGC-1α activity and a potential mechanism by which PGC-1α activity may be impaired.

At first blush, these data may appear to contradict the conventional view in the HD field indicating that mTORC1 inhibition is protective (Ravikumar et al., 2004; Roscic et al., 2011). Inhibition of mTORC1 by systemic delivery of rapamycin attenuates disease phenotypes in *Drosophila* and N171-82Q HD mice (Ravikumar et al., 2004). It is possible however that, the behavioral improvements induced by rapamycin may reflect the beneficial effects on skeletal muscle, rather than mTORC1 inhibition in the brain. In line with this, in R6/2 HD mice treated with rapamycin, rotarod improvement is transient and associated with accelerated weight loss and enhanced brain atrophy (Fox et al., 2010). Interestingly, mTORC1 activity is abnormally elevated in R6/2 mouse skeletal muscles (She et al., 2011). Together with our data, these findings support the notion that restoring balanced mTORC1 activity is critical and raise the interesting point that there can be tissue specific effects of mHTT on mTOR activity; unlike skeletal muscle, brain mTORC1 activity is already impaired in HD.

The finding that mTORC1 enhancement is neuroprotective also provides a mechanistic basis for earlier studies supporting a role for various agents shown to be therapeutic in HD models. For example, restoring BDNF-TrkB signaling has well-established neuroprotective effects in several preclinical HD models (Jiang et al., 2013; Simmons et al., 2013; Xie et al., 2010; Zuccato et al., 2001). A physiological consequence of this signaling cascade is mTORC1 activation (Troca-Marin et al., 2011; Zhou et al., 2010). Moreover, an RNAi screen identified Lkb-1 as a potent disease modifier in cell and *drosophila* HD models (Schulte et al., 2011). Lkb-1 is a tumor suppressor that negatively regulates mTORC1 (Shaw et al., 2004). Suppressing Lkb-1 improved mHTT-induced dysmorphic neurite growth in primary neurons, and rescued lethality and neurodegenerative phenotypes in *drosophila* expressing a mHTT allele (Schulte et al., 2011). Together, these results are consistent with our view that re-balancing mTORC1 activity is beneficial in HD.

Autophagy is essential for cell homeostasis and protein clearance (Wong and Cuervo, 2010). We find that mTORC1 activation stimulates autophagic activity in HD mouse brains and alters expression of genes implicated in promoting mHTT degradation (PIAS1, SUMO2, IKK, and HDAC4). These results may be surprising as mTORC1 is generally considered inhibitory to autophagy. However, recent evidence demonstrate that autophagy can occur under mTOR stimulated conditions (Narita et al., 2011), and under prolonged starvation conditions, reactivation of mTOR promotes formation of lysosomes, which are required for sustained autophagy (Yu et al., 2010). We suspect that enhanced basal or quality control autophagy is a necessary response to cell growth and metabolic activity, and unlike starvation-induced autophagy, is consistent with mTORC1 activation. Although the precise mechanism by which mTORC1 induces autophagy is unclear, we found mTORC1 enhancement increased beclin1 levels, an essential component involved in autophagic vesicle nucleation. Interestingly, overexpression of beclin 1 induces autophagic clearance of mHTT aggregates (Shoji-Kawata et al., 2013). Additionally, we find that mTORC1 upregulates expression of IKK, a known autophagy inducer that promotes mHTT degradation (Thompson et al., 2009). Further, stimulation of IGF1/Akt signaling, which in-turn activates mTORC1, induces mHTT phosphorylation and targets mHTT degradation (Humbert et al., 2002; Yamamoto et al., 2006). Cumulatively the data show that varied mechanisms for mHTT degradation are interrelated and controlled by mTORC1 activity.

The striatum-enriched protein, Rhes, is proposed to cause striatal degeneration by promoting SUMOylation of mHTT; siRNA knockdown of SUMO1 abolishes Rhes mediated cytotoxicity in vitro (Subramaniam et al., 2009). Contrary to the potential toxic role of Rhes, we find that Rhes addition improves neuropathological and motor phenotypes in HD mice, and that this neuroprotective property of Rhes requires its GTPase activity. This is in contrast to the in vitro condition, where the GTPase activity of Rhes is not involved with mHTT-mediated cytotoxicity. Interestingly, we find that reducing Rhes levels in vivo causes compensatory up-regulation of SUMO1 in HD mouse striata (data not shown). This is consistent with the observation that SUMO1 and SUMO2 modified proteins accumulate in HD postmortem human brains (O'Rourke et al., 2013). Additionally, overexpressing the GTPase deficient but SUMOylation intact Rhes mutant does not exacerbate motor phenotypes in N171-82Q mice as one would predict based on prior in vitro results (Subramaniam et al., 2009), implying that the in vivo modulators of MSN toxicity is distinct from that in an isolated culture system.

Consistent with a cytoprotective role of Rhes, we recently reported that siRNA knock-down of Rhes exacerbates striatal atrophy and behavioral phenotypes in transgenic HD mice (Lee et al., 2014). On the other hand, other work showed that crossing Rhes KO mice with R6/1 mice delayed rotarod deficits (Baiamonte et al., 2013). However, genetic deletion of Rhes does not prevent striatal atrophy in the R6/1 mice; and Rhes KO mice demonstrate severe brain degeneration similar to HD mice (Baiamonte et al., 2013). Further, Rhes levels are reduced in HD patients and HD mouse model striata, with symptomatic HD patients showing a striking 83% reduction of striatal Rhes compared to unaffected individuals (FIG. 7A). Rhes has recently been shown to promote autophagy (Mealer et al., 2014), and regulate intracellular iron homeostatsis (Choi et al., 2013). Therefore, restoring rather than reducing Rhes may be beneficial in HD brains.

The finding that normalizing mTORC1 activity improves HD phenotypes may have broad therapeutic implication for neurological diseases with deregulated mTOR activity. For instance, neurodevelopmental disorders such as fragile X mental retardation and autism are generally associated with hyperactive mTORC1 activity; suppressing mTORC1 in these conditions improves disease phenotypes (Bhattacharya et al., 2012; Tsai et al., 2012). In contrast, in the case of amyotrophic lateral sclerosis (ALS) where neuronal mTORC1 activity is reduced, stimulation of mTORC1 counteracts the degenerative process (Saxena et al., 2013). Thus, restoring the homeostatic level of mTORC1 function may broadly benefit neurological diseases.

In summary, our study provides new insight into the inter-connectivity of complex pathological phenotypes in HD, which converge on the mTORC1 pathway. And, together with prior work in other neurodegenerative disease fields, highlights the observation that the extent of mTORC1 activation must be carefully controlled for therapeutic utility. While reducing the expression of the mHTT in the brain would be a direct way to rescue mTORC1 activity in the setting of HD, a rebalance of mTORC1 activity may be of therapeutic benefit.

Experimental Procedures

Animals.

All animal protocols were approved by the University of Iowa Animal Care and Use Committee. N171-82Q mice were obtained from Jackson Laboratories (Bar Harbor, Me.) and maintained on B6C3F1/J background. Mice were genotyped using primers specific for the mutant human HTT transgene, and hemizygous and age-matched wild-type littermates were used for the indicated experiments. Mice were housed in a controlled temperature environment on a 12-hour light/dark cycle. Food and water were provided ad libitum. For pharmacological studies, RAD001 was obtained from LC Laboratories, diluted to 2 mg/ml in 2% DMSO, and stored at −20° C. Freshly thawed vehicle and RAD001 (30 µmol/kg) were given 3 times per week (Monday, Wednesday, and Friday) for two weeks by gavage as described previously (Fox et al., 2010). Mice were sacrificed 24 hours after the last dose.

Plasmids and AAVs

AAV vectors serotype 1 (AAV2/1) were used for this study. Rhes and Rheb cDNA sequences were amplified from a mouse striatum cDNA library. A Flag epitope was incorporated to the 3'-end by PCR for western blot detection. GTPase inactive Rhes mutant (RhesS33N) and hyperactive Rheb mutant (caRheb;S16H) were generated by QuikChange site-directed mutagenesis (Agilent Technology). The primers for mutagenesis were designed based on the QuikChange Primer Design Program (on the Worldwide-web at stratagem.com). Rhes, RhesS33N, and caRheb sequences were cloned into AAV expression vectors under the control of a chicken β-actin promoter. AAV.Rhes and AAV.RhesS33N vectors also express enhanced GFP (eGFP) under the control of an IRES sequence. In addition, an N-terminal myc-tagged N171-82Q sequence was PCR amplified from a pCMVHD-N171-82Q plasmid (Harper et al., 2005), and cloned into the same AAV expression vector to generate AAV.mHTT. All AAVs were produced by University of Iowa Vector Core. The AAV titers were determined by RT-PCR (Rhes: 3×1012 viral genomes/ml, RhesS33N: 3×1012 viral genomes/ml, caRheb: 3×1012 viral genomes/ml, eGFP: 3×1012 viral genomes/ml, and mHTT (N171-82Q): 3×1012 viral genomes/ml).

Injections

The stereotaxic coordinates used for the striatum is 0.86 mm rostral to bregma, +1.8 mm lateral to midline, 3.5 mm ventral to the skull surface. N171-82Q mice and WT littermates were injected with AAV.Rhes, AAV.RhesS33N, or saline at 7 weeks of age. For all behavioral studies, mice were injected bilaterally with 5-µl of AAV. For unilateral injection studies, 5-µl injections of AAV was used. The stereotaxic coordinates used for hippocampus is AP: −2.0 mm, ML: +1.5 mm, DV: −2.3 mm relative to bregma; mice were injected unilaterally with 1-ul of AAV. For amphet-amine induced rotation tests in WT mice, 3 µl AAV.mHTT was co-injected with either 2 µl AAV.caRheb or 2 µl AAV.eGFP into the striatum. Injection rates for all studies were 0.2 µl/min. Mice were sacrificed at indicated ages using standard approved methods (Harper et al., 2005; McBride et al., 2008).

Cell Culture and Transfections

Mutant (Q111) and WT (Q7) striatal cells (Trettel et al., 2000) with full-length HTT were kindly provided by Dr. Marcy MacDonald. The Q7 and Q111 cells were grown at 37° C. in Dulbecco's modified Eagle's medium (DMEM; Sigma Chemical Co, St. Louis, Mo.) supplemented with 10% fetal bovine serum, 1% non-essential amino acids, 2 mM L-glutamine, and 400 µg/ml G418 (Geneticin; Invitrogen, Carlsbad, Calif.). For mTOR-inhibition studies, cells were treated with DMSO or 250 nM Torin1 (Tocris, Bristol, UK) for 24 hours.

Mouse Brain Isolation

Mice used in histological analyses were anesthetized with a ketamine/xylazine mix and transcardially perfused with 20 ml of 0.9% cold saline, followed by 20 ml of 4% paraformaldehyde in 0.1 M PO4 buffer. Brains were removed and postfixed overnight, and 40-µm thick sections were collected. Mice used for molecular analyses were perfused with 20 ml of 0.9% cold saline, and brain was removed and blocked into 1-mm-thick coronalslices. Tissue punches of striatum were taken by using a tissue corer (1.4 mm in diameter). Tissue punches were flash frozen in liquid nitrogen and stored at −80° C. until used.

Immunohistochemistry and Quantitation

Floating, 40-µm coronal brain sections were processed for immunohistochemical staining of medium spiny neurons or mHTT aggregates using biotin-labeled antibody. Sections were blocked in 5% normal goat serum for 1 hour, then incubated with primary antibody (DARPP-32, 1:200, Cell Signaling) overnight and washed. mHTT aggregates were immunostained with em48 antibody (1:200, mEM48; gift from X. J. Li, Emory University School of Medicine). S6 phosphorylation was detected with a phospho-S6 antibody (S235/236, 1:300, Cell Signaling). Sections were incubated in goat anti-rabbit or goat anti-mouse biotinylated IgG secondary antibodies (1:200; Vector laboratories) for 1 hr at room temperature and then treated with avidin-biotinylated horseradish peroxidase complexes (ABC; Vector Labs). In all procedures, deletion of the primary antibody served as control. Stained sections were mounted onto Superfrost Plus slides (Fisher Scientific, Pittsburgh, Pa.). Images were captured using an Olympus BX60 light microscope and DP70 camera with Olympus DP Controller software (Olympus, Melville, N.Y.). For each brain, four representative sections were chosen and areas of 70 DARPP-32 positive medium spiny neurons (MSN) were manually traced under 40× objective from each hemisphere. The areas of DARPP-32 positive MSN were quantified by Olympus DP2-BSW software (version 2.1). The average MSN areas of ipsilateral injected sides were compared to contralateral control sides and expressed as means+SEM. EM48 positive inclusions were counted by an experimenter blinded to treatment groups.

Stereology

Striatal volume was calculated using point counting methods with the Cavalieri estimator of volume (Michel and Cruz-Orive, 1988). Briefly, images of DARPP-32 stained coronal sections (40 µm thick) were captured using an Olympus BX60 light microscope and DP70 camera with Olympus DP Controller software (Olympus, Melville, N.Y.). An acetate sheet with a grid pattern was placed on the image at random angles, and the number of grid intersections overlying the striatum was counted. A random systematic set of serial sections at an interval of 480 µm apart was used. A minimum of 200 points were counted over 5 sections. Left and right striatal volumes were determined independently on the same sections from the point counts by using the formula Vol (object)=ΣP (object)·t·a(p), where ΣP (object)=sum of points overlying the striatum, t=distance between sections, and Ap=area per point.

Electron Microscopy

Mice were anesthetized and perfused intracardially with saline solution followed by 2.5% glutaraldehyde in 0.1M sodium cacodylate buffer pH 7.4. Brains were removed and post-fixed in 2.5% glutaraldehyde, 0.1M sodium cacodylate buffer pH 7.4 for 24 hours. 100 µm coronal sections were cut with vibratome and fixed in 1% OsO4 in 0.1M cacodylate for 1 h, stained with 1% uranyl acetate, dehydrated and embedded in Eponate 812. Semithin 1-µm Toluidine Blue stained sections were examined under the light microscope to identify striatum. Ultrathin sections of striatum (80 nm) were examined with a JEOL EX 1200 transmission electron microscope.

Western Blot Analysis

Mouse striata were harvested and lysed in RIPA buffer containing 50 mM Tris (pH 8.0), 150 mM NaCl, 1% NP450 detergent, 0.1% SDS detergent, 0.5% deoxycholic acid, and 1 mM β-mercaptoethanol with protease inhibitors (Complete Mini, Roche Applied Science, Mannheim, Germany) and phosphatase inhibitors (PhosSTOP Phosphatase Inhibitor Cocktail, Roche Applied Science, Mannheim, Germany). Tissues were homogenized on ice and spun at 14,000 g for 20 min. Supernatant were used for analysis. Protein concentration was determined by BCA assay (Pierce, Rockford, Ill.) and 20-30 µg of protein was reduced and separated by SDS-PAGE on 4%-10% acrylamide gels and transferred to 0.2 µm Immobilon PVDF membranes (Millipore, Billerica, Mass.). The primary antibodies used were as follows: DARPP-32 (1:1000, Cell Signaling), β-actin (Sigma-Aldrich, 1:5000), S6 (1:1000, Cell Signaling), phospho-S6 (S235/236, 1:1000, Cell Signaling), 4EBP1 (1:1000, Cell Signaling), phospho-4E-BP1 (T37/46, 1:1000, Cell Signaling), mTOR (1:1000, Cell Signaling), Rictor (1:1000, Cell Signaling), Raptor (1:1000, Cell Signaling), CREB (1:1000, Cell Signaling), TORC1 (1:1000, Cell Signaling), PGC1-α (1:1000, abeam), LC3 (1:1000, Novus Biologicals), and Beclin1 (1:1000, Cell Signaling). Secondary antibodies used were HRP-goat anti-mouse IgG and HRP-goat anti-rabbit IgG (Cell Signaling). Blots were developed using ECL Plus Western Blotting Detection System (GE Healthcare, Pittsburgh, Pa.), and then exposed to film. Protein quantification was performed using NIH ImageJ software or the VersaDoc™ Imaging System (Biorad) and Quantity One R analysis software. Band densities were normalized to housekeeping (β-actin) bands from the same samples and lanes.

Brain Samples

Coronal sections of human autopsy brain tissues were obtained from unaffected individuals and patients with Vonsattel grade 2, 3 and 4 HD (Dr. Christopher Ross, Johns Hopkins University; New York Brain Bank at Columbia University, Alzheimer Disease Research Center, Taub Institute). Tissues were flash frozen with postmortem intervals (PMI) ranging from 13 to 49 hours. Caudate/putamen nuclei were dissected from the frozen tissues placed on an ice-cold metal stage and homogenized in RIPA buffer with protease inhibitors (Complete Mini, Roche Applied Science, Mannheim, Germany) and phosphatase inhibitors (PhosSTOP Phosphatase Inhibitor Cocktail, Roche Applied Science, Mannheim, Germany). Lysates were spun at 14,000 g for 20 min. The supernatant was collected for western blot analysis. Additional frozen tissues were processed for RNA extraction using TRIzol. Quantitative real-time PCR (RT-qPCR).

RNA was isolated from striatal punches using 1 ml of TRIzol. Random-primed first-strand complementary DNA (cDNA) synthesis was performed using 500 ng total RNA (High Capacity cDNA Reverse Transcription Kit; Applied Biosystems, Foster City, Calif.) per manufacturer's protocol. Real-time PCR was performed on a sequence detection system (Prism 7900HT, Applied Biosystems) using SYBR green PCR mix (Invitrogen) or TaqMan 2× Universal Master Mix (Applied Biosystems). The following Taqman primer/probe sets were obtained from Applied Biosystem: Rhes (Mm04209172_m1 and Hs04188091_mH), PGC1-α (Mm01208835_m1), and HMGCS1 (Mm01304569_m1), and HDAC4 (Mm01299557_m1). The primer sequences for SYBR green RT PCR are available upon request. Relative gene expression was determined using the ΔΔCT method, normalizing to β-actin.

Behavioral Tests

Amphetamine Induced Rotational Assay

Mice were injected with intraperitoneal amphetamine (3 mg/kg; Sigma), and then placed individually in the center of a square plastic activity chamber (50×50 cm). Mice were allowed to habituate in the chamber for 20 min before amphetamine induction. Rotational behavior was then recorded for 40 min by a ceiling-mounted video camera. Net rotation was expressed as number of ipsilateral turns—number of contralateral turns in a 40 min session.

Accelerating Rotarod

Male N171-82Q mice were tested for baseline motor function at 6 weeks of age, and then at 10, 14, and 18 weeks of age. Before each test, mice were first habituated on the rotarod for 4 minutes and rested for one hour. The tests were conducted three trials per day (with 30 minutes of rest between trials) for four consecutive days. For each trial, mice were placed on the rod that accelerates from 4-40 rotations per min over 4 minutes, and then speed maintained at 40 rpm. Latency to fall (or if mice hung on for two consecutive rotations without running) was used as a rating of motor performance. The trials were stopped at 300 seconds, and mice remaining on the rotarod at that time were scored as 300 sec. Data from the three trials for each group on each day are presented as means±SEM. Mice were always tested in the dark phase of the light/dark cycle. All behavioral experiments were conducted with the experimenter blind to mouse genotypes and treatments.

Statistical Analyses

Data were analyzed using Student's t-test or One-way ANOVA analysis, followed by Tukey's post hoc analyses to assess for significant differences between individual groups. All statistical analyses were performed using GraphPad Prism version 5.0c. Data are expressed as mean±SEM. In all cases, P<0.05 was considered significant.

REFERENCES (1993). A novel gene containing a trinucleotide repeat that is expanded and unstable on Huntington's disease chromosomes. The Huntington's Disease Collaborative Research Group. Cell 72, 971-983.

Baiamonte, B. A., Lee, F. A., Brewer, S. T., Spano, D., and LaHoste, G. J. (2013). Attenuation of Rhes activity significantly delays the appearance of behavioral symptoms in a mouse model of Huntington's disease. PLoS One 8, e53606.

Bhattacharya, A., Kaphzan, H., Alvarez-Dieppa, A. C., Murphy, J. P., Pierre, P., and Klann, E. (2012). Genetic removal of p70 S6 kinase 1 corrects molecular, synaptic, and behavioral phenotypes in fragile X syndrome mice. Neuron 76, 325-337.

Bibb, J. A., Yan, Z., Svenningsson, P., Snyder, G. L., Pieribone, V. A., Horiuchi, A., Nairn, A. C., Messer, A., and Greengard, P. (2000). Severe deficiencies in dopamine signaling in presymptomatic Huntington's disease mice. Proc Natl Acad Sci USA 97, 6809-6814.

Cheng, Y., Peng, Q., Hou, Z., Aggarwal, M., Zhang, J., Mori, S., Ross, C. A., and Duan, W. (2011). Structural MRI detects progressive regional brain atrophy and neuroprotective effects in N171-82Q Huntington's disease mouse model. Neuroimage 56, 1027-1034.

Choi, B. R., Bang, S., Chen, Y., Cheah, J. H., and Kim, S. F. (2013). PKA modulates iron trafficking in the striatum via small GTPase, Rhes. Neuroscience 253, 214-220.

Cui, L., Jeong, H., Borovecki, F., Parkhurst, C. N., Tanese, N., and Krainc, D. (2006). Transcriptional repression of PGC-1alpha by mutant huntingtin leads to mitochondrial dysfunction and neurodegeneration. Cell 127, 59-69.

Cunningham, J. T., Rodgers, J. T., Arlow, D. H., Vazquez, F., Mootha, V. K., and Puigserver, P. (2007). mTOR controls mitochondrial oxidative function through a YY1-PGC-1alpha transcriptional complex. Nature 450, 736-740.

Fox, J. H., Connor, T., Chopra, V., Dorsey, K., Kama, J. A., Bleckmann, D., Betschart, C., Hoyer, D., Frentzel, S., Difiglia, M., et al. (2010). The mTOR kinase inhibitor Everolimus decreases S6 kinase phosphorylation but fails to reduce mutant huntingtin levels in brain and is not neuroprotective in the R6/2 mouse model of Huntington's disease. Mol Neurodegener 5, 26.

Harper, S. Q., Staber, P. D., He, X., Eliason, S. L., Martins, I. H., Mao, Q., Yang, L., Kotin, R. M., Paulson, H. L., and Davidson, B. L. (2005). RNA interference improves motor and neuropathological abnormalities in a Huntington's disease mouse model. Proc Natl Acad Sci USA 102, 5820-5825.

Hodges, A., Strand, A. D., Aragaki, A. K., Kuhn, A., Sengstag, T., Hughes, G., Elliston, L. A., Hartog, C., Goldstein, D. R., Thu, D., et al. (2006). Regional and cellular gene expression changes in human Huntington's disease brain. Hum Mol Genet 15, 965-977.

Humbert, S., Bryson, E. A., Cordelieres, F. P., Connors, N. C., Datta, S. R., Finkbeiner, S., Greenberg, M. E., and Saudou, F. (2002). The IGF-1/Akt pathway is neuroprotective in Huntington's disease and involves Huntingtin phosphorylation by Akt. Dev Cell 2, 831-837. Jeong, H., Then, F., Melia, T. J., Jr., Mazzulli, J. R., Cui, L., Savas, J. N., Voisine, C., Paganetti, P., Tanese, N., Hart, A. C., et al. (2009). Acetylation targets mutant huntingtin to autophagosomes for degradation. Cell 137, 60-72.

Jia, H., Kast, R. J., Steffan, J. S., and Thomas, E. A. (2012). Selective histone deacetylase (HDAC) inhibition imparts beneficial effects in Huntington's disease mice: implications for the ubiquitin-proteasomal and autophagy systems. Hum Mol Genet 21, 5280-5293.

Jiang, M., Peng, Q., Liu, X., Jin, J., Hou, Z., Zhang, J., Mori, S., Ross, C. A., Ye, K., and Duan, W. (2013). Small-molecule TrkB receptor agonists improve motor function and extend survival in a mouse model of Huntington's disease. Hum Mol Genet 22, 2462-2470.

Johnson, M. A., Rajan, V., Miller, C. E., and Wightman, R. M. (2006). Dopamine release is severely compromised in the R6/2 mouse model of Huntington's disease. J Neurochem 97, 737-746.

Karasinska, J. M., and Hayden, M. R. (2011). Cholesterol metabolism in Huntington disease. Nat Rev Neurol 7, 561-572.

Kim, S. R., Kareva, T., Yarygina, O., Kholodilov, N., and Burke, R. E. (2012). AAV transduction of dopamine neurons with constitutively active Rheb protects from neurodegeneration and mediates axon regrowth. Mol Ther 20, 275-286.

Kreiner, G., Bierhoff, H., Armentano, M., Rodriguez-Parkitna, J., Sowodniok, K., Naranjo, J. R., Bonfanti, L., Liss, B., Schutz, G., Grummt, I., et al. (2013). A neuroprotective phase precedes striatal degeneration upon nucleolar stress. Cell Death Differ.

Laplante, M., and Sabatini, D. M. (2012). mTOR signaling in growth control and disease. Cell 149, 274-293.

Lee, J. H., Sowada, M. J., Boudreau, R. L., Aerts, A. M., Thedens, D. R., Nopoulos, P., and Davidson, B. L. (2014). Rhes Suppression Enhances Disease Phenotypes in Huntington's Disease Mice. J Huntingtons Dis 3, 65-71.

Li, H., Li, S. H., Yu, Z. X., Shelbourne, P., and Li, X. J. (2001). Huntingtin aggregate-associated axonal degeneration is an early pathological event in Huntington's disease mice. J Neurosci 21, 8473-8481.

Lu, B., and Palacino, J. (2013). A novel human embryonic stem cell-derived Huntington's disease neuronal model exhibits mutant huntingtin (mHTT) aggregates and soluble mHTT-dependent neurodegeneration. FASEB J 27, 1820-1829.

Mason, R. P., Casu, M., Butler, N., Breda, C., Campesan, S., Clapp, J., Green, E. W., Dhulkhed, D., Kyriacou, C. P., and Giorgini, F. (2013). Glutathione peroxidase activity is neuroprotective in models of Huntington's disease. Nat Genet 45, 1249-1254.

McBride, J. L., Boudreau, R. L., Harper, S. Q., Staber, P. D., Monteys, A. M., Martins, I., Gilmore, B. L., Burstein, H., Peluso, R. W., Polisky, B., et al. (2008). Artificial miRNAs mitigate shRNA-mediated toxicity in the brain: implications for the therapeutic development of RNAi. Proc Natl Acad Sci USA 105, 5868-5873.

Mealer, R. G., Murray, A. J., Shahani, N., Subramaniam, S., and Snyder, S. H. (2014). Rhes, a Striatal-selective Protein Implicated in Huntington Disease, Binds Beclin-1 and Activates Autophagy. J Biol Chem 289, 3547-3554.

Mealer, R. G., Subramaniam, S., and Snyder, S. H. (2013). Rhes Deletion Is Neuroprotective in the 3-Nitropropionic Acid Model of Huntington's Disease. J Neurosci 33, 4206-4210.

Michel, R. P., and Cruz-Orive, L. M. (1988). Application of the Cavalieri principle and vertical sections method to lung: estimation of volume and pleural surface area. J Microsc 150, 117-136.

Mielcarek, M., Landles, C., Weiss, A., Bradaia, A., Seredenina, T., Inuabasi, L., Osborne, G. F., Wadel, K., Touller, C., Butler, R., et al. (2013). HDAC4 reduction: a novel therapeutic strategy to target cytoplasmic huntingtin and ameliorate neurodegeneration. PLoS Biol 11, e1001717.

Milnerwood, A. J., and Raymond, L. A. (2010). Early synaptic pathophysiology in neurodegeneration: insights from Huntington's disease. Trends Neurosci 33, 513-523.

Narita, M., Young, A. R., Arakawa, S., Samarajiwa, S. A., Nakashima, T., Yoshida, S., Hong, S., Berry, L. S., Reichelt, S., Ferreira, M., et al. (2011). Spatial coupling of mTOR and autophagy augments secretory phenotypes. Science 332, 966-970.

O'Rourke, J. G., Gareau, J. R., Ochaba, J., Song, W., Rasko, T., Reverter, D., Lee, J., Monteys, A. M., Pallos, J., Mee, L., et al. (2013). SUMO-2 and PIAS1 modulate insoluble mutant huntingtin protein accumulation. Cell Rep 4, 362-375.

Park, K. K., Liu, K., Hu, Y., Smith, P. D., Wang, C., Cai, 13., Xu, B., Connolly, L., Kramvis, I., Sahin, M., et al. (2008). Promoting axon regeneration in the adult CNS by modulation of the PTEN/mTOR pathway. Science 322, 963-966.

Peterson, T. R., Sengupta, S. S., Harris, T. E., Carmack, A. E., Kang, S. A., Balderas, E., Guertin, D. A., Madden, K. L., Carpenter, A. E., Finck, B. N., et al. (2011). mTOR complex 1 regulates lipin 1 localization to control the SREBP pathway. Cell 146, 408-420.

Porstmann, T., Santos, C. R., Griffiths, B., Cully, M., Wu, M., Leevers, S., Griffiths, J. R., Chung, Y. L., and Schulze, A. (2008). SREBP activity is regulated by mTORC1 and contributes to Akt-dependent cell growth. Cell Metab 8, 224-236.

Ravikumar, B., Vacher, C., Berger, Z., Davies, J. E., Luo, S., Oroz, L. G., Scaravilli, F., Easton, D. F., Duden, R., O'Kane, C. J., et al. (2004). Inhibition of mTOR induces autophagy and reduces toxicity of polyglutamine expansions in fly and mouse models of Huntington disease. Nat Genet 36, 585-595.

Roscic, A., Baldo, B., Crochemore, C., Marcellin, D., and Paganetti, P. (2011). Induction of autophagy with catalytic mTOR inhibitors reduces huntingtin aggregates in a neuronal cell model. J Neurochem 119, 398-407.

Saxena, S., Roselli, F., Singh, K., Leptien, K., Julien, J. P., Gros-Louis, F., and Caroni, P. (2013). Neuroprotection through Excitability and mTOR Required in ALS Motoneurons to Delay Disease and Extend Survival. Neuron 80, 80-96.

Schilling, G., Becher, M. W., Sharp, A. H., Jinnah, H. A., Duan, K., Kotzuk, J. A., Slunt, H. H., Ratovitski, T., Cooper, J. K., Jenkins, N. A., et al. (1999). Intranuclear inclusions and neuritic aggregates in transgenic mice expressing a mutant N-terminal fragment of huntingtin. Hum Mol Genet 8, 397-407.

Schulte, J., Sepp, K. J., Wu, C., Hong, P., and Littleton, J. T. (2011). High-content chemical and RNAi screens for suppressors of neurotoxicity in a Huntington's disease model. PLoS One 6, e23841.

Seredenina, T., Gokce, O., and Luthi-Carter, R. (2011). Decreased striatal RGS2 expression is neuroprotective in Huntington's disease (HD) and exemplifies a compensatory aspect of HD-induced gene regulation. PLoS One 6, e22231.

Shaw, R. J., Bardeesy, N., Manning, B. D., Lopez, L., Kosmatka, M., DePinho, R. A., and Cantley, L. C. (2004). The LKB1 tumor suppressor negatively regulates mTOR signaling. Cancer Cell 6, 91-99.

She, P., Zhang, Z., Marchionini, D., Diaz, W. C., Jetton, T. J., Kimball, S. R., Vary, T. C., Lang, C. H., and Lynch, C. J. (2011). Molecular characterization of skeletal muscle atrophy in the R6/2 mouse model of Huntington's disease. Am J Physiol Endocrinol Metab 301, E49-61.

Shoji-Kawata, S., Sumpter, R., Leveno, M., Campbell, G. R., Zou, Z., Kinch, L., Wilkins, A. D., Sun, Q., Pallauf, K., Macduff, D., et al. (2013). Identification of a candidate therapeutic autophagy-inducing peptide. Nature. 494 (7436):201-6.

Simmons, D. A., Belichenko, N. P., Yang, T., Condon, C., Monbureau, M., Shamloo, M., Jing, D., Massa, S. M., and Longo, F. M. (2013). A Small Molecule TrkB Ligand Reduces Motor Impairment and Neuropathology in R6/2 and BACHD Mouse Models of Huntington's Disease. J Neurosci 33, 18712-18727.

Spano, D., Branchi, I., Rosica, A., Pirro, M. T., Riccio, A., Mithbaokar, P., Affuso, A., Arra, C., Campolongo, P., Terracciano, D., et al. (2004). Rhes is involved in striatal function. Mol Cell Biol 24, 5788-5796.

St-Pierre, J., Drori, S., Uldry, M., Silvaggi, J. M., Rhee, J., Jager, S., Handschin, C., Zheng, K., Lin, J., Yang, W., et al. (2006). Suppression of reactive oxygen species and neurodegeneration by the PGC-1 transcriptional coactivators. Cell 127, 397-408.

Steffan, J. S., Agrawal, N., Pallos, J., Rockabrand, E., Trotman, L. C., Slepko, N., Illes, K., Lukacsovich, T., Zhu, Y. Z., Cattaneo, E., et al. (2004). SUMO modification of Huntingtin and Huntington's disease pathology. Science 304, 100-104.

Subramaniam, S., Napolitano, F., Mealer, R. G., Kim, S., Errico, F., Barrow, R., Shahani, N., Tyagi, R., Snyder, S. H., and Usiello, A. (2012). Rhes, a striatal-enriched small G protein, mediates mTOR signaling and L-DOPAinduced dyskinesia. Nat Neurosci 15, 191-193.

Subramaniam, S., Sixt, K. M., Barrow, R., and Snyder, S. H. (2009). Rhes, a striatal specific protein, mediates mutant-huntingtin cytotoxicity. Science 324, 1327-1330.

Sun, F., Park, K. K., Belin, S., Wang, D., Lu, T., Chen, G., Zhang, K., Yeung, C., Feng, G., Yankner, B. A., et al. (2011). Sustained axon regeneration induced by co-deletion of PTEN and SOCS3. Nature 480, 372-375.

Tabrizi, S. J., Scahill, R. I., Owen, G., Durr, A., Leavitt, B. R., Roos, R. A., Borowsky, B., Landwehrmeyer, B., Frost, C., Johnson, H., et al. (2013). Predictors of phenotypic progression and disease onset in premanifest and early-stage Huntington's disease in the TRACK-HD study: analysis of 36-month observational data. Lancet Neurol.

Thompson, L. M., Aiken, C. T., Kaltenbach, L. S., Agrawal, N., Illes, K., Khoshnan, A., Martinez-Vicente, M., Arrasate, M., O'Rourke, J. G., Khashwji, H., et al. (2009). IKK phosphorylates Huntingtin and targets it for degradation by the proteasome and lysosome. J Cell Biol 187, 1083-1099.

Thoreen, C. C., Kang, S. A., Chang, J. W., Liu, Q., Zhang, J., Gao, Y., Reichling, L. J., Sim, T., Sabatini, D. M., and Gray, N. S. (2009). An ATP-competitive mammalian target of rapamycin inhibitor reveals rapamycin-resistant functions of mTORC1. J Biol Chem 284, 8023-8032.

Trettel, F., Rigamonti, D., Hilditch-Maguire, P., Wheeler, V. C., Sharp, A. H., Persichetti, F., Cattaneo, E., and MacDonald, M. E. (2000). Dominant phenotypes produced by the HD mutation in STHdh(Q111) striatal cells. Hum Mol Genet 9, 2799-2809.

Troca-Marin, J. A., Alves-Sampaio, A., and Montesinos, M. L. (2011). An increase in basal BDNF provokes hyperactivation of the Akt-mammalian target of rapamycin pathway and deregulation of local dendritic translation in a mouse model of Down's syndrome. J Neurosci 31, 9445-9455.

Tsai, P. T., Hull, C., Chu, Y., Greene-Colozzi, E., Sadowski, A. R., Leech, J. M., Steinberg, J., Crawley, J. N., Regehr, W. G., and Sahin, M. (2012). Autistic-like behaviour and cerebellar dysfunction in Purkinje cell Tsc1 mutant mice. Nature 488, 647-651.

Tsunemi, T., Ashe, T. D., Morrison, B. E., Soriano, K. R., Au, J., Roque, R. A., Lazarowski, E. R., Damian, V. A., Masliah, E., and La Spada, A. R. (2012). PGC-1alpha rescues Huntington's disease proteotoxicity by preventing oxidative stress and promoting TFEB function. Sci Transl Med 4, 142ra197.

Tsunemi, T., and La Spada, A. R. (2011). PGC-1alpha at the intersection of bioenergetics regulation and neuron function: From Huntington's disease to Parkinson's disease and beyond. Prog Neurobiol. 2012 May; 97(2):142-51.

Valenza, M., and Cattaneo, E. (2011). Emerging roles for cholesterol in Huntington's disease. Trends Neurosci 34, 474-486.

Valenza, M., Rigamonti, D., Goffredo, D., Zuccato, C., Fenu, S., Jamot, L., Strand, A., Tarditi, A., Woodman, B., Racchi, M., et al. (2005). Dysfunction of the cholesterol biosynthetic pathway in Huntington's disease. J Neurosci 25, 9932-9939.

Wong, E., and Cuervo, A. M. (2010). Autophagy gone awry in neurodegenerative diseases. Nat Neurosci/3, 805-811.

Xie, Y., Hayden, M. R., and Xu, B. (2010). BDNF overexpression in the forebrain rescues Huntington's disease phenotypes in YAC128 mice. J Neurosci 30, 14708-14718.

Yamamoto, A., Cremona, M. L., and Rothman, J. E. (2006). Autophagy-mediated clearance of huntingtin aggregates triggered by the insulin-signaling pathway. J Cell Biol/72, 719-731.

Yamamoto, A., Lucas, J. J., and Hen, R. (2000). Reversal of neuropathology and motor dysfunction in a conditional model of Huntington's disease. Cell 101, 57-66.

Yu, L., McPhee, C. K., Zheng, L., Mardones, G. A., Rong, Y., Peng, J., Mi, N., Zhao, Y., Liu, Z., Wan, F., et al. (2010). Termination of autophagy and reformation of lysosomes regulated by mTOR. Nature 465, 942-946.

Zhou, X., Lin, D. S., Zheng, F., Sutton, M. A., and Wang, H. (2010). Intracellular calcium and calmodulin link brain-derived neurotrophic factor to p70S6 kinase phosphorylation and dendritic protein synthesis. J Neurosci Res 88, 1420-1432.

Zou, J., Zhou, L., Du, X. X., Ji, Y., Xu, J., Tian, J., Jiang, W., Zou, Y., Yu, S., Gan, L., et al. (2011). Rheb1 is required for mTORC1 and myelination in postnatal brain development. Dev Cell 20, 97-108.

Zuccato, C., Ciammola, A., Rigamonti, D., Leavitt, B. R., Goffredo, D., Conti, L., MacDonald, M. E., Friedlander, R. M., Silani, V., Hayden, M. R., et al. (2001). Loss of huntingtin-mediated BDNF gene transcription in Huntington's disease. Science 293, 493-498.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating Huntington's disease (HD) in a subject in need thereof, comprising directly administering into striata brain tissues of the subject an AAV vector comprising a nucleic acid encoding a constitutively active Ras homolog enriched in brain (Rheb) mutant protein sequence as set forth in SEQ ID NO:2, wherein serine at position 16 of SEQ ID NO: 2 is replaced with a histidine (S16H), wherein said nucleic acid sequence is operably linked to a promoter for directing expression of the constitutively active Rheb mutant protein into the striata brain tissues of the subject, wherein said expression improves motor function in the subject, thereby treating the HD, and wherein the AAV vector is AAV1, AAV2, AAV5, AAV6 or AAV9.

2. The method of claim 1, wherein the AAV is AAV2.

3. The method of claim 1, wherein the AAV is AAV2/1.

4. The method of claim 1, wherein the subject is human.

5. The method of claim 1, wherein the constitutively active Rheb mutant protein expression into the striata brain tissues increases medium spiny neurons (MSNs) cell size as compared to control-treated contralateral hemispheres.

6. The method of claim 1, wherein the constitutively active Rheb mutant protein expression into the striata brain tissues upregulates expression of a mitochondrial transcriptional regulator, PGC1-α.

* * * * *

SEQUENCE LISTING

<160> NUMBER OF SEQ ID NOS: 4

<210> SEQ ID NO 1
<211> LENGTH: 2092
<212> TYPE: DNA
<213> ORGANISM: Homo sapiens

<400> SEQUENCE: 1

```
ggcgtaatta aaaagcggcg gaagaaggtg ggagggtcat gacgcagcga gtttcagtcg      60 tgactttct  gggggcatcg cggcgtcccc ttttttttgcc tttaaagtaa aacgtcgccc     120
cgacgcaccc cccgcgtatt tcggggggcg gaggcggcgg gccacggcgc gaagagggggc    180 ggtgctgacg ccggccggtc acgtgggcgt gttgtggggg ggagggggcgc cgccgcgcgg    240
```

|  |  |
|---|---|
| tcggttccgg gcggttggga gcgcgcgagc tagcgagcga gaggcagccg cgcccgccgc | 300 |
| cgccctgct ctgtatgccg ctctctcccg gcgcggccgc cgccgatcac agcagcagga | 360 |
| gccaccgccg ccgcggttga tgtggttggg ccggggctga ggaggccgcc aagatgccgc | 420 |
| agtccaagtc ccggaagatc gcgatcctgg gctaccggtc tgtggggaaa tcctcattga | 480 |
| cgattcaatt tgttgaaggc caatttgtgg actcctacga tccaaccata gaaaacactt | 540 |
| ttacaaagtt gatcacagta aatggacaag aatatcatct tcaacttgta gacacagccg | 600 |
| ggcaagatga atattctatc tttcctcaga catactccat agatattaat ggctatattc | 660 |
| ttgtgtattc tgttacatca atcaaaagtt ttgaagtgat taaagttatc catggcaaat | 720 |
| tgttggatat ggtggggaaa gtacaaatac ctattatgtt ggttgggaat aagaaagacc | 780 |
| tgcatatgga aagggtgatc agttatgaag aagggaaagc tttggcagaa tcttggaatg | 840 |
| cagcttttt ggaatcttct gctaaagaaa atcagactgc tgtggatgtt tttcgaagga | 900 |
| taattttgga ggcagaaaaa atggacgggg cagcttcaca aggcaagtct tcatgctcgg | 960 |
| tgatgtgatt ctgctgcaaa gcctgaggac actgggaata tattctacct gaagaagcaa | 1020 |
| actgcccgtt ctccttgaag ataaactatg cttctttttt cttctgttaa cctgaaagat | 1080 |
| atcatttggg tcagagctcc cctcccttca gattatgtta actctgagtc tgtccaaatg | 1140 |
| agttcacttc cattttcaaa ttttaagcaa tcatattttc aatttatata ttgtatttct | 1200 |
| taatattatg accaagaatt ttatcggcat taattttca gtgtagtttg ttgtttaaaa | 1260 |
| taatgtaatc atcaaaatga tgcatattgt tacactacta ttaactaggc ttcagtatat | 1320 |
| cagtgtttat ttcattgtgt taaatgtata cttgtaaata aaatagctgc aaacctcagt | 1380 |
| cctttgtgct acttgatgtg gctttcaaag aagagaagcc ttgtcctgag tttctcactt | 1440 |
| ggcttcagga aggccccagg ttggattcca gaaaccagtg aagatgtggc cacaggagga | 1500 |
| ggtgtgctga ggtggctgct gaccgtggac tccctgcgca gtggcctgca gatgttgggg | 1560 |
| ctgggttaca gctgattgaa gctgagtggc cctgggtggt ctgtgagggg agttcctccc | 1620 |
| cagtgatgaa attctctcct tccaccctca aatccctaga ccttgactga aatgctccgt | 1680 |
| ggtcgggagc ctggtcaagg aggaggagct gctgagaggc attgttcgcc cttgctcata | 1740 |
| gcttagctcg atgtccgtgt cagacaggag atgattgaga acagccttgc ctgtcactgt | 1800 |
| cctagaacac cctggagttt agtgttctgt gtcagagtct tgggagcctc cttcagaccc | 1860 |
| agatgacggg cctccctctg tccaaggagc agctgtaaag gagaagaggg atttcatttg | 1920 |
| tttggtggct gttaccttgt ctgtaagtca aacttggagt tgagcagtgc tttttaaacg | 1980 |
| attccctttt gcagctaaaa tttcacaggg ctatttctaa tacgtaagca aatgttacca | 2040 |
| ttgactttat taataaaata tagttttgct ttgcaaaaaa aaaaaaaaaa aa | 2092 |

<210> SEQ ID NO 2
<211> LENGTH: 184
<212> TYPE: PRT
<213> ORGANISM: Homo sapiens

<400> SEQUENCE: 2

Met Pro Gln Ser Lys Ser Arg Lys Ile Ala Ile Leu Gly Tyr Arg Ser
1               5                   10                  15

Val Gly Lys Ser Ser Leu Thr Ile Gln Phe Val Glu Gly Gln Phe Val
                20                  25                  30

Asp Ser Tyr Asp Pro Thr Ile Glu Asn Thr Phe Thr Lys Leu Ile Thr
            35                  40                  45

Val Asn Gly Gln Glu Tyr His Leu Gln Leu Val Asp Thr Ala Gly Gln
 50                  55                  60

Asp Glu Tyr Ser Ile Phe Pro Gln Thr Tyr Ser Ile Asp Ile Asn Gly
 65                  70                  75                  80

Tyr Ile Leu Val Tyr Ser Val Thr Ser Ile Lys Ser Phe Glu Val Ile
                 85                  90                  95

Lys Val Ile His Gly Lys Leu Leu Asp Met Val Gly Lys Val Gln Ile
                100                 105                 110

Pro Ile Met Leu Val Gly Asn Lys Lys Asp Leu His Met Glu Arg Val
                115                 120                 125

Ile Ser Tyr Glu Glu Gly Lys Ala Leu Ala Glu Ser Trp Asn Ala Ala
130                 135                 140

Phe Leu Glu Ser Ser Ala Lys Glu Asn Gln Thr Ala Val Asp Val Phe
145                 150                 155                 160

Arg Arg Ile Ile Leu Glu Ala Glu Lys Met Asp Gly Ala Ala Ser Gln
                165                 170                 175

Gly Lys Ser Ser Cys Ser Val Met
                180

<210> SEQ ID NO 3
<211> LENGTH: 3047
<212> TYPE: DNA
<213> ORGANISM: Homo sapiens

<400> SEQUENCE: 3

| | | | | | |
|---|---|---|---|---|---|
| cccttgcgcc | tccttgcccg | gccgcgccca | gccggcgtc | ccgagcagcg | caggggagga | 60 |
| tccccgcgca | gtgacccggg | agccaccaca | gactctggga | ggctcggcgg | ctggagcagc | 120 |
| aggcagctcc | ccgcagctcc | cggcgcttcc | aggcagctct | ctgagccgtg | ccagaggccc | 180 |
| ggcccgccat | tcccagcccc | gagccatgat | gaagactttg | tccagcggga | actgcacgct | 240 |
| cagtgtgccc | gccaaaaact | cataccgcat | ggtggtgctg | ggtgcctctc | gggtgggcaa | 300 |
| gagctccatc | gtgtctcgct | tcctcaatgg | ccgctttgag | gaccagtaca | cacccaccat | 360 |
| cgaggacttc | caccgtaagg | tatacaacat | ccgcggcgac | atgtaccagc | tcgacatcct | 420 |
| ggatacctct | ggcaaccacc | ccttccccgc | catgcgcagg | ctgtccatcc | tcacagggga | 480 |
| tgtcttcatc | ctggtgttca | gcctggataa | ccgggagtcc | ttcgatgagg | tcaagcgcct | 540 |
| tcagaagcag | atcctggagg | tcaagtcctg | cctgaagaac | aagaccaagg | aggcggcgga | 600 |
| gctgccatg | gtcatctgtg | caacaagaa | cgaccacggc | gagctgtgcc | gccaggtgcc | 660 |
| caccaccgag | gccgagctgc | tggtgtcggg | cgacgagaac | tgcgcctact | cgaggtgtc | 720 |
| ggccaagaag | aacaccaacg | tggacgagat | gttctacgtg | ctcttcagca | tggccaagct | 780 |
| gccacacgag | atgagcccg | ccctgcatcg | caagatctcc | gtgcagtacg | gtgacgcctt | 840 |
| ccaccccagg | cccttctgca | tgcgccgcgt | caaggagatg | gacgcctatg | catggtctc | 900 |
| gcccttcgcc | cgccgcccca | gcgtcaacag | tgacctcaag | tacatcaagg | ccaaggtcct | 960 |
| tcgggaaggc | caggcccgtg | agagggacaa | gtgcaccatc | cagtgagcga | gggatgctgg | 1020 |
| ggcgggcctt | ggccagtgcc | ttcagggagg | tggccccaga | tgcccactgt | gcgcatctcc | 1080 |
| ccaccgaggc | cccggcagca | gtcttgttca | gagaccttag | gcaccagact | ggaggccccc | 1140 |
| gggcgctggc | ctccgcacat | tcgtctgcct | tctcacagct | ttcctgagtc | cgcttgtcca | 1200 |
| cagctccttg | gtggtttcat | ctcctctgtg | ggaggacaca | tctctgcagc | ctcaagagtt | 1260 |
| aggcagagac | tcaagttaca | ccttcctctc | ctgggggttgg | aagaaatgtt | gatgccagag | 1320 |

```
gggtgaggat tgctgcgtca tatggagcct cctgggacaa gcctcaggat gaaaaggaca      1380
cagaaggcca gatgagaaag gtctcctctc tcctggcata acacccagct tggtttgggt      1440
ggcagctggg agaacttctc tcccagccct gcaactctta cgctctggtt cagctgcctc      1500 tgcacccect cccacccca gcacacacac aagttggccc ccagctgcgc ctgacattga       1560
```

```
gggtgaggat tgctgcgtca tatggagcct cctgggacaa gcctcaggat gaaaaggaca      1380
cagaaggcca gatgagaaag gtctcctctc tcctggcata acacccagct tggtttgggt      1440
ggcagctggg agaacttctc tcccagccct gcaactctta cgctctggtt cagctgcctc      1500 tgcacccect cccaccccca gcacacacac aagttggccc ccagctgcgc ctgacattga      1560
gccagtggac tctgtgtctg aaggggcgt ggccacacct cctagaccac gcccaccact       1620
tagaccacgc ccacctcctg accgcgttcc tcagcctcct ctcctaggtc cctccgcccg      1680
acagttgtgc tttgttgtgg ttgcagctgt tttcgtgtca tgtatagtag tagaaatgga     1740
aatcattgta ctgtaaaagc ctagtgactc cctccttggc caggccctca cccagttcag      1800
atccacggcc tccacccggg acgccttcct cctctgctcc caaacagggt ttccgtggcc      1860
tgtttgcagc tagacattga cctccgccat tgagctccac ggtttacaga caattgcaca     1920
agcgtggggt gggcaggcca ggactgcttt tttttaatgc tcccatttca cagaggatac      1980
caccgagact cggaggggac acgatgagca ccaggcccca cctttgtccc ctagcaaatt     2040
cagggtacag ctccacctag aaccaggctg ccctctactg tgctcgttcc tcaagcattt     2100
attaagcacc tactgggtgc tgggttcact gtgtcctagg aaaccaagag ggtccccagt     2160
cctggcctct gcccgcccct gctgccccac caccttctgc acacacagcg gtggggaggc     2220
ggggaggagc agctgggacc cagaactgag cctgggaggg atccgacaga aaagctcagg     2280
gcgggtcttc tccttgtgcc cgggattggg ctatgctggg taccaccatg tactcaggca     2340
tggtgggttt tgaacccata accaaaggc ccttgtcatc agctcttaac aagtatattt      2400 tgtatttta tctctctaaa catattgaag ttttagggcc ctaaggaacc ttagtgatct      2460
tctattgggt ctttctgagg ttcagagagg gtaagtaact tcctccaggt cacacagcaa     2520
gtctgtgggt ggcagaagca agctagcgct gggcattcag tacataccac gatgtgctcc     2580
ctctcttgat gcttggcccc tggggccttc agggctttgg gacatcttgt cctcaaccct     2640
ctccctagat cagtctgtga gggtccctgt agatattgtg tacaccatgc ccatgtatat     2700
acaagtacac acagatgtac acacagatgt acacatgctc cagcccccagc tctgcatacc    2760 tgcacctgca ccccagcctt ggcccctgcc tgcgtctgtg ctcaaagcag cagctccaac    2820
cctgcctctg tccccttccc cacccactgc ctgagccttc tgagcagacc aggtaccttg     2880
gctgcaccgg tgtgtggccc gctctcaccc aggcacagcc ccgccaccat ggatctccgt     2940
gtacactatc aataaaagtg gtttgttac aaaaaaaaaa aaaaaaaaaa aaaaaaaaa       3000 aaaaaaaaa aaaaaaaaaa aaaaaaaaa aaaaaaaaa aaaaaaa                      3047
```

<210> SEQ ID NO 4
<211> LENGTH: 266
<212> TYPE: PRT
<213> ORGANISM: Homo sapiens

<400> SEQUENCE: 4

Met Met Lys Thr Leu Ser Ser Gly Asn Cys Thr Leu Ser Val Pro Ala
1               5                   10                  15

Lys Asn Ser Tyr Arg Met Val Val Leu Gly Ala Ser Arg Val Gly Lys
            20                  25                  30

Ser Ser Ile Val Ser Arg Phe Leu Asn Gly Arg Phe Glu Asp Gln Tyr
        35                  40                  45

Thr Pro Thr Ile Glu Asp Phe His Arg Lys Val Tyr Asn Ile Arg Gly
    50                  55                  60

-continued

```
Asp Met Tyr Gln Leu Asp Ile Leu Asp Thr Ser Gly Asn His Pro Phe
65                  70                  75                  80

Pro Ala Met Arg Arg Leu Ser Ile Leu Thr Gly Asp Val Phe Ile Leu
                85                  90                  95

Val Phe Ser Leu Asp Asn Arg Glu Ser Phe Asp Glu Val Lys Arg Leu
            100                 105                 110

Gln Lys Gln Ile Leu Glu Val Lys Ser Cys Leu Lys Asn Lys Thr Lys
        115                 120                 125

Glu Ala Ala Glu Leu Pro Met Val Ile Cys Gly Asn Lys Asn Asp His
        130                 135                 140

Gly Glu Leu Cys Arg Gln Val Pro Thr Thr Glu Ala Glu Leu Leu Val
145                 150                 155                 160

Ser Gly Asp Glu Asn Cys Ala Tyr Phe Glu Val Ser Ala Lys Lys Asn
                165                 170                 175

Thr Asn Val Asp Glu Met Phe Tyr Val Leu Phe Ser Met Ala Lys Leu
                180                 185                 190

Pro His Glu Met Ser Pro Ala Leu His Arg Lys Ile Ser Val Gln Tyr
            195                 200                 205

Gly Asp Ala Phe His Pro Arg Pro Phe Cys Met Arg Arg Val Lys Glu
            210                 215                 220

Met Asp Ala Tyr Gly Met Val Ser Pro Phe Ala Arg Arg Pro Ser Val
225                 230                 235                 240

Asn Ser Asp Leu Lys Tyr Ile Lys Ala Lys Val Leu Arg Glu Gly Gln
                245                 250                 255

Ala Arg Glu Arg Asp Lys Cys Thr Ile Gln
            260                 265
```